US007005424B2

(12) United States Patent
Hung et al.

(10) Patent No.: US 7,005,424 B2
(45) Date of Patent: Feb. 28, 2006

(54) NUCLEIC ACID ENCODING AN E1A GENE PRODUCT SENSITIZES HER-2/NEU OVEREXPRESSING CANCER CELLS TO CHEMOTHERAPY

(75) Inventors: Mien-Chie Hung, Houston, TX (US); Naoto T. Ueno, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 371 days.

(21) Appl. No.: 09/943,984

(22) Filed: Aug. 31, 2001

(65) Prior Publication Data

US 2004/0053863 A1 Mar. 18, 2004

Related U.S. Application Data

(63) Continuation of application No. 08/809,021, filed on Mar. 19, 1997, now Pat. No. 6,395,712.

(60) Provisional application No. 60/013,750, filed on Mar. 20, 1996.

(51) Int. Cl.
*A01N 43/04* (2006.01)
*A01N 63/00* (2006.01)
*A61K 31/70* (2006.01)
*A61K 9/27* (2006.01)
*A61K 48/00* (2006.01)

(52) U.S. Cl. .......................... 514/44; 424/93.2; 424/450
(58) Field of Classification Search .................. 514/44; 424/93.21, 450, 93.2
See application file for complete search history.

(56) References Cited

U.S. PATENT DOCUMENTS

| 4,394,448 A | 7/1983 | Szoka, Jr. et al. .......... 435/172 |
| 5,641,484 A | 6/1997 | Hung et al. ................ 424/93.2 |
| 5,643,567 A | 7/1997 | Hung et al. |
| 5,651,964 A | 7/1997 | Hung et al. ................ 424/93.2 |
| 5,776,743 A | 7/1998 | Frisch |
| 5,814,315 A | 9/1998 | Hung et al. ................ 424/93.2 |
| 6,197,754 B1 * | 3/2001 | Hung et al. ................ 424/93.2 |
| 6,271,207 B1 | 8/2001 | Cristiano et al. ............. 514/44 |
| 6,326,356 B1 * | 12/2001 | Hung et al. ................... 514/44 |
| 6,395,712 B1 * | 5/2002 | Hung et al. ................... 514/44 |
| 6,683,059 B1 * | 1/2004 | Hung et al. ................... 514/44 |

FOREIGN PATENT DOCUMENTS

| WO | WO 90/08759 A | 8/1990 |
| WO | WO 90/15595 | 12/1990 |
| WO | WO 92/10573 A | 6/1992 |
| WO | WO 93/03769 | 3/1993 |
| WO | WO 94/21115 | 9/1994 |
| WO | WO 95/13813 A | 5/1995 |
| WO | WO 95/16051 | 6/1995 |

OTHER PUBLICATIONS

Powles et al. A Randomised Trial Comparing Combination Chemotherapy Using Mitomycin C, Mitozantrone and Methotrexate (3M) with Vincristine, Anthracylcline and Cyclophosphamide (VAC) In Advanced Breast Cancer. Brit. J. Cancer, 1991, vol. 64, pp. 406-410.*

Larsson et al. Cytotoxic Activity of Topoisomerase II Inhibitors in Primary Cultures of Tumor Cells from Patients with Human Hematologic and Solid Tumors. Cancer. 1994, vol. 74, pp. 2857-2862.*

Culine et al. Long-Term Results of Two VAB-Like Regimes in Malignant Germ Cell Tumours of the Ovary. Eur. J. Cancer. 1994, 30A, pp. 1239-1244.*

Norton, L. Salvage Chemotherapy of Breast Cancer. Seminars in Oncol. 1994, vol. 21, pp. 19-24.*

Akiyama et al., "Genistein, a Specific Inhibitor of Tyrosine-Specific Protein Kinases," *J. Biol. Chem.*, 262(12):5592-5595, 1987.

Bacus et al., Differentiation of cultured human breast cancer cells (AU-565) and MCF-7) associated with loss of cell surface *HER-2/neu* antigen. *Mol. Carcinog.*, 3:350-362, 1990.

Bacus, et al., Tumor-inhibitory monoclonal antibodies to the *HER-2/neu* receptor induce differentiation of human breast cancer cells. *Cancer Res.* 52: 2580-2589, 1992.

Bargmann & Weinberg, "Increased Tyrosine Kinase Activity Associated with the Protein Encoded by the Activated Neu Oncogene, " *Proc. Natl. Acad. Sci. USA*, 85:5394-5398, 1988.

Bargmann et al., "Multiple Independent Activations of the neu Oncogene by a Point Mutation Altering the Transmembrane Domain of p185," *Cell*, 45:649-657, 1986.

Bargmann et al., "The neu Oncogene Encodes an Epidermal Growth Factor Receptor-Related Protein," *Nature*, 319:226-230, 1986.

Berk and Sharp, "Structure of the Adenovirus 2 Early mRNAs," *Cell*, 14:695-711, 1978.

Berk, "Adenovirus Promoters and EIA Transactivation," *Ann. Rev. Genet.*, 20:45-79, 1986.

Bishop JM "The molecular genetics of cancer," *Science*, 235 (4786), p305-11, 1987.

(Continued)

*Primary Examiner*—Deborah Crouch
(74) *Attorney, Agent, or Firm*—Fulbright & Jaworski L.L.P.

(57) ABSTRACT

The present invention relates to methods for the inhibition, of the gene product of the neu oncogene, p185neu tyrosine kinase. Over-expression of the neu oncogene leads to chemoresistance. The methods disclosed involve the novel use of E1A and/or LT in combination with chemotherapeutic drugs to treat carcinoma. Furthermore, E1A surprisingly potentiates the antineoplastic effects of the chemotherapeutic agents. The inventors propose that E1A sensitizes cancer cells such that they become amenable to treatment by chemotherapeutic drugs.

108 Claims, 45 Drawing Sheets

OTHER PUBLICATIONS

Brader et al., "Adenovirus E1 A Expression Enhances the Sensitivity of an Ovarian Cancer Line to Multiple Cytotoxic Agents Through an Apoptotic Mechanisms," Proceedings of the American Association for Cancer Research, 37:30, 1996. (abstract).

Brunet et al., "Concentration Dependence of Transcriptional Transactivation in Inducible E1A-Containing Human Cells," *Mol. Cell. Bio.*, 8(11):4799-4807 (1988).

Buchman et al., Appendix A: The SV40 Nucleotide Sequence, *DNA Tumor Viruses*, 799-813.

Chan et al., "Selective inhibition of the growth of ras-transformed human bronchial epithelial cells by emodin, a protein-tyrosine inhibitor," *Biochem. Biophys. Res. Commun.*, 193:1152-1158, 1993.

Chang, et al., "Paclitaxel by 3-hour infusion followed by 96-hour infusion on failure in patients with refractory malignant disease," *Seminars in Oncology*, 22(3, Supp.6): 124-127, 1995.

Chevalier, Fumoleau, Kerbrat, Dieras, Roche, Krakowski, Azli, Bayssas, Lentz, Van Glabbeke, "Decetaxel is a major cytotoxic drug for the treatment of advanced breast cancer: a phase II trial of the Clinical Screening Cooperative Group of the European Organization for Research and Treatment of Cancer," *J. Clin. Oncol.*, 13:314-322, 1995.

Coussens et al., "Tyrosine Kinase Receptor with Extensive Homology to EGF Receptor Shares Chromosomal Location with neu Oncogene," *Science*, 230:1132-1139, 1985.

Douglas et al., "Modulation of transformation of primary epithelial cells by the second exon of the Ad55 E1A12S gene," *Oncogene*, 6:2093-2103, 1991.

Downward et al., "Close Similarity of Epidermal Growth Factor Receptor and v-erb-B Oncogene Protein Sequences," *Nature*, 307:521-527, 1984.

Egan et al., "Transformation by Oncogenes Encoding Protein Kinases Induces the Metastatic Phenotype," *Science*, 238:202-205, 1987.

Felgner et al., "Gene Therapeutics: The Direct Delivery of Purified Genes in vivo and Their Application as Drugs, Without the Use of Retroviruses, Is Discussed," *Nature*, 349:351-352 (1991).

Felgner, P.L., and Ringold, G.M., Cationic liposome-mediated transfection, *Nature*, 337:387-388, 1989.

Figge et al., "Prediction of Similar Transforming Regions in Simian Virus 40 Large T, Adenovirus E1A, and myc Oncoproteins," *Journal of Virology*, 62:(5)1814-1818, 1988.

Freedman and Shin, "Use of Nude Mice for Studies on the Tumorigenicity of Animal Cells," *The Nude Mouse in Experimental and Clinical Research*, 1978.

Friche et al., "Effect of anthracycline analogs on photolabelling of p-glycoprotein by [125I]iodomycin and [eH] azidopine: relation to lipophilicity and inhibition of daunorubicin transport in multidrug resistant cells," *Br. J. Cancer*, 67(2):226-231, 1993.

Frisch et al., "Adenovirus E1A Represses Protease Expression and Inhibits Metastasis of Human Tumor Cells," *Oncogene*, 5:75-83 (1990).

Fung et al., "Activation of the Cellular Oncogene c-erbB by LTR Insertion: Molecular Basis for Induction of Erythroblastosis by Avian Leukosis Virus", *Cell*, 33:357-368, 1983.

Gazit et al., "Chemo-adoptive immunotherapy of nude nice implanted with human colorectal carcinoma and melanoma cell lines," *Cancer Immunology Immunotherapy*, 35:135-144, 1992.

Giovanella, Stehlin, Shepard, Williams, "Correlation between response to chemotherapy of human tumors in patients and in nude mice," *Cancer*, 52:1146-1152, 1982.

Goo, X., and Huang, L., A Novel Cationic Liposome Reagent for Efficient Transfection of Mammalian Cells, *Biochemical and Biophysical Research Communication*, 179:(1)280-285, 1991.

Haley et al., "Transformation Properties of Type 5 Adenovirus Mutants that Differentially Express the E1A Gene Products," *Proc. Natl. Acad. Sci. USA*, 81:5734-5738, 1984.

Harlow et al., "Monoclonal Antibodies Specific for Adenovirus Early Region 1A Proteins: Extensive Heterogeneity in Early Region IA Products," *J. of Virology*, 55(3):533-546 (1985).

Hearing et al., "Sequence-Independent Autoregulation of the Adenovirus Type 5 E1A Transcription Unit," *Mol. Cell. Bio.*, 5(11):3214-3221 (1985).

Houweling et al., "Partial Transformation of Primary Rat Cells by the Leftmost 4.5% Fragment of Adenovirus 5 DNA," *J. Virology*, 105:537-550, 1980.

Hudziak et al., "Amplified Expression of the HER2/ERBB2 Oncogene Induces Resistance to Tumor Necrosis Factor a in NIH 3T3 Cells," *Proc. Natl. Acad. Sci. USA*, 85:5102-5106, 1988.

Hudziak et al., "Increased expression of the putative growth factor p 185 j$^2$ causes transformation and tumorigenesis of NIH 3T3 cells," *Proc. Natl. Acad. Sci. USA*, 84:7159-7163, 1987.

Hung et al., "Amplification of the proto-neu oncogene facilitates oncogenic activation by a single point mutation," *Proc. Natl. Acad. Sci. USA*, 86:2545-2548, 1989.

Hung et al., "Molecular cloning of the neu gene: absence of gross structural alteration in oncogenic alleles," *Proc. Natl. Acad. Sci. USA*, 83:261-264, 1986.

Hung, "The neu Proto-Oncogene and Breast Cancer," *Cancer Bull.*, 40:300-303, 1988.

Hung, et al., "Transcriptional Repression of the HER-2/neu Protooncogene by Transforming Oncogenes from DNA Tumor Virus," Proceedings of the American Association for Cancer Research, Washington, DC, 31:13, Abstract No. 74.

Jayasuriya et al. "Emodin, a protein tyrosine kinase inhibitor from *Polygonum cuspidatum,*" *J. Nat. Prod.*, 55:696-698, 1992.

Jinsart et al., "Inhibition of Myosin Light Chain Kinase, cAMP-Dependent Protein Kinase, Protein Kinase C and of Plant CA-Dependent Protein Kinase by Anthraquinones," *Biological Chemistry*, 373:903-910, 1992.

Kalderon, D., and Smith, A.E., "In Vitro Mutagenesis of a Putative DNA Binding Domain of SV40 Large-T," *Virology*, 139:109-137, 1984.

Katsumata et al., "Prevention of breast tumor development in vivo by down-regulation of the p185$^{neu}$ receptor" :*Nature Med.*, 1: 644-648. 1995.

Kelner, Memorris, Estes, Starr, Samson, Varki, Taetle, "Nonresponsiveness of the metastatic human lung carcinoma MV522 xenograft to conventional anticancer agents," *Anticancer Res.*, 15:867-872, 1995.

Kern et al., "p185$^{neu}$ expression in human lung adenocarcinomas predicts shortened survival," *Cancer Res.*, 50:5184-5191, 1990.

Kiyokawa N ; Yan DH; Brown ME; Hung MC "Cell cycle-dependent regulation of p185neu: a relationship between disruption of this regulation and transformation." *Proc Natl Acad Sci USA*, 92 (4) p1092-61995.

Kraus et al., "Overexpression of the EGF Receptor-Related Proto-Oncogene erbB-2 in Human Mammary Tumor Cell Lines by Different Molecular Mechanisms," *EMBO J.*, 6(3): 605-610, 1987.

Kupchan and Karim, "Tumor Inhibitors 114. Aloe Emodin: Antileukemia Principle Isolated from *Rhamnus frangula*," *L. Lloydia*, 39:223-224, 1976.

Land et al., "Cellular Oncogenes and Multistep Carcinogenesis," *Science*, 222:771-776, 1983.

Lee, Bruckner, Szrajer, Brenne, Schindelheim, Andretti, "Taxol inhibits growth of Mesothelioma xenografts," *Anticancer Res.*, 15:693-696, 1995.

Lehvaslaiho et al., "A chimeric EGF-R-neu proto-oncogene allows EGF to regulate neu tyrosine kinase and cell transformation," *EMBO Journal*, 8:(1)159-166, 1989.

Leibiger et al., "Expression of exogenous DNA in rat liver cells after liposome-mediated transfection in vivo," *Biochemcical and Biophysical Research Communications*, 174:(32)1223-1231, 1991.

Li et al., "Method of Identifying Inhibitors of Oncogenic Transformation: Selective Inhibition of Cell Growth in Serum-Free Medium," *Oncogene*, 8:1731-1735, 1993.

Lichtenstein et al., "Resistance of Human Ovarian Cancer Cells to Tumor Necrosis Factor and Lymphokine-Activated Killer Cells: Correlation with Expression of HER2/neu Oncogenes," *Cancer Research*, 50:7364-7370,1990.

Liu et al., "Evidence for Involvement of Tyrosine Phosphorylation in Taxol-Induced Apoptosis in a Human Ovarian Tumor Cell Line," *Biochem. Pharmacol.*, 48(6): 1265-1272, 1994.

Lupu et al., "Direct Interaction of a Ligand for the erbB2 Oncogene Product with the EGF Receptor and $p185^{erbB2}$," *Science*, 249:1552-1554, 1990.

Matin and Hung, "Negative Regulation of the Neu Promoter by the SV40 Large T Antigen," *Cell Growth & Differentiation*, 4:1051-1056, 1993.

Matin, "Regulation of neu gene expression by the simian virus 40 large T antigen and tumor suppressors Rb and p53," *Diss. Abstra. Int. B*, 54(5):2365, 1993.

Minna et al., "Cancer of the lung," In: Devita, V.T., Hellmen, S., Rosenberg, S.A. (eds.) *In: Principles and Practice of Oncology*, Philadelphia: J.B. Lippincott, pp591-705, 1989.

Montell et al., "complete Transformation by Adenovirus 2 Requires Both E1A Proteins," *Cell*, 36:951-961, 1984.

Moran et al., "Multiple Functional Domains in the Adenovirus E1A Gene," *Cell*, 48:177-178 (1987).

Müller et al., "Differential Expression of Cellular Oncogenes During Pre- and Postnatal Development of the Mouse," *Nature*, 299:640-644, 1982.

Muller et al., " Single-Step Induction of mammary adenocarcinoma in transgenic mice bearing the activated c-neu oncogene," *Cell*, 54:105-115, 1988.

Muthuswamy et al., "Mammary tumors expressing the neu proto-oncogene possess elevated c-src tyrosine kinase activity," *Mol. Cell. Biol.*, 14:735-743, 1994.

Nabel et al., "Site-Specific Gene Expression in Vivo by Direct Gene Transfer into the Arterial Wall," *Science*, 249: 1285-88 (1990).

Nicolau et al., Liposomes as Carriers for Gene Transfer in Vivo, *Biology Cell*, 47:121-130, 1983.

Nicolau et al., Liposomes as Carriers for in Vivo Gene Transfer and Expression, *Methods in Enzymology*, 149:157-177, 1987.

Nicolau et al., Liposomes for Gene Transfer and Expression in Vivo, *Colloids and Surfaces*, 14:325-337, 1985.

Offringa et al., "A Novel Function of the Transforming Domain of E1a: Repression of AP-1 Activity," *Cell*, 62:527-538, 1990.

Plowman et al., "Ligand-specific activation of HER4/$p180^{erbB4}$ a fourth member of the epidermal growth factor family," *Proc. Natl. Acad. Sci. USA* 90:1746-1750, 1993.

Pozzatti et al., "Primary Rat Embryo Cells Transformed by One or Two Oncogenes Show Different Metastatic Potentials," *Science*, 232:223-227, 1986.

Pozzatti et al., "The E1a Gene of Adenovirus Type 2 Reduces the Metastatic Potential of ras-Transformed Rat Embryo Cells," *Mol. Cell Biol.*, 8(7):2984-2988, 1988.

Reardon, D.B. and M. Hung, "Downstream Signal Transduction Defects That Suppress Transformation in Two Revertant Cell Lines Expressing Activated Rat neu Oncogene," *J. Biol. Chem.*, 268(24):18136-18142, 1993.

Ruley, "Adenovirus Early Region 1A Enables Viral and Cellular Transforming Genes to Transform Primary Cells in Culture," *Nature*, 304:602-606 (1983).

Rustgi et al., "Amino-terminal domains of c-myc and N-myc proteins mediate binding to the retinoblastoma gene product," *Nature*, 352:541-544, 1991.

Sassone-Corsi & Borrelli, "Promoter Trans-Activation of Protooncogenes c-fox and c-myc, but not c-Ha-ras, by Products of Adenovirus Early Region 1A," *Proc. Natl. Acad. Sci. USA*, 84:6430-6433, 1987.

Schrechter et al., "The neu oncogene: an erb-B-related gene encoding a 185,000-M, tumour antigen," *Nature*, 312:513-516, 1984.

Schecter et al., "The neu Gene: An erbB-Homologous Gene Distinct from and Unlinked to the Gene Encoding the EGF Receptor," *Science*, 229:976-978, 1985.

Schneider et al., "Differential expression of the c-erbB-2 gene in human non-small cell lung cancer," *Cancer Res.*, 49:4968-4971, 1981.

Semba et al., "A v-erbB-related protooncogene, c-erbB-2, is distinct from the c-erbB-11/epidermal growth factor-receptor gene and is amplified in a human salivary gland adenocarcinoma," *Proc. Natl. Acad. Sci. USA*, 82:6497-6501, 1985.

Senear et al., "Morphological Transformation of Established Rodent Cell Lines by High-Level Expression of the Adenovirus Type 2 E1a Gene," *Mol. Cell. Bio.*, 6(4):1253-1260 (1986).

Seshadri et al., "The Significance of Oncogene Amplification in Primary Breast Cancer," *Int. J. Cancer*, 43:270-272, 1989.

Shepard, H. M. and G. D. Lewis, "Resistance of Tumor Cells to Tumor Necrosis Factor," *J. of Clin. Immunol.* 8(5):333-341, 1988.

Shih et al., "Transforming genes of carcinomas and neuroblastomas introduced into mouse fibroblasts", *Nature* (London), 290:261-264, 1981.

Shih et al., "Transforming Genes of Carcinomas and Neuroblastomas Introduced into Mouse Fibroblasts," *Nature* 290:261-264, 1981.

Shin, "Use of Nude Mice for Tumorigenicity Testing and Mass Propagation," *Methods in Enzymology*, 58:370-379, 1979.

Siegel PM; Dankort DL; Hardy WR; Muller WJ, "Novel activating mutations in the neu proto-oncogene involved in induction of mammary tumors." *Mol Cell Biol*, 14 (11) p7068-77, 1994.

Sistonen et al., "Activation of the neu tyrosine kinase induces the fos/jun transcription factor complex, the glucose transporter, and ornithine decarboxylase," *J. Cell. Biol.*, 109:1911-1919, 1989.

Slamon et al., "Human Breast Cancer: Correlation of Relapse and Survival with Amplification of the HER-2/neu Oncogene," *Science*, 235:177-182, 1987.

Salmon et al., "Studies of the HER2/neu proto-oncogene in human breast and ovarian cancer," *Science*, 244:707-712, 1989.

Smith & Ziff, "The Amino-Terminal Region of the Adenovirus Serotype 5 E1a Protein Performs Two Separate Functions when Expressed in Primary Baby Rat Kidney Cells," *Mol. Cell Biol.*, 8(9):3882-3890, 1998.

Spandidos DA; Yiagnisis M; Papadimitriou K; Field JK "ras, c-myc and c-erbB-2 oncoproteins in human breast cancer," *Anticancer Res.* 9 (5) p1385-93, 1989.

Steeg et al., "Altered Expression of NM23, a Gene Associated with Low Tumor Metastatic Potential, during Adenovirus 2 E1a Inhibition of Experimental Metastasis," *Cancer Res.*, 48:6550-6554, 1988.

Stern, Heffernan, Weinberg, "p185, a product of the neu proto-oncogene, is a receptor like protein associated with tyrosine kinase activity," *Mol. Cell. Biol.*, 6:1729-1740, 1986.

Suen et al., "Transcriptional Regulation of Neu Oncogene," *Breast Cancer Research and Treatment*, 14(1):Abstract 213, 1989.

Suen, T., and Hung, M., "Multiple cis- and trans-Acting Elements Involved in Regulation of the neu Gene," *Molecular and Cellular Biology*, 10:(12)6306-6315, 1990.

Teramota et al., "Serum Enzyme Immunoassay Kit for the Detection of c-erbB-2 Oncoprotein," Annual AACI Meeting, Abstract # 1446, 1991.

Tooze, J., "comparison of the Regions of Polyoma Virus and SV40 That Code for Small and Large T Antigens," *Molecular Biology of Tumor Viruses*, 2nd ed. Part 2, 857-861.

Tsai et al., "Correlation of intrinsic chemoresistance of non-small-cell lung cancer cell lines with HER-1/neu gene expression but not with ras gene mutations," *J. Natl. Cancer Inst.*, 85:897-901, 1993.

Tsai et al., "Enhanced chemoresistance by elevation of the levels of p184$^{neu}$ in the HER-2/neu transfected human lung cancer cells," *J. Natl. Cancer Inst.*, 87:682-684, 1995.

Tzeng et al., "Breast cancer formation in transgenic animals induced by the whey acidic protein SV40 T antigen (WAP-SV-T) hybrid gene," *Oncogene*, 8:1965-1971, 1993.

Ullrich, A., and J. Schlessinger, "Signal Transduction by Receptors with Tyrosine Kinase Activity," *Cell*, 61:203-212, 1990.

van de Vijver et al., "NEU-Protein OverExpression in Breast Cancer: Association with Cornedo-Type Ductal Carcinoma in situ and Limited Prognostic Value in Stage II Breast Cancer," *The New England Journal of Medicine*, 319(19):1239-1245, 1988.

Vousden and Jat, "Functional Similarity bet ween HPV16E7, SV40 Large T and Adenovirus E1a Proteins," *Oncogene*, 4:153-158, 1989.

Wallich et al., "Abrogation of Metastatic Properties of Tumour Cells by de novo Expression of H-2K Antigens Following H-2 Gene Transfection," *Nature*, 315:301-305, 1985.

Weinberg, R.A., "The Action of Oncogenes in the Cytoplasm and Nucleus," *Science*, 230:770-776, 1985.

Weiner et al., "Expression of the neu gene-encoded protein (p185$^{neu}$) in human non-small cell carcinomas of the lung," *Cancer Res.*, 50:421-425, 1990.

Whyte et al., "Association between an Oncogene and an Anti-Oncogene: The Adenovirus E1A Proteins Bind to the Retinoblastoma Gene Product," *Nature*, 334:124-129 (1988).

Whyte et al., "Two Regions of the Adenovirus Early Region 1A Proteins Are Required for Transformation," *J. Virol.*, 62(1):257-265, 1988.

Whyte et al., "Cellular Targets for Transformation by the Adenovirus E1A Proteins," *Cell*, 56:67-75, 1989.

Wolff et al., "Differential Effects of the Simian Virus 40 Early Genes on Mammary Epithelial Cell Growth, Morphology, and Gene Expression," *Experimental Cell Research*, 202:67-76, 1992.

Yamamoto et al., "Similarity of protein encoded by the human c-erbB-2 gene to epidermal growth factor receptor," *Nature*, 319:230-234, 1986.

Yarden and Weinberg, "Experimental Approaches to Hypothetical Hormones: Detection of a Candidate Ligand of the neu Protooncogene," *Proc. Natl. Acad. Sci. USA*, 86:3179-3183, 1989.

Yu and Hung, "Expression of activated rat neu oncogene is sufficient to induce experimental metastasis in 3T3 cells," *Oncogene*, 6:1991-1996, 1991.

Yu et al., "Overexpression of c-erbB-2/neu in breast cancer cells confers increased resistance to Taxol via mdr-1 independent mechanisms," *Oncogene*, 13:1359-1365, 1996.

Yu et al., "Adenovirus Type 5 E1A Gene Products Act as TransformationSuppressors of the neu Oncogene," *Mol. Cell. Bio.*, 11(3):1745-1750 (1991).

Yu et al., "C-erbB-2/neu overexpression enhanced metastatic potential in human lung cancer cells by induction of metastasis-associated properties," *Cancer Res.*, 54:3260-3266, 1994.

Yu et al., "Enhanced c-erbB-2/neu expression in human ovarian cancer cells correlates with more severe malignancy that can be suppressed by E1A," *Cancer Res.*, 53:891-898, 1993.

Yu et al., Manuscript—Enhanced c-erbB-2/neu expression in human ovarian cancer cells correlates with more severe malignancy that can be suppressed by E1A (1992).

Yu, et al.., "Transcriptional repression of the neu Protooncogene by the Adenovirus 5 E1A Gene Products," *Proc Natl Acad Sci USA*, 87:4499-4503, 1990.

Yusa, Sugimot, Yamori, Yamamoto, Toyoshima, Tsuruo, "Low metastatic potential of clone from murine colon adenocarcinoma 26 increased by transfection of activated c-erb B-2 gene," *J. Natl. Cancer Inst.*, 82:1633-1636, 1990.

Zhang and Hung, "Sensitization of HER-2/neu-overexpressing Non-Small Cell Lung Cancer Cells to Chemotherapeutic Drugs by tyrosine kinase Inhibitor Emodin," *Oncogene* 12:571-576, 1996.

Zhang et al., "Emodin Inhibits Growth of Human Breast Cancer Cells and Induces Morphological Differentiation of These Cells by Its Supresion of HER-2/neu Tryosine Kinase Activity," Abstract #2595, Experimental Therapeutics: Proceedings of the American Association for Cancer Research, 36:435, 1995.

Zhang et al., "Amplification and Rearrangement of c-erb B Proto-Oncogenes in Cancer of Human Female Genital Tract," *Oncogene*, 4:985-989, 1989.

Zhang, Chang, Hung, "Suppressed transformation and induced differentiation of HER-2/neu-overexpressing breast cancer cells by emodin," *Cancer Res.*, 55:3890-3896, 1995.

Zhang, Higuchi, Totpal, Chaturvedi, Aggarwal, "Staurosporine induces the cell surface expression of both forms of human tumor necrosis factor receptors on myeloid and epithelial cells and modulates ligand-induced cellular response," *J. Biol. Chem.*, 269:10270-10279, 1994.

Zhang, Nakaya, Yoshida, Kuroiwa, "bufalin as a potent inducer of differentiation of human myeloid leukemia cells," *Biochem. Biophys. Res. Commu.*, 178, 686-693, 1991.

Zhau, et al., "Amplification and expression of the c-erb B-2/neu proto-oncogene in human bladder cancer", *Chemical Abstracts*, 114(21):205-Abstract No. 114:200732Z, 1991.

Zhou, et al., "A Retrovirus Vector which Transduces a Functional Estrogen Receptor Gene at High Efficiency," *Mol. Endocrinology*, 3(7):1157-1164, 1989.

International Search Report dated Jul. 7, 1997 (UTFC: 484P).

Ueno et al., "E1A Paclitaxel Sensitization in HER-2neu-overexpressing Ovarian Cancer SKOV3.ipl through Apopotosis Involving the Capspae-3 Pathway[1]," *Clinical Cancer Research*, 6:250-259, 2000.

Lowe et al., "p53-Dependant Apoptosis Modulates the Cytotoxicity of Anticancer Agents," *Cell*, 74:957-967, 1993.

Thatcher et al. *Cancer*, 63:1296-1302, 1989.

Valenti et al., *Eur. J. Cancer*, 29A:1157-1161, 1993.

Pietras et al., *Oncogene*, 9:1829-1838, 1994.

\* cited by examiner 0 20 15 10 5
E1A (μg)

0 20 15 10 5
E1A-13S(μg)

0 20 15 10 5
E1A-12S(μg)

0 20 15 10 5
E1A dl346(μg)

Tumorigenicity assay

| Cell Line | Time to develope tumors (No. of tumors/no. of injection) | | | | | Tumor volume at 16 days (mm³) |
|---|---|---|---|---|---|---|
| | 8 | 12 | 14 | 20 | 26 (days) | |
| B104-1-1 | 6/6 | 6/6 | 6/6 | 6/6 | 6/6 | 8240±203 |
| NIH3T3 | 0/6 | 0/6 | 0/6 | 0/6 | 0/6 | N.D. |
| N-E1A-1 | 0/6 | 0/6 | 0/6 | 0/6 | 0/6 | N.D. |
| B-E1A-1 | 0/6 | 0/6 | 0/6 | 5/6 | 6/6 | N.D. |
| B-E1A-2 | 0/6 | 2/6 | 6/6 | 6/6 | 6/6 | 216±53 |
| B-E1A-3 | 0/6 | 6/6 | 6/6 | 6/6 | 6/6 | 481±74 |

NIH3T3    B-E1A-2    B104-1-1

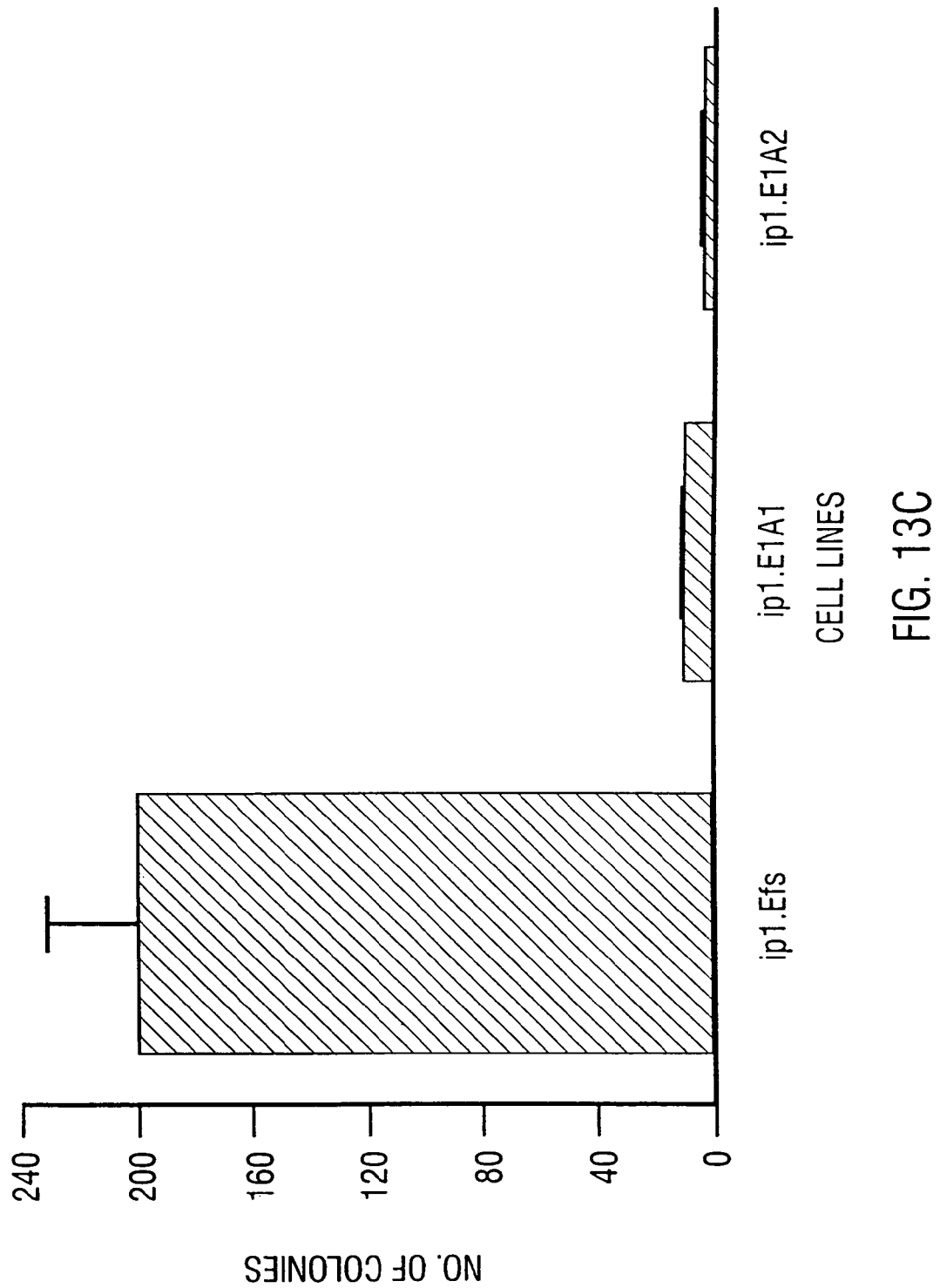

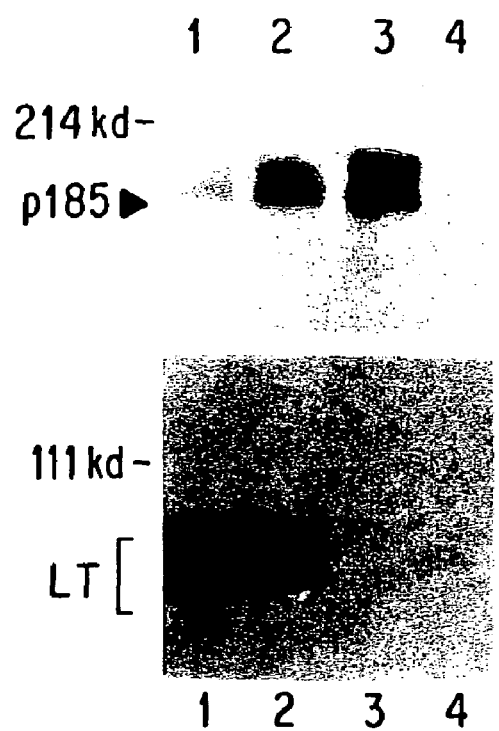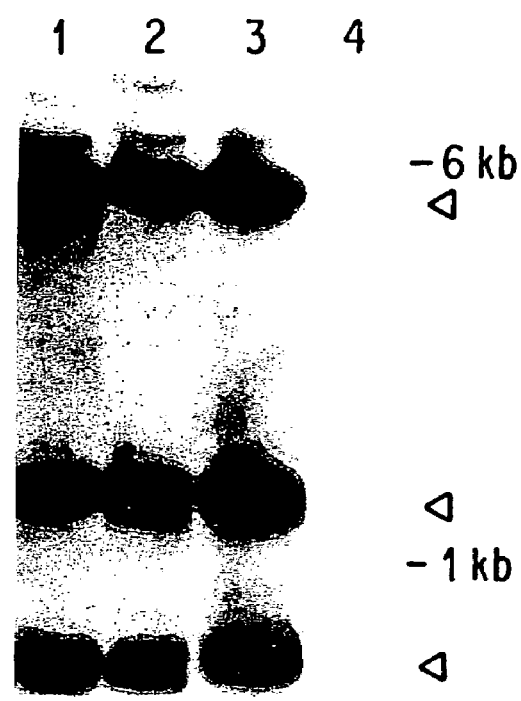
FIG.15A
FIG.15B
FIG.15C

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
tcttgctgga atgcagttgg                                                      20
```

NUCLEIC ACID ENCODING AN E1A GENE PRODUCT SENSITIZES HER-2/NEU OVEREXPRESSING CANCER CELLS TO CHEMOTHERAPY

This application is a continuation of Ser. No. 08/809,021 filed Mar. 19, 1997 now U.S. Pat. No. 6,395,712, which claims benefit of Provisional Application No. 60/013,750, filed Mar. 20, 1996.

BACKGROUND OF THE INVENTION

A. Field of the Invention

The present invention relates to methodology and associated genetic constructs for the suppression of oncogene-mediated, transformation, tumorigenesis and metastasis. In particular, this invention relates to the suppression of oncogenesis that is mediated by the HER-2/c-erb B-2/neu oncogene, an oncogene which has been correlated with a poor prognosis of breast and ovarian carcinoma in humans.

B. Background of the Related Art

During the last decade, a number of human malignancies have been discovered to be correlated with the presence and expression of "oncogenes" in the human genome. More than twenty different oncogenes have now been implicated in tumorigenesis, and are thought to play a direct role in human cancer (Weinberg, 1985). Many of these oncogenes apparently evolve through mutagenesis of a normal cellular counterpart, termed a "proto-oncogene", which leads to either an altered expression or activity of the expression product. There is considerable data linking proto-oncogenes to cell growth, including their expression in response to certain proliferation signals (see, e.g., Campisi et al., 1983) and expression during embryonic development (Muller et al., 1982). Moreover, a number of the proto-oncogenes are related to either a growth factor or a growth factor receptor.

The c-erbB gene encodes the epidermal growth factor receptor (EGFr) and is highly homologous to the transforming gene of the avian erythroblastosis virus (Downward et al., 1984). The c-erbB gene is a member of the tyrosine-specific protein kinase family to which many proto-oncogenes belong. The c-erbB gene has recently been found to be similar, but distinct from, an oncogene referred to variously as c-erbB-2, HER-2 or neu oncogene (referred to herein simply as the neu oncogene), now known to be intimately involved in the pathogenesis of cancers of the human female breast and genital tract.

The neu oncogene, which encodes a p185 tumor antigen, was first identified in transfection studies in which NIH 3T3 cells were transfected with DNA from chemically induced rat neuroglioblastomas (Shih et al., 1981). The p185 protein has an extracellular, transmembrane, and intracellular domain, and therefore has a structure consistent with that of a growth factor receptor (Schechter et al., 1984). The human neu gene was first isolated due to its homology with v-erbB and EGF-r probes (Senba et al., 1985).

Molecular cloning of the transforming neu oncogene and its normal cellular counterpart, the neu proto-oncogene, indicated that activation of the neu oncogene was due to a single point mutation resulting from one amino acid change in the transmembrane domain of the neu encoded p185 protein (Bargmann et al., 1986; Hung et al., 1989).

The neu oncogene is of particular importance to medical science because its presence is correlated with the incidence of cancers of the human breast and female genital tract. Moreover, amplification/overexpression of this gene has been directly correlated with relapse and survival in human breast cancer (Slamon et al., 1987). Therefore, it is an extremely important goal of medical science to evolve information regarding the neu oncogene, particularly information that could be applied to reversing or suppressing the oncogenic progression that seems to be elicited by the presence or activation of this gene. Unfortunately, little has been previously known about the manner in which one may proceed to suppress the oncogenic phenotype associated with the presence of oncogenes such as the neu oncogene.

An extensive body of research exists to support the involvement of a multistep process in the conversion of normal cells to the tumorigenic phenotype (see, e.g., Land et al., 1983). Molecular models supporting this hypothesis were first provided by studies on two DNA tumor viruses, adenovirus and polyomavirus. In the case of adenovirus, it was found that transformation of primary cells required the expression of both the early region 1A (EA) and 1B (E1B) genes (Houweling et al., 1980). It was later found that the E1A gene products could cooperate with middle T antigen or with activated H-ras gene to transform primary cells (Ruley, 1985). These observations suggested that the involvement of multiple functions in the transformation process, and that various oncogenes may express similar functions on a cellular level.

The adenovirus E1A gene codes for several related proteins to which a number of interesting properties have been attributed. In addition to its ability to complement a second oncogene in transformation, a closely related function allows E1A to immortalize primary cells (Ruley, 1985). For example, introduction of E1A gene products into primary cells has been shown to provide these cells with an unlimited proliferative capacity when cultured in the presence of serum.

Another interesting action of E1A function is so-called "trans-activation", wherein E1A gene products stimulate transcription from a variety of viral and cellular promoters, including the adenovirus early and major late promoter. However, trans-activation is not universal for all promoters. In some instances, E1A causes a decrease in transcription from cellular promoters that are linked to enhancer elements (Haley et al., 1984). Recently, it has been shown that exogenously added E1A gene can reduce the metastatic potential of ras-transformed rat embryo fibroblast cells by activating the cellular NM23 gene that is associated with a lower metastatic potential (Pozzatti et al., 1988; Wallich et al., 1985).

The E1A gene products are referred to as the 13S and 12S products, in reference to the sedimentation value of two mRNAs produced by the gene. These two mRNAs arise through differential splicing of a common precursor, and code for related proteins of 289 and 243 amino acids, respectively. The proteins differ internally by 46 amino acids that are unique to the 13S protein. A number of E1A protein species can be resolved by PAGE analysis, and presumably arise as a result of extensive post-translational modification of the primary translation products (Harlow et al., 1985).

Another viral oncoprotein, the SV 40 large T antigen (LT) shares structural and functional homology to E1A and c-myc (Figge et al, 1988). LT, E1A and c-myc have transforming domains which share amino acid sequence homology and similar secondary structure (Figge et al., 1988). All three proteins complex with the tumor suppressor, retinoblastoma gene product (Rb) (Whyte et al., 1988, DeCaprio et al., 1988, Rustgi et al., 1991), and the Rb binding domains of LT and E1A coincide with their transforming domains. Based on this similarity, it has been thought that LT and E1A transform cells by binding cellular Rb and abrogating its tumor suppressor function. LT, E1A and c-myc are also grouped as immortalization oncogenes as determined by the oncogene cooperation assay using rat embryo fibroblasts (Weinberg, 1985).

In spite of the similarity between the Rb binding domains of LT and E1A, the two proteins differ substantially in other regards. In fact, there is apparently only a short equivalent stretch of acidic amino acids (Figge et al., 1988). This stretch lies between amino acids 106–114 in LT and amino acids 121–139 in E1A. The large T antigen is encoded by the simian virus 40, a member of the polyoma virus family. In contrast, E1A is encoded by adenovirus 5 virus, which is a member of the adenovirus family. LT is 708 amino acids long, while E1A is substantially shorter at 298 amino acids. LT has been observed to bind directly to certain DNA sequences, however, E1A has not. LT binds with the tumor suppressors Rb and also with p53. E1A complexes with Rb but not with p53. E1A has been shown to induce apoptosis in cells, this has not been demonstrated for LT.

Further, LT is an apparent anomaly in the scheme of oncogenic classification. Oncogenes are typically classified as being cytoplasmic or nuclear oncogenes. However, LT, through the actions of a single protein, is able to introduce "nuclear" characteristics such as immortalization and "cytoplasmic" characteristics such as anchorage independence in cells (Weinberg, 1985). LT antigen can be found in both the nucleus and at the plasma membrane, and mutations that inhibit the transport of LT into the nucleus appear to reduce its immortalizing ability while leaving intact its effect on anchorage independence and its ability to transform already immortalized cells. Consequently, this oncogene is considered to be a member of both the nuclear and cytoplasmic oncogenic classes, since it sends its gene product to do work at two distinct cellular sites (Weinberg, 1985). In contrast, E1A is known as a nuclear oncogene only.

Despite advances in identifying certain components which contribute to the development of malignancies, it is clear that the art still lacks effective means of suppressing carcinogenesis. For example, there is as yet no particularly successful way of suppressing neu oncogene activation or the development of various cancers, such as those of the breast and genital tract, which are associated with this molecular event.

SUMMARY OF THE INVENTION

The present invention seeks to overcome these and other drawbacks inherent in the prior art by providing methods for the suppression of neu-mediated oncogenesis. Certain aspects of the present invention relate to the inventors' surprising discovery that, in contrast to previous characterizations of the E1A gene and the LT gene as being involved in promoting transformation, the E1A and LT gene products can actually serve to suppress not only the expression of the neu oncogene, but suppress the oncogenic phenotype which accompanies neu oncogene activation. Furthermore these gene products sensitize cancer cells to chemotherapeutic agents. It is proposed that this exciting discovery opens the door to novel approaches to the treatment of neu oncogene-mediated cancers, as well as an improved understanding of the regulation of this oncogene in particular and the oncogenic phenotype in general.

The present invention thus arises out of the inventors' surprising discovery that products of the adenovirus E1A gene, a gene that is itself known to serve as an oncogene, can be effectively employed to suppress the transforming capability of the neu oncogene and sensitize chemoresistant cancer cells to chemotherapeutic regimens. Accordingly, the invention can be characterized in a general sense as relating to a method of treating neu oncogene-mediated transformation of a cell, which method includes introducing an E1A gene product into such a cell in a manner that is effective to suppress an oncogenic phenotype, as indicated by a reduction in transforming, tumorigenic or metastatic potential of the cell. Further the introduction of the E1A gene product into the cell sensitizes it to conventional chemotherapeutic agents. Hence gene therapy is used in conjunction with chemotherapy to effectively kill the cancer.

The invention also arises out of the inventors' surprising showing that introduction of LT antigen into cells leads to a significant decrease in the expression of neu encoded p185 and also sensitizes neu-overexpressing cells to chemotherapeutic agents. LT, like E1A and c-myc, represses the upstream regulatory sequences of neu. However, LT represses a different region of the neu regulatory sequences compared to E1A and c-myc, suggesting LT affects neu expression through a different pathway.

Thus the present invention, in a general and overall sense, concerns methods of inhibiting oncogene-mediated transformation of a cell and sensitizing the cell to chemotherapeutic agents using gene products. These methods involve contacting the cell with a neu-suppressing gene product and a chemotherapeutic drug in amounts effective to inhibit the transformed phenotype.

The objects of the invention may be achieved by introduction of E1A gene products or LT intracellularly in any convenient manner, including, for example, virus mediated gene transfer, DNA transfection via calcium phosphate or liposome methods, and even direct introduction of gene products by microinjection. It is proposed that methods such as these will work adequately, e.g., where one is seeking to study neu oncogene suppression. However, where a treatment regimen is contemplated it will likely be necessary to introduce the selected E1A gene product or LT by intracellular introduction of a DNA segment which encodes the particular domain of the E1A protein or LT that is required for repression of neu.

In any event, since the E1A gene products have been extensively characterized, and the gene itself has been cloned (see, e.g., Berk et al., 1978), the starting materials, i.e., the E1A products and gene, are readily available to those of skill in the art who desire to practice the invention.

LT is also characterized and the gene has been cloned. The entire SV40 nucleotide sequence is disclosed in the book *Molecular Biology of Tumor Viruses*, Part 2, 2d. ed., Tooze, J., Cold Spring Harbor Laboratory, Cold Spring Harbor, N.Y. (1981), Appendix A, pgs. 799–813. In addition to the genomic sequence, *Molecular Biology of Tumor Viruses* contains a map of SV40 landmarks including the location of the large T antigen within the SV40 genome [pg. 813]. The references Fiers et al., 1978 and Reddy et al., 1978 also report the genetic sequences of SV40. The amino acid sequence of LT can be found in *Molecular Biology of Tumor Viruses*, pgs. 854 and 857–861. Various mutant of native LT have been described. For example, Kalderon et al. (1984) describe many LT mutations, which were the result of deletion and point mutations of the native LT gene. The relevant amino acid sequences of each LT mutant reported in Kalderon et al. are contained in Table 2 of that reference. By combining the information in Kalderon et al (1984) with the sequence information for native LT contained in *Molecular Biology of Tumor Viruses*, the sequence for any of these mutants can be determined. All of the genomic and amino acid sequences of native LT and LT mutants contained in the references cited in this paragraph are incorporated by reference in this specification.

Some embodiments of the invention involve methods of inhibiting oncogene-mediated transformation of a cell. Generally, these methods comprise the step of contacting the cell with an oncogenic phenotype suppressing gene product and a chemotherapeutic drug in amounts effective to inhibit the transformed phenotype. In a preferred embodiment, the oncogene-mediated transformation being inhibited will be neu oncogene-mediated transformation. Also, preferably, the embodiments in which transformation is to be inhibited will comprises a tyrosine specific protein kinase encoded by neu. Of course, the invention also applies to methods of inhibiting other oncogene-mediated transformation events, such as transformation by ras, src, yes, fps, fes, abl, ros, fgr, erbB, fms, mos, raf, etc.

Embodiments of the present invention involve chemotherapeutic agents. These are compounds that exhibit some form of anti-cancer activity. In some preferred embodiments, the chemotherapeutic drug is an alkylating agent, plant alkaloid, antibiotic, or antineoplastic agent. In those embodiments of the invention where the chemotherapeutic is an alkylating agent, the alkylating agent may be, for example, mechlorethamine, cyclophosphamide, ifosfamide chiorambucil, melphalan, busulfan, thiotepa, carmustine, lomustine, and/or shreptozoin. In those embodiments where the chemotherapeutic agent comprises a plant alkaloid, the plant alkaloid is, for example, vincristine, vinblastine or taxol. In a preferred embodiment, the plant alkaloid is taxol. In those embodiments of the invention where the chemotherapeutic agent is an antibiotic, the antibiotic may be, for example, dactinomycin, daunorubicin, idarubicin, bleomycin mitomycin or doxorubicin. In most preferred embodiments the antibiotic is doxorubicin. In other embodiments where the chemotherapeutic agent comprises an antineoplastic, the preferred antineoplastic is, for example, cisplatin, VP16 and TNF.

In certain embodiments of the invention, the E1A or LT is administered to the cell prior to the administration of the chemotherapeutic agent. In other aspects of the invention, the chemotherapeutic agent is administered to the cell prior to administration of the E1A or LT. Alternatively the E1A or LT and the chemotherapeutic drug are administered simultaneously.

In some embodiments of the invention, the cell is located within an animal and effective amounts of the E1A or LT and the chemotherapeutic drug are administered to the animal. In certain embodiments of the invention, the chemotherapeutic drug and the E1A or LT are suitably dispersed in a pharmacologically acceptable formulation. In certain preferred embodiments where the cell is an animal cell, the animal cell is a human cell. In other preferred embodiments the cells is a lung, cancer cell, ovarian cancer cell, or a breast cancer cell.

In some embodiments of the present invention the cell is contacted with a single composition comprising the E1A or LT in combination with a chemotherapeutic agent. In such cases, the composition may be suitably dispersed in a pharmacologically acceptable formulation.

The invention contemplates embodiments comprising sensitizing a cancer cell to a chemotherapeutic drug. These embodiments comprise exposing the cell with an effective amount of the E1A or LT. In some such embodiments inhibition of neu-mediated cancer is accomplished by administrating an effective combination of the E1A or LT and chemotherapeutic drug to an animal having or suspected of having cancer in an effective amount to inhibit the cancer. In embodiments where the composition is administered to an animal, the animal is typically a mammal. In such cases, the invention will be of particular use in the treatment and prevention of neu-mediated transformation in humans Certain embodiments of the present invention comprise injecting a therapeutically effective amount of the E1A or LT into an animal and contacting the animal with a chemotherapeutic drug. In certain embodiments of the invention the cancer site is contacted with a chemotherapeutic drug by administering to the animal a therapeutically effective amount of a pharmaceutical composition comprising a chemotherapeutic drug wherein the chemotherapeutic drug is for example cisplatin, doxorubicin, VP16, taxol or TNF.

The inventors have also enabled the production of pharmaceutical compositions comprising an E1A or LT and a chemotherapeutic drug in a pharmacological carrier. Those of skill will understand the nature of such pharmacological carriers based on the teachings of this specification and the current knowledge in the art. The pharmaceutical compositions of the invention may contain any of the E1A or LT and chemotherapeutic drugs mentioned above or elsewhere in this specification, or know to those of skill in the art. They may also contain emodin and/or an emodin like compound. In a preferred pharmaceutical composition the chemotherapeutic drug is cisplatin, doxorubicin, etoposide, taxol or TNF. In some preferred embodiments, the neu-suppressing gene product is E1A. In some preferred embodiments the neu-suppressing gene product is LT.

The invention also encompasses pharmaceutical combinations comprising an a neu-suppressing gene product and a chemotherapeutic drug. In certain preferred combinations, the neu-suppressing gene product is E1A. In certain other preferred combinations, the neu-suppressing gene product is LT. The chemotherapeutic drug may be any that is listed elsewhere in this specification or known to those of skill in the art at the present or in the future. Exemplary chemotherapeutic drugs for us in the pharmaceutical combinations of the present invention are cisplatin, doxorubicin, etoposide, emodin and or emodin like compounds, taxol and TNF. In certain embodiments of the invention the pharmaceutical combination may contain the E1A or LT and the chemotherapeutic drug within the same pharmaceutical composition. In other embodiments, the pharmaceutical combinations will comprise separate pharmaceutical compositions for each of the E1A or LT and the chemotherapeutic drug. These separate compositions may be combined internal to or external to a body to create the pharmaceutical combination.

Other embodiments of the invention include therapeutic kits comprising in suitable container, a pharmaceutical formulation of an the E1A or LT preparation, a pharmaceutical formulation of a chemotherapeutic drug, and/or a pharmaceutical formulation comprising both the E1A or LT and a chemotherapeutic drug. Emodin and/or emodin like compounds may also be present in the kit either in combination with the gene products, chemotherapeutic agent, gene products and chemotherapeutic agent or indeed in a separate formulation. The kit may also contain instructions on how to administer the pharmaceutical formulation or formulations of the kit to an animal either alone, or in combination with formulations that one may obtain separately from the kit. The kit may also comprise instructions that explain how to use the kit but are provided separately from the container of the kit. The kit may comprise the E1A or LT, emodin and/or emodin like compound, and chemotherapeutic drug to be present within a single container or alternatively the kit could comprise the E1A or LT and/or emodin and the chemotherapeutic drug are present within distinct containers.

Some embodiments of the present invention relate to a method of sensitization of a cell to an anticancer drug, comprising contacting the cell with the E1A or LT. These gene products are well-described in this specification. In preferred embodiments the oncogene-mediated transformation is neu oncogene-mediated transformation. Also, preferably, the embodiments in which transformation is to be inhibited will comprises a tyrosine specific protein kinase encoded by neu. The invention also contemplates pharmaceutical compositions, and kits comprising the E1A or LT to suppress neu-mediated transformation. Of course, the invention also applies to methods of inhibiting or suppressing other oncogene-mediated transformation events, such as transformation by ras, src, yes, fps, fes, abl, ros, fgr, erbB, fms, mos, raf.

Emodin-like tyrosine kinase inhibitors of the invention are those compounds that exhibit similar characteristics to those of emodin with regard to tyrosine kinase inhibition and the inhibition of neu-mediated transformation. Of course the invention is not limited to the use of these inhibitors and other inhibitors that possess the structural and/or functional properties of emodin may be used. In some preferred embodiments, the emodin-like tyrosine kinase inhibitor is an anthraquinone-like tyrosine kinase inhibitor. The emodin-like tyrosine kinase inhibitor may be, for example, emodin, emodin-8-O-D-glucoside, chrysophanic acid, glucochrysophanic acid, physcion, or physcion-8-O-D-glucoside. In the most preferred embodiment the neu tyrosine kinase inhibitor is emodin.

Other embodiments of the present invention relate to a method of inhibiting oncogene-mediated transformation of a cell, comprising contacting the cell with the E1A or LT, further contacting the cell with emodin and/or an emodin-like compound and further still contacting the cell with the chemotherapeutic agent. The cell may be contacted with the gene product, the emodin and/or emodin like compound and the chemotherapeutic agent successively in any order. Alternatively the cell is contacted with a combination of gene product and emodin, gene product and chemotherapeutic drug, emodin and chemotherapeutic drug followed or preceded by treatment of the third agent. In yet another embodiment it is possible to contact the cell with the gene product, emodin and/or emodin like compound and chemotherapeutic agent concurrently with each other.

In some embodiments of this invention an a cell is contacted with between about 0.5 mg/kg total weight and 500 mg/kg total weight of the emodin-like tyrosine kinase inhibitor. Other embodiments wherein the cell is contacted with between about 0.5 mg/kg total weight and 500 mg/kg total weight of emodin. In still other embodiments the cell is contacted with between about 0.5 mg/kg total weight and 500 mg/kg total weight of an emodin-like tyrosine kinase inhibitor. Total weight may be defined as the total weight of the cell or cells in culture, or the body weight of an animal, including a human.

The present invention also contemplates compositions comprising a liposomal complex. This liposomal complex will comprise a lipid component and a DNA segment encoding a neu-suppressing gene. The neu-suppressing gene employed in the liposomal complex can be, for example, an LT gene or an E1A gene. Liposomal complexes comprising LT mutants may have certain advantages. These advantages may be particularly distinct when the LT gene encodes non-transforming LT mutant, such as K1. An E1A gene encoding either the E1A 12S or E1A 13S gene product, or both, may be complexed with a lipid to form the liposomal complex.

The lipid employed to make the liposomal complex can be any of the above-discussed lipids. In particular, DOTMA, DOPE, and/or DC-Chol may form all or part of the liposomal complex. The inventors have had particular success with complexes comprising DC-Chol. In a preferred embodiment, the lipid will comprise DC-Chol and DOPE. While any ratio of DC-Chol to DOPE is anticipated to have utility, it is anticipated that those comprising a ratio of DC-Chol:DOPE between 1:20 and 20:1 will be particularly advantageous. The inventors have found that liposomes prepared from a ratio of DC-Chol:DOPE of about 1:10 to about 1:5 have been useful in the studies they have performed. In most studies, the inventors have used a ratio of 1.2 $\mu$mol DC-Chol:8.0 $\mu$mol DOPE.

The present invention also comprises kits for the introduction of a neu-suppressing gene product into a cell comprising a neu-suppressing DNA/liposome complex.

BRIEF DESCRIPTION OF THE DRAWINGS

The following drawings form part of the specification and are included to further demonstrate certain aspects of the present invention. The invention may be better understood by reference to one or more of these drawings in combination with the detailed description of specific embodiment presented herein.

FIG. 1A transcriptional repression of neu promoter by E1A gene products. Rat-1 cells were transfected with 5 $\mu$g of the pNeu-EcoR1-CAT construct, which contains the CAT gene driven by neu oncogene promoter containing 2.2-kb upstream DNA sequences. Lane 1, basal neu promoter activity (its relative CAT activity is defined as 100%); lanes 2–4, CAT activity after cotransfection with 10 $\mu$g of carrier DNA pSP64 vector (102%, lane 2); E1A-expressing plasmid pE1A (34%, lane 3); pE1Apr, a plasmid containing only the E1A promoter (98%, lane 4). The CAT activities of a reporter plasmid, RSV-CAT, containing the CAT gene under the control of RSV LTR (10%, lane 5) were not significantly changed by cotransfection of 10 $\mu$g of pE1A (98%, lane 6) or 20 $\mu$g of pE1A (96%, lane 7).

FIG. 1B shows the effect of various adenovirus early genes on neu promoter activity. The pneuEcoRI-CAT was cotransfected with pSP64 vector or plasmid expressing various adenovirus early genes, E1A, E1B, E2A, and E3, as indicated. The relative CAT activities are as follows: SP64, 100%; E1A, 35%, E1B, 97%, E2A, 99%, E3, 102%. RSV-CAT was used as a positive control.

FIG. 3A depicts schematic maps of the neu promoter 5' deletion constructs that were fused individually to the CAT gene to create the plasmids as indicated by the names of the restriction enzymes used for generating the constructs.

FIG. 3B illustrates the level of expression of the CAT gene directed by each of the promoter fragment constructs after transfection of 5 µg of the plasmids into Rat-1 cells with 10 µg of cotransfected pE1A (E) or carrier DNA pSP64 (C). The names of restriction enzymes above each triplet assay refer to the constructs indicated in the maps.

FIG. 4A. Rat-1 cells were transfected with 5 µg of the pNeuEcoR1-CAT plasmids giving basal neu promoter activity (lane 1); the repressed CAT activity after cotransfection with 5 µg of the pE1A is shown in lane 2. Plasmids pSP64/Stu-Xho containing the Stu I-Xho I neu promoter fragment cloned in pSP64 were cotransfected with pneuEcoR1-CAT and pE1A. Lanes 3–6 show the competitive effects of increasing amounts (5, 10, 15, and 20 µg, respectively) of pSP64/Stu-Xho. Plasmids pSP64/R1-Xba containing the EcoRI-Xbu I neu promoter fragment were also cotransfected with pneuEcoR1-CAT and pE1A. Lanes 7–9 show CAT activities from neu promoter by cotransfecting 5, 10, and 20 µg of pSP64/RI-Xba, respectively. The relative CAT activities of lanes 1–9 are as follows: 100%, 32%, 27%, 31%, 58%, 79%, 38%, 31%, 24%.

FIG. 4B shows immunoblot for p185 protein in the cell lysates of SK-BR-3 breast cancer cells transfected by pneuEcoRV-CAT. Seventy-five micrograms of protein from each sample was electrophoresed on 7% SDS/PAGE gels prior to transfer on nitrocellulose. Filters were blotted with the primary antibody mAb-3. Lane 1, lysates of SK-BR-3 cells transfected with 5 µg of pE1A; lane 2, cotransfected with 5 µg E1A and 20 µg of pSP64/RI-XbaI; lane 3, cotransfected with 5 µg of E1A and 20 µg of pSP64/Stu-Xho; lane 4, lysates of SK-BR-3 cells after mock transfection. The protein size marker is shown on the right. The arrow indicates the position of p185 protein. The p185 protein bands were scanned by Bio-Rad video densitometer model 620 to determined the relative p185 protein level. The p185 protein level in the mock transfection sample is defined as 100% and the relative amounts of p185 proteins in lanes 1–3 are 57%, 54%, and 89%, respectively.

FIG. 6A shows southern blot analysis of NIH3T3, B104-1-1 and their transfectants using an EcoRI-SstI E1A DNA probe. 10 µg of genomic DNA from the indicated cell lines were digested to completion with EcoRI+SstI restriction endonucleases and subjected to electrophoresis on a 1% agarose gel. The DNAs were transferred to Nitran™ filter paper and hybridized with the E1A probe. The DNA markers are shown on the left.

FIG. 6B shows immunoblot analysis for E1A proteins in the cell lysates of the indicated cell lines. 50 µg of each sample were electrophoresed on 10% SDS-PAGE prior to transfer to nitrocellulose. Filters were incubated with the primary antibody M73 against E1A. The protein molecular weight marker and the position of E1A proteins are shown on the right. 25 µg of Cell lysate from 293 cells was used as a positive control.

FIG. 6C Immunoblot analysis for the neu encoded p185 protein in the cell lysates of the indicated cell lines. The studies were performed as described in section (FIG. 6B) above. The primary antibody was mAB-3 against p185, purchased from Oncogene Science Inc.

FIG. 6D Southern blot analysis of the indicated cell lines using rat neu DNA probe. The studies were performed as described in FIG. 6A above. The DNAs were digested with Bam HI restriction endonuclease.

(FIG. 7A) B104-1-1; (FIG. 7B) B-E1Apr; (FIG. 7C) N-E1A-1; (FIG. 7D) B-E1A-1; (FIG. 7E) B-E1A-2; (FIG. 7F) B-E1A-3 (Magnification: x130).

FIG. 8A [$^3$H] Thymidine incorporation of the indicated cell lines. $9 \times 10^3$ cells were plated in 96 well multiwell plates and cultured in Dulbecco's modified Eagle medium supplemented with 10% calf serum for 16, 40 and 64 hrs. Cell received a 2 hr pulse of 1 µCi [$^3$H]-thymidine per well to label those that were synthesizing DNA prior to harvest. Radioactivities of individual samples were counted by scintillation counter. Average cpm counts were calculated from replicated samples.

FIG. 8B. Anchorage independent growth of E1A-transfected B104-1-1 and NIH3T3 cells. $1 \times 10^3$ cells were plated in 0.35% soft agar over a 0.7% agar lower layer. Colonies were counted after 4 weeks. A typical plate and the mean of triplicate samples plus or minus the standard error of the mean are shown for each group.

FIG. 9A Summary of tumorigenicity of B104-1-1, NIH3T3 and their transfectant. $1 \times 10^5$ viable cells were injected subcutaneously into right and left flanks of female homozygous nu/nu mice, respectively. Tumor formation was scored at indicated days as presence or absence of a visible tumor mass. 16 days after injection, tumor volumes were estimated as the product of tri-dimensional caliper measurements (longest surface length and width, and tumor thickness). N.D.: not detectable at the time of evaluation.

FIG. 9B. A representative result of tumorigenicity study. From right to left: the animals were injected with B104-1-1, B-E1A-2 or NIH3T3 cells 18 days prior to the photographing data.

FIG. 10A E1A gene products inhibited the cell motility of the neu-transformed 3T3 cells. N-E1A: NIH3T3 cells transfected with E1A; B-neo: B104-1-1 cells transfected with neomycin resistant gene; B-E1A-1 to 5: five independent cell lines generated by transfecting E1A gene into B104-1-1 cells. The motility assays were carried out by using a transwell unit with 5 µm pore size polycarbonate filter in 24 well cluster plate (Costar). Lower compartment of the transwell contained 600 µl of one of the chemoattractants: 20 µm fibronectin (FN) or 100 µm FN dissolved in DMEM/F12, or hepatic endothelial cell conditioned media (HSE), or DMEM/F12 medial only as negative control. The cells ($3 \times 10^4$/0.1 ml in DMEM/F12) were plated in the upper compartment and incubated for 6 hrs. at 37° C. in a humidified 5% $CO_2$ atmosphere. After the incubation, the filters were fixed with 3% glutaraldehyde in PBS buffer and stained with Geimsa. Each sample was assayed in triplicate and cell motility was measured by counting the number of cells that had migrated to the lower side of the filter. At least four HPFs were counted per filter. The number of cells migrated to DMEM/F12 has been deducted from each sample to eliminate the background and all the assays were done in triplicates.

FIG. 10B shows E1A gene products inhibited the invasiveness of the neu-transformed 3T3 cells. The assay of in vitro invasiveness was done basically as described by Albini et al, 1987 and Repesh, 1989. The basement membrane preparation, matrigel, was purchased from Collaborative Research, Inc. Filters in the transwell unit (same as used in motility assay) were coated with 0.1 ml of 1:20 dilution of matrigel in DMDM/F12 media. Lower compartment contained 0.6 ml of HSE as chemoattractant or DMEM(F12 as negative control. The cells ($5 \times 10^4$/0.1 ml in DMEM/F12) were plated in upper compartment and incubated for 72 hrs. at 37° C. in a humidified 5% $CO_2$ atmosphere. Cells were fixed, stained and counted as described in 1.a. All the assays were done in triplicate and assays were repeated twice.

Figure 10A:
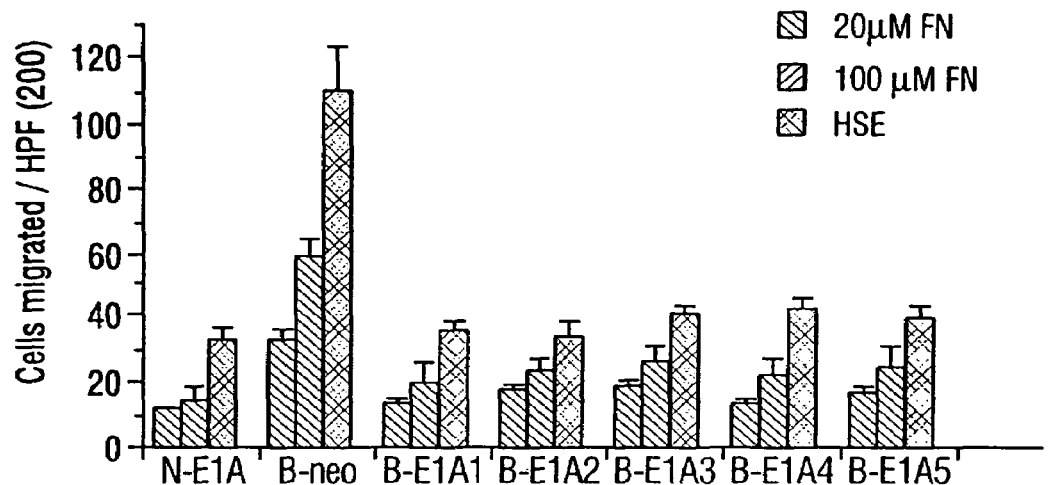
FIG. 10A, FIG. 10B and FIG. 10C, FIG. 10D, FIG. 10E, FIG. 10F show E1A inhibition of neu-transformed cells.
Figure 10B:
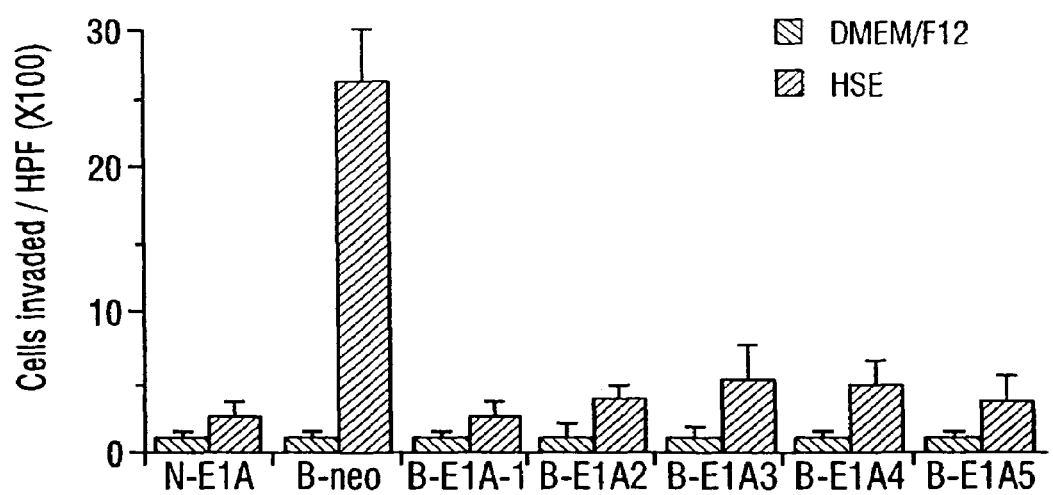
Figure 10C:
Figure 10D:
Figure 10E:
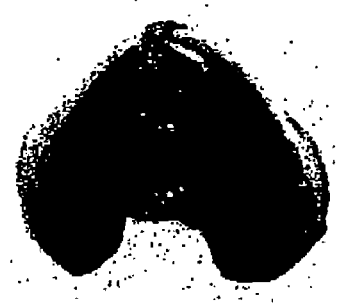
Figure 10F:

Gross appearance of lungs from the mice injected with B-neo cells (10C), N-E1A cells (10D), B-E1A-1 cells (FIG. 10E), and B-E1A-2 cells (FIG. 10F); E1A gene products inhibited the lung colonization of neu-transformed cells.

Figure 11A:
Figure 11B:
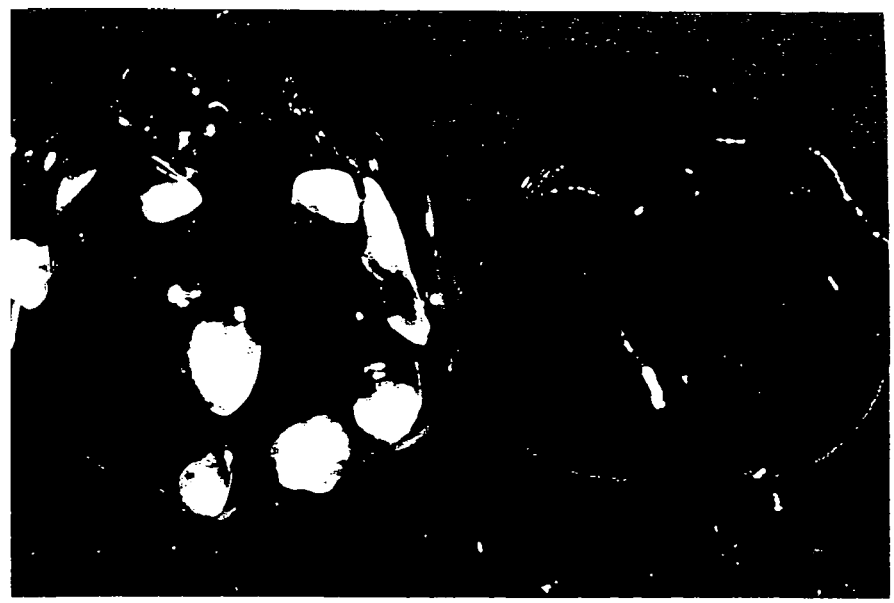

FIG. 11A and FIG. 11B show that E1A suppresses neu-induced tumor formation and metastasis in vivo in nude mice.

FIG. 11A Top, animal injected with B104-1-1 cells, a neu oncogene transformed NIH3T3 cell line; Bottom, animal injected with B-E1A2 cells, an E1A transfectant of B104-1-1. Photographs were taken 18 days after injection, and results are representative of other tumorigenicity studies.

FIG. 11B Left, gross appearance of lungs from mice injected with B104-1-1 cells; Right, gross appearance of lungs from mice injected with the E1A transfected cells, B-E1A2. Mice were inoculated with $1 \times 10^5$ cells/0.1 ml in PBS via the lateral tail vein at day 0, and were sacrificed 21 days after injection. The numbers of lung tumor nodules were determined following infiltration with India ink, only those lung nodules greater than 1 mm in diameter were counted in the assay.

Figure 12C:
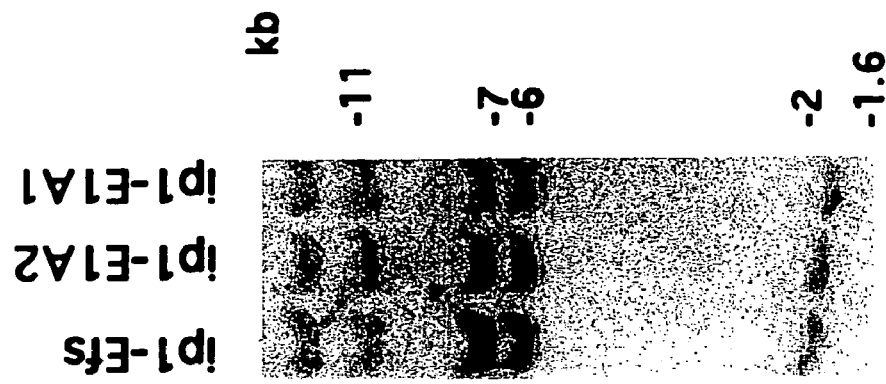
Figure 12B:
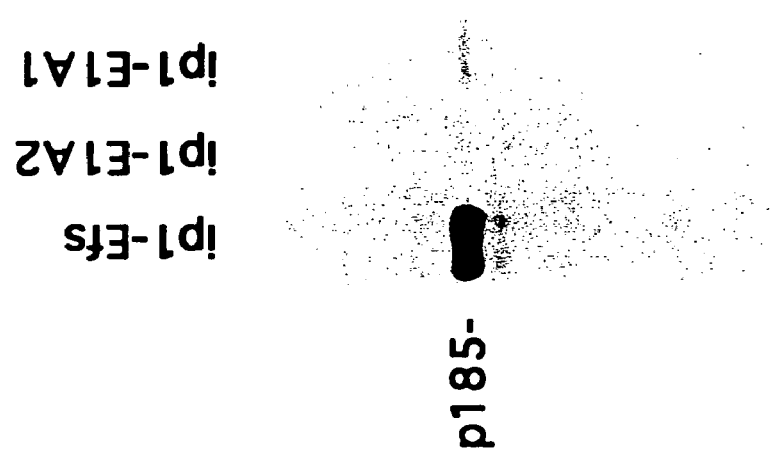
Figure 12A:
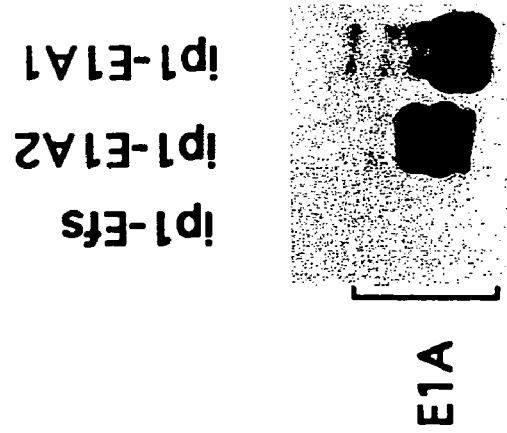

FIG. 12A–FIG. 12B FIG. 12C show the molecular characterization of the ip1, E1A and ip1.Efs transfectants described in Example V.

FIG. 12A shows immunoblot analysis of E1A proteins in the cell lysates of the indicated cell lines. Seventy-five mg of proteins from each sample were subjected to electrophoresis on 10% sodium dodecyl sulfate-polyacrylamide gel prior to transfer to nitrocellulose. Filters were incubated with the primary antibody M73, which recognizes E1A proteins. The position of the E1A proteins are indicated to the left of A.

FIG. 12B shows immunoblot analysis of the c-erbB-2/neu-encoded p185 proteins in the cell lysates of the indicated cell lines. Seventy-five mg of proteins from each sample were subjected to electrophoresis on 10% sodium dodecyl sulfate-polyacrylamide gel prior to transfer to nitrocellulose. Filters were incubated with the primary antibody c-neu-Ab-3 against p185. The position of the p185 proteins are indicated to the left of B.

FIG. 12C shows Southern blot analysis of DNAs from the ip1.E1A and ip1.Efs transfectants. Ten mg of genomic DNA from indicated cell lines were hybridized with the full-length c-erbB-2/neu cDNA probe. DNA markers are shown to the right.

Figure 13A:
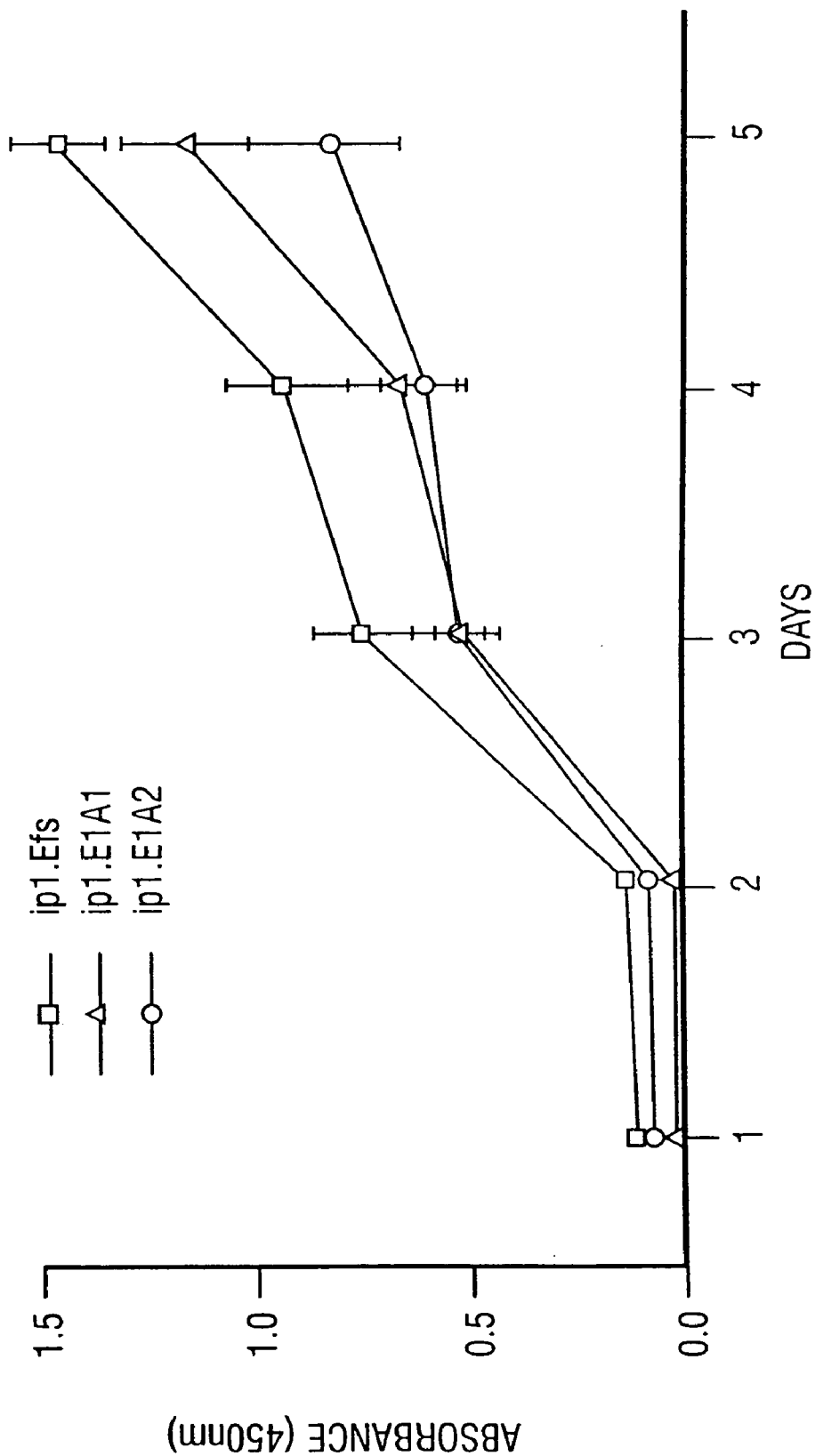
Figure 13B:
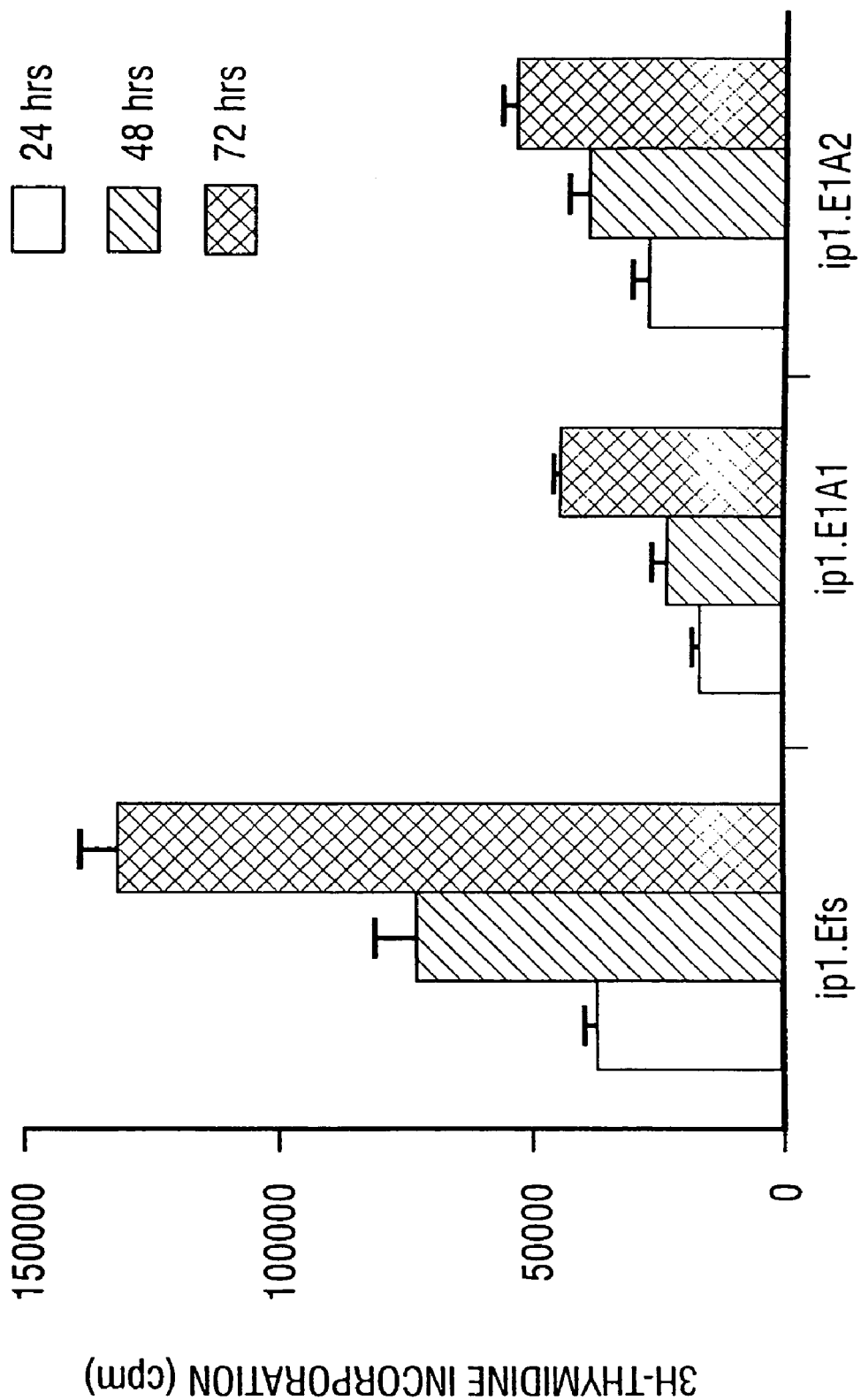

13A, FIG. 13B and FIG. 13 C show the reduced growth rate of the ip1.E1A transfectants versus control ip1.Efs cells, the decreased [$^3$H]thymidine Incorporation by the ip 1.E1A transfectants versus control ip1.Efs cells, and significantly inhibited colony formation for the ip1.E1A transfectants versus control ip1.Efs cells, respectively.

FIG. 13A shows reduced growth rate of the ip1.E1A transfectants versus control ip1.Efs cells. The in vitro growth rates of the cell lines were assessed by measuring increases in cell number with the MTT assay (Alley et al., 1988). Cells ($2 \times 10^3$/well) were plated in 96-well culture plates in 0.2 ml of culture medium. A total of 5 plates (9 wells/cell line/plate) were used. One of the plates was analyzed at 24-h intervals after the addition of 40 µl MTT (Sigma Chemical Co., St. Louis, Mo.) stock solution (1.25 mg MTT/ml of phosphate-buffered saline) to each well on the plate. Cells were incubated at 37° C. for 2.5 h, the medium was aspirated, and the cells were lysed in 100 µl of dimethyl sulfoxide. Conversion of MTT to formazan by metabolically viable cells was monitored by a Dynatech MR 5000 fluorescence microplate reader at a wavelength of 450 nm. Results were analyzed by regression analysis. Each study was repeated for each cell line at least twice.

FIG. 13B shows decreased [$^3$H]thymidine incorporation by the ip1.E1A transfectants versus control ip1.Efs cells. For this assay, 10 replicated cell samples were plated into 96-well plates at a density of $8 \times 10^3$ cells/well in culture medium. [$^3$H]Thymidine (1 µCi) was added to each well at 24, 48, and 72 h, respectively, with continuous incubation after each addition for 12 h at 37° C. Cells were harvested, and cellular DNA was bound to fiberglass filters. The radioactivity of each filter was counted with a scintillation counter. Average cpm were calculated from ten replicate samples.

FIG. 13C shows significantly inhibited colony formation for the ip1.E1A transfectants versus control ip1.Efs cells (P<0.01). Soft agar assays were performed as previously described (Matin et al., 1990). Cells ($1 \times 10^3$ cells/well) were plated in a 24-well plate in culture medium containing 0.35% agarose (BRL, Gaithersburg, Md.) overlying a 0.7% agarose layer. The cells were then incubated at 37° C. for 5 weeks, after which the plates were stained with p-iodonitrotetrazolium violet (1 mg/ml) for 48 h at 37° C. Colonies greater than 100 µm were counted for each dish and cell line. The numbers of soft agar colony are shown in the FIG. Studies were repeated four times for each cell line.

Figure 14A:
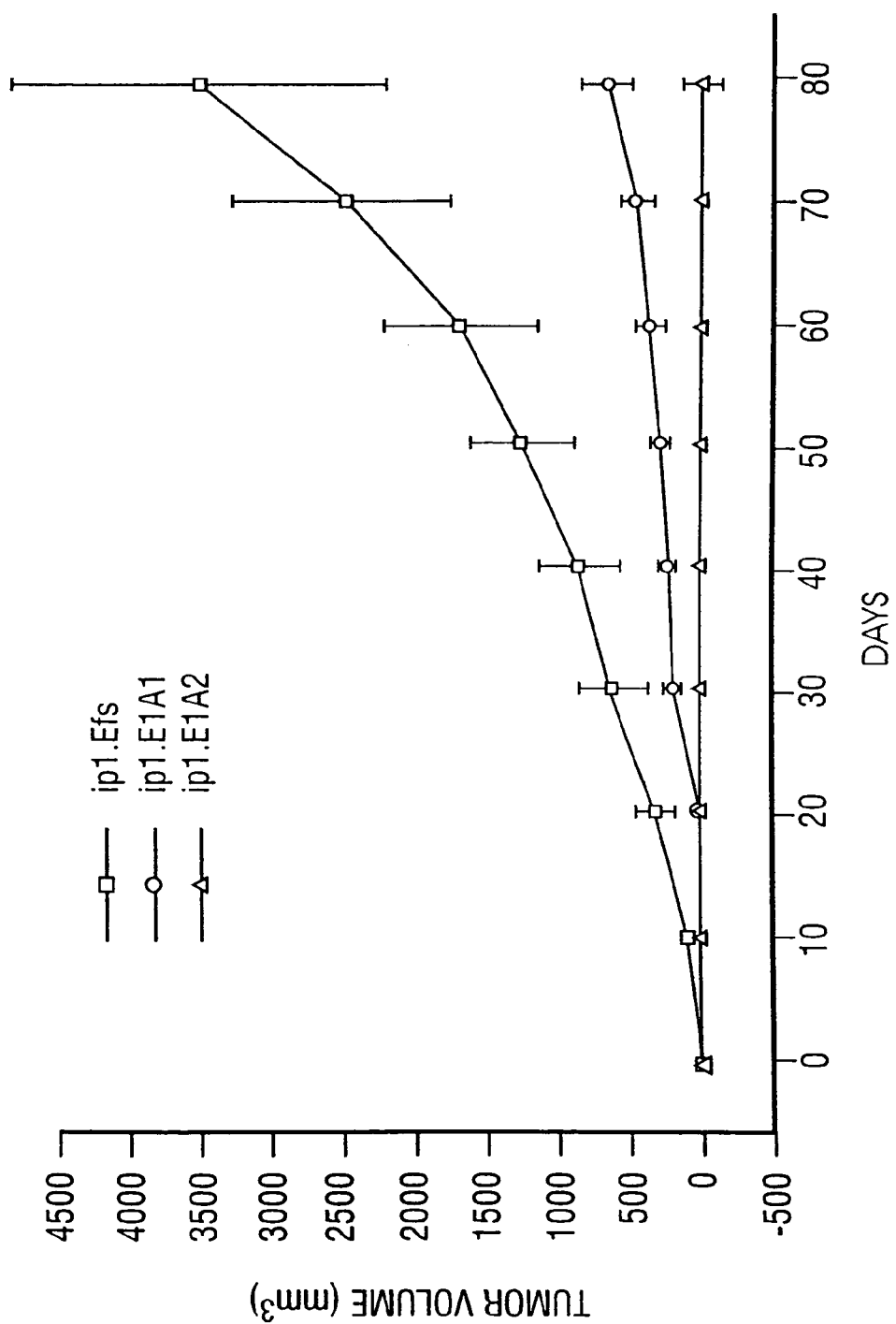
Figure 14B:
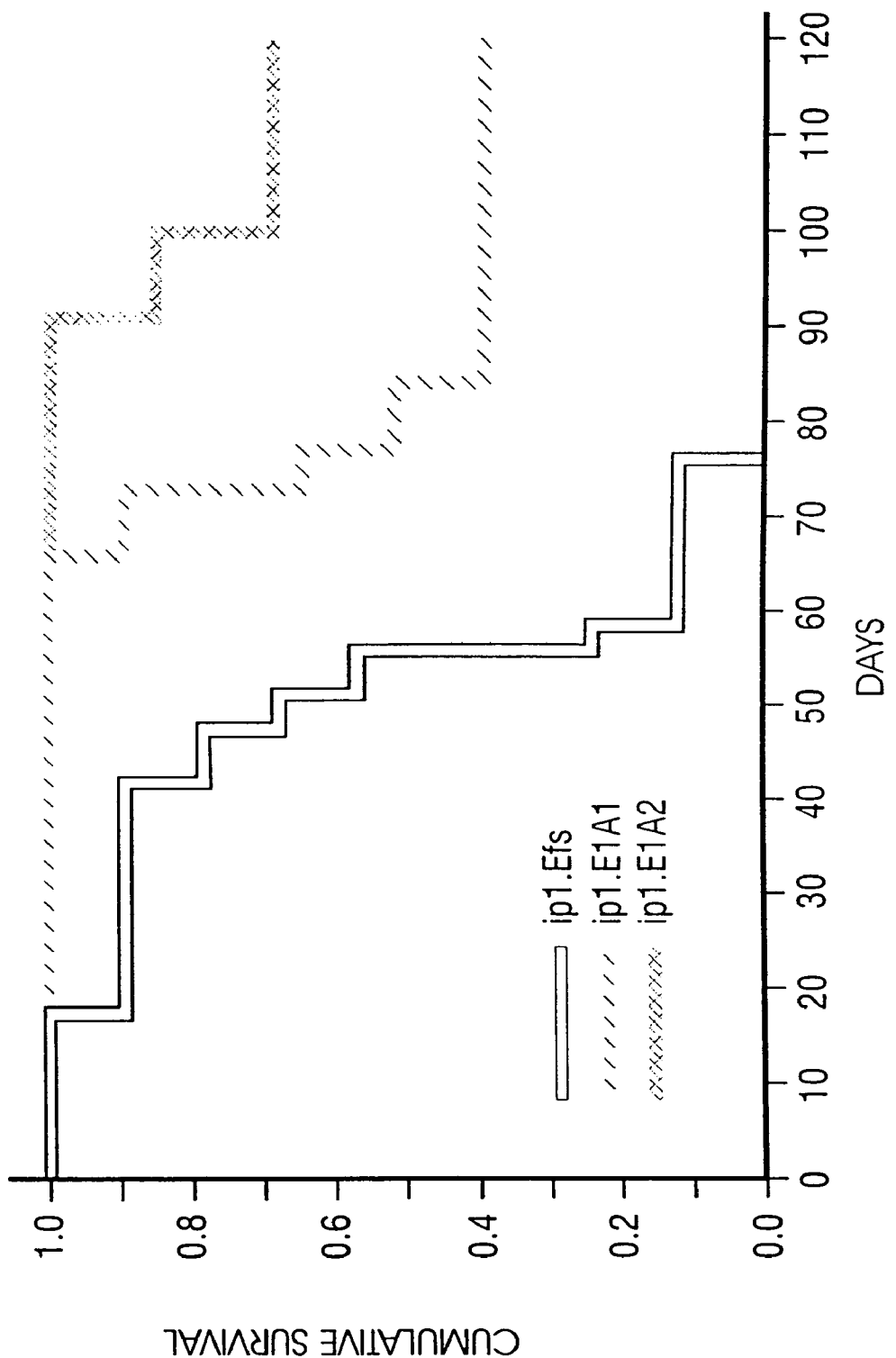

FIG. 14A and FIG. 14B show the E1A suppressed tumor formation by c-erbB2-/neu-overexpressing ovarian cancer cells and the longer survival of mice given injections of E1A-expressing ip1.E1A cells versus mice given injections of ip1.Efs human ovarian cancer cells.

FIG. 14A shows E1A suppressed tumor formation by c-erbB2-/neu-overexpressing ovarian cancer cells. Four- to 6-week-old athymic female homozygous nu/nu mice were purchased from the Animal Production Area, National Canter Institute-Frederick Cancer Research Facility (Frederick, Md.) or from Harlan Sprague Dawley, Inc., (Indianapolis, Ind.). The care and use of the animals was in accordance with institutional guidelines. For tumorigenicity assays, cells in log-phase growth were trypsinized, washed twice with phosphate-buffered saline, and centrifuged at 250×g. The viable cells were counted; of those, $3 \times 10^6$ cells in 0.1 ml of phosphate-buffered saline were injected s.c. into both the right and left flanks of female mice under aseptic conditions. Tumor volumes were estimated as the product of three-dimensional caliper measurements (longest surface length and width; tumor thickness). The growth of tumors was monitored for a minimum of 80 days and a maximum of 160 days, as shown by the days indicated in the FIG.

FIG. 14B shows longer survival of mice given injections of E1A-expressing ip1.E1A cells versus mice given injections of ip1.Efs human ovarian cancer cells (P<0.01). To assess the formation of malignant ascites after i.p. injection, suspensions of cells (harvested as above) at concentrations of $1 \times 10^6$ in 0.2 ml of Hank's balanced salt solution were injected i.p. into individual female nu/nu mice. In two studies, totals of nine mice for the ip1.Efs line, eight mice for the ip1.E1A1 line, and nine mice fore the ip1.E1A2 line were given injections. Mice were initially observed twice a twice a week for signs of tumor development and then daily when any or all of the following tumor symptoms appeared: abdominal bloating, loss of subcutaneous fat, hunched posture, and decreased movement. Mice were killed when they appeared moribund or, judging from the inventors previous experience, would not survive more than 24–48 h. Symptom-free mice were killed 120 days after injection. Autopsies were performed on all mice killed. Similar results were obtained from the two studies, and results were combined for analysis.

FIG. 15A–FIG. 15B and FIG. 15C show expression of neu-encoded p185 and LT in B104-1-1 cells stably transfected with plasmids encoding LT.

FIG. 15A. Immunoblotting for anti-p185 of whole cell lysates from B104-1-1 cells stably transfected with LT: BTn16 (lane 1), BTn14 (lane 2), BEn5 (lane 3) and NIH 3T3 (lane 4) cell lines. Following transfer to nitrocellulose, the blots were probed with monoclonal anti-p185 antibody (c-neu, Ab-3, Oncogene Science) followed by goat antimouse conjugated to horse radish peroxidase. The blot was subsequently developed using horse radish peroxidase substrate and hydrogen peroxide.

FIG. 15B. Immunoblot for LT of whole cell lysates of the stable transfectants. Blots were probed with anti-LT (SV 40 T-Ag, Ab-2, Oncogene Science) and then with [125I]-protein A. Washed and dried blots were exposed for autoradiography. Lysates of BTn16, lane 1; BTn14, lane 2; BEn5, lane 3 and NIH 3T3 cell line, lane 4.

FIG. 15C Southern blotting for genomic neu using 32P-labeled 0.4 and 0.8 kb Bam H1 fragments (11) from neu cDNA probe to hybridize with Bam H1 digested genomic DNA isolated from BTn16, lane 1; BTn14, lane 2; BEn5, lane 3 and NIH 3T3 cells, lane 4. The rat neu-specific bands are indicated by a triangle.

Figure 16:
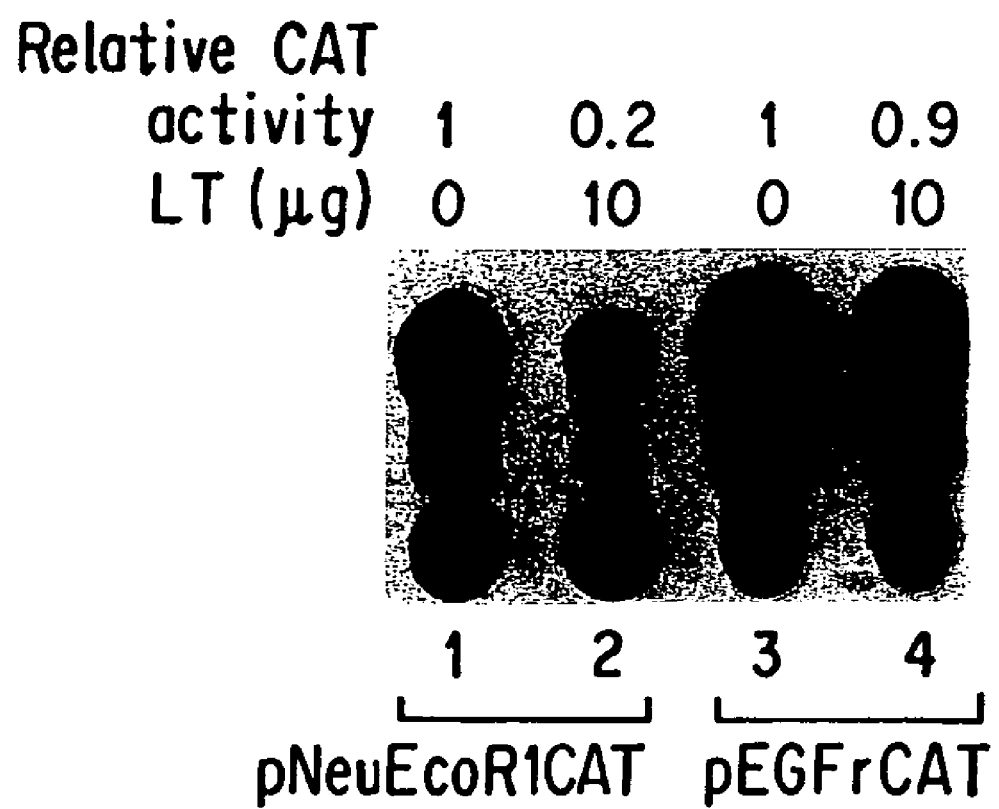

FIG. 16 shows the effect of LT on the upstream regulatory sequences of neu and epidermal growth factor receptor. One mg of pNeuEcoR1CAT (lanes 1 and 2) or pEGFrCAT (lanes 3 and 4) were cotransfected into NIH 3T3 cells with 10 mg of plasmid encoding LT, pVU-0 (lanes 2 and 4) or with control plasmid, pSV2E (lanes 1 and 3) which does not contain LT coding region. Transfections and CAT assays were carried out as described previously (Yu et al. 1992). CAT assays were standardized to equal protein concentrations of the cell extracts. The study was repeated 4 times and experimental error was within 13%. One representative set of data is shown.

Figure 17:
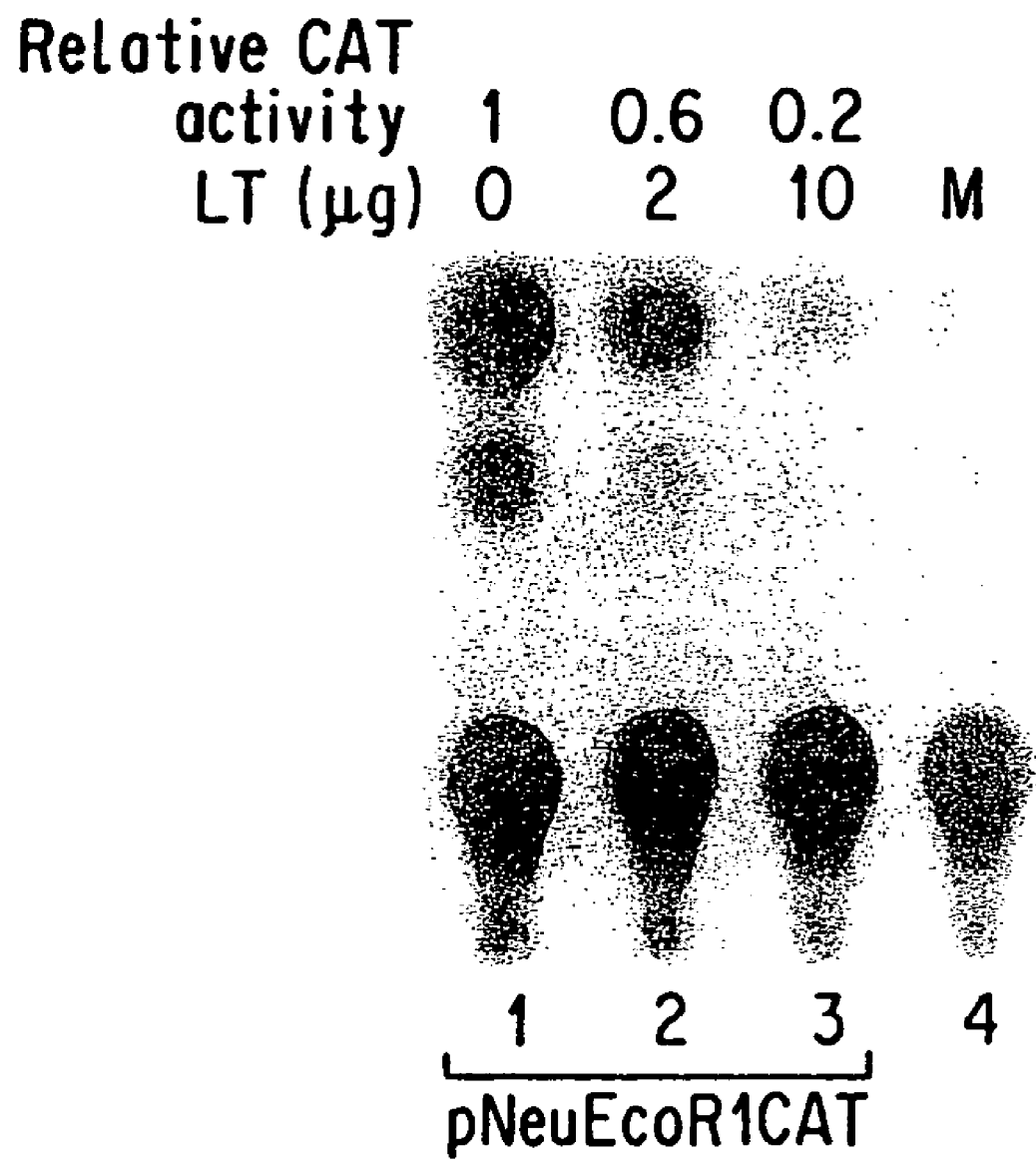

FIG. 17 shows the effect of increasing concentrations of LT on the activity of the regulatory sequences of neu. Two and 10 mg of pVU-0 were cotransfected with 1 mg of pneuEcoR1CAT into NIH 3T3 cells. The total amount of DNA transfected was equal for all reactions, with the control plasmid, pSV2E, being used to make up a final DNA concentration of 11 mg. Lane 4, M, is control CAT assay of extracts from untransfected NIH 3T3 cells. Representative data of 3 studies is shown; standard deviation was 11%.

Figure 18A:
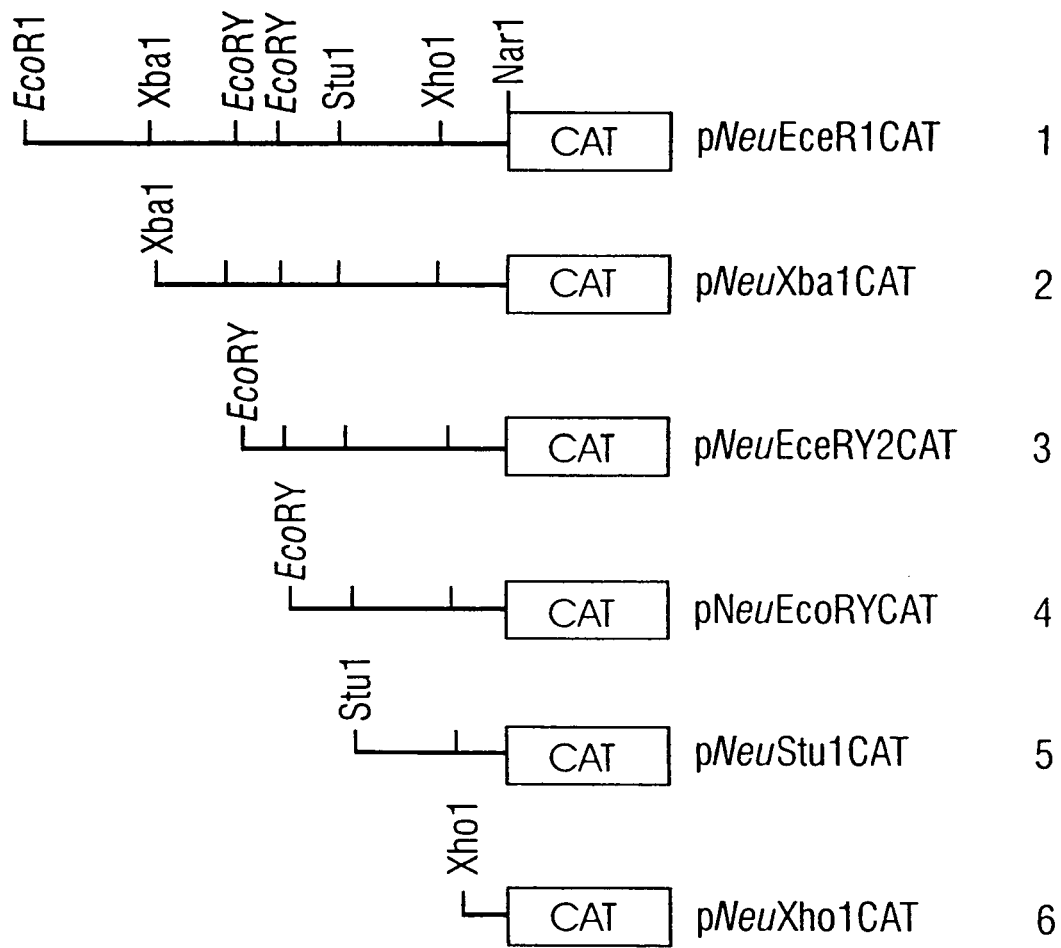
Figure 18B:
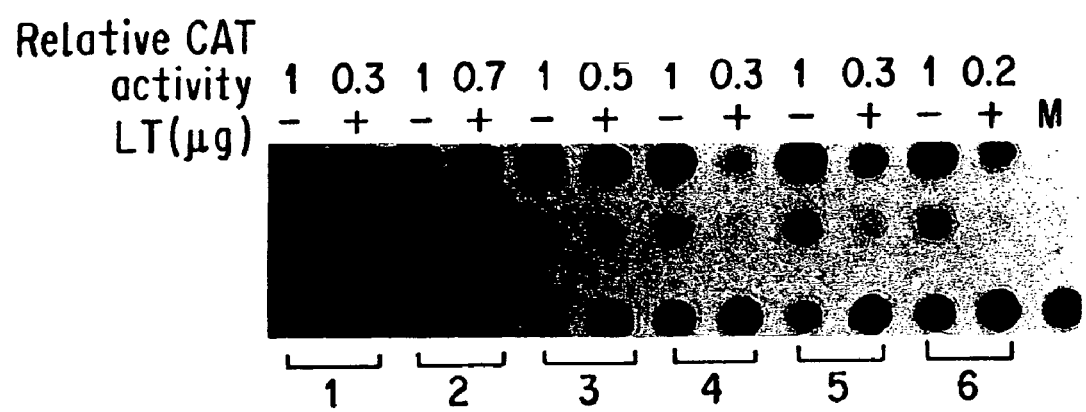

FIG. 18A and FIG. 18B show data from serial deletions.

FIG. 18A Series deletion-CAT constructs of the rat neu promoter.

FIG. 18B Mapping of LT responding region in the neu upstream regulatory sequence using the neu deletion-CAT constructs. One mg of each of the neu deletion-CAT constructs were cotransfected into NIH 3T3 cells with 10 mg of the LT-producing plasmid, pVU-0 (indicated by+) or 10 mg of filler plasmid, pSV2E (indicated by–): Set 1, pneuEcoR1CAT; set 2, pneuXba1CAT; set 3, pneuEcoRV2CAT; set 4, pneuEcoRVCAT; set 5, pneuStu1CAT; set 6, pneuXho1CAT; M, control CAT assay of extracts from untransfected NIH 3T3 cells. Each set (set 1, set 2, etc.) of CAT reactions with (+) and without LT (−) were standardized to equal protein concentrations.

Figure 19:

FIG. 19 shows gel shift assay demonstrating DNA-protein complex formed with the Xhol-Nar1 region of the neu promoter. The $^{32}$P-labeled DNA is the 94 base pair Xhol-Nar1 fragment. Lanes 1 and 2, nuclear extract from NIH 3T3 cells; lanes 3 and 4, nuclear extract from BTn 14 cell line. Lanes 2 and 4 contain approximately 250-fold unlabelled Xhol-Nar1 fragment as specific competitor. Lane 5, $^{32}$P-labeled Xhol-Nar1 fragment only. Incubation of probe ($10^5$ cpm) with nuclear extracts (3 $\mu$g) were carried out as described (Dynlacht et al., 1991) and samples were electrophoresed through a native 4.5% polyacrylamide gel (80:1; acrylamide:bisacrylamide) containing 0.5×TBE (45 mM boric acid, 1 mM EDTA, pH 8) for 2.5 h at 40° C. F indicates free probe.

Figure 20A:
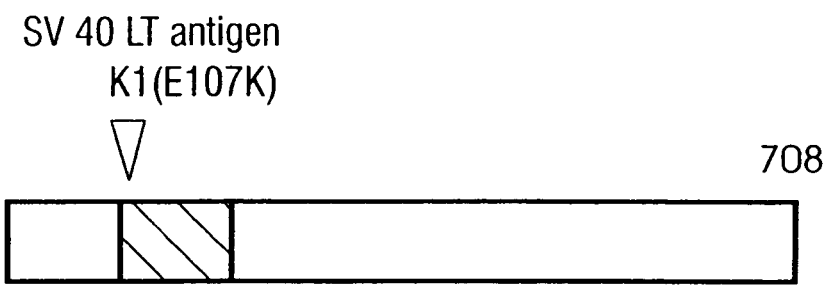
Figure 20B:
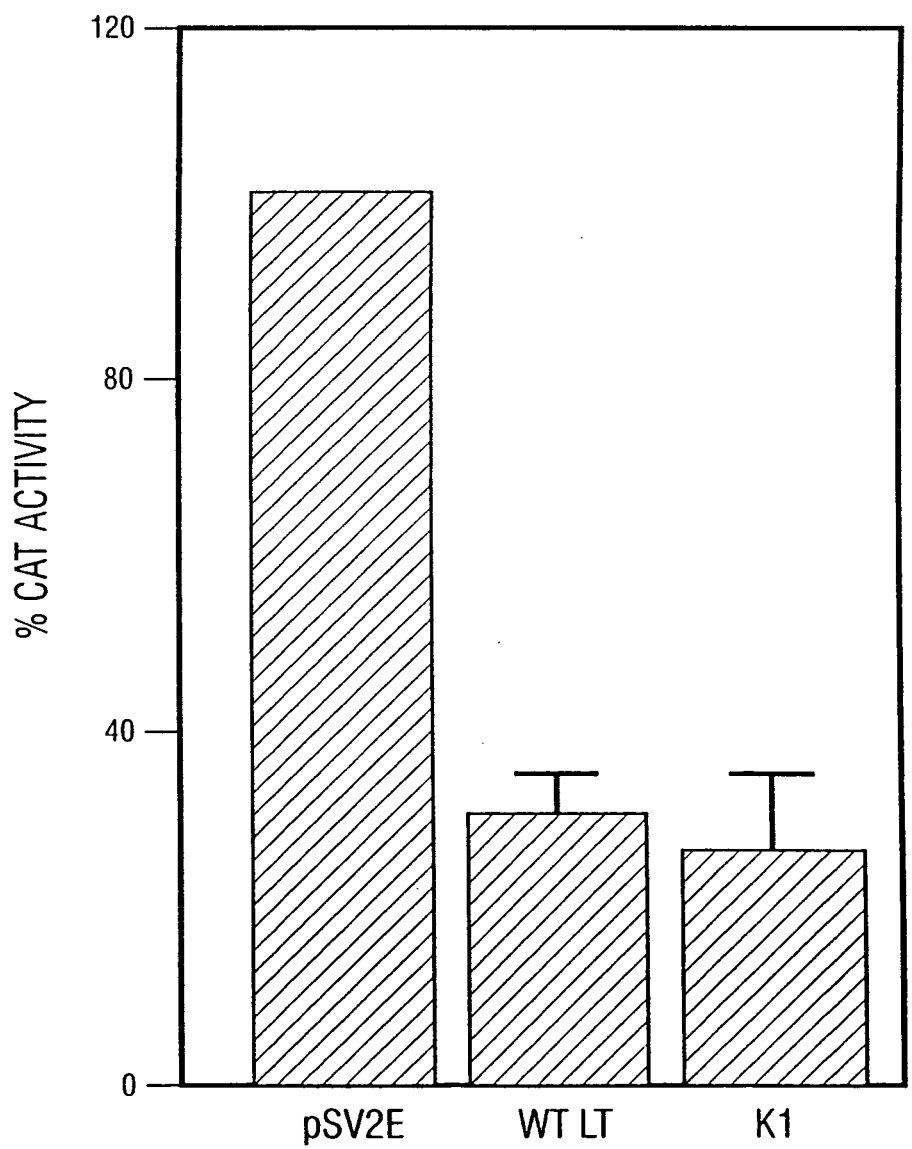
Figure 20C:
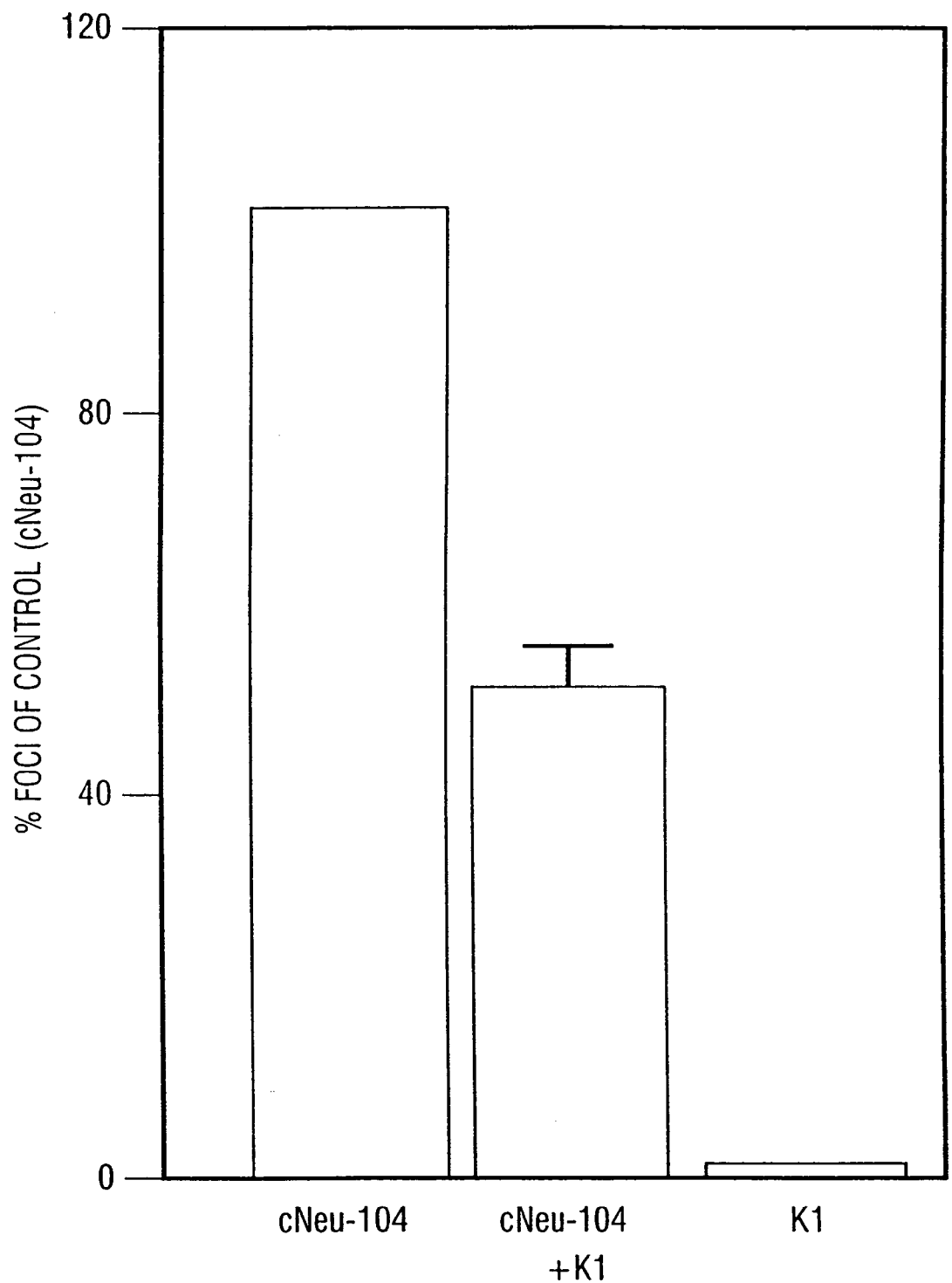

FIG. 20A FIG. 20B, and FIG. 20C show the effect of mutant LT on neu promoter activity.

FIG. 20A. Schematic diagram of LT showing Rb binding domain (shaded black). K1 encodes LT with single amino acid change (glu 107 to lys) in the Rb binding domain of the 708 amino acid LT protein.

FIG. 20B. Activity of pneuXho1CAT (with control plasmid pSV2E) and inhibition of activity in the presence of wild type LT (WT), and mutant LT (K1). One mg pneuXho1CAT was cotransfected with 10 mg of filler plasmid, pSV2E, or wild type LT (pVU-0) or mutant LT (pK1).

FIG. 20C. Effect of K1 on the transforming activity of activated neu. One mg of cNeu-104 was cotransfected with 2 mg of K1 and 0.1 mg of pSV2neo into Rat-1 cells. pSV2E was used as filler plasmid so that a final 5 mg DNA was transfected into cells. Cells were split 1:4 48 hours after transfection and duplicate plates were subsequently grown in regular medium (DMEM/F12 plus 10% calf serum) or regular medium supplemented with 250 mg/mL G418. Foci and G418-resistant colonies were stained and counted after 3–4 weeks. Results are expressed as ratio of foci to that of G418-resistant colonies from each transfection to correct for transfection efficiency. The number of foci from transfecting cNeu-104 alone was set at 100%.

Figure 21:

FIG. 21 shows liposome-deviated direct gene transfer techniques allow the delivery of the E1A gene to neu-overexpressing SK-OV-3 human ovarian cancer cell. The three mice were each injected with SK-OV-3 cells. Five days later, the mice were injected with (1) E1A DNA only, (2) complex of liposome and Efs DNA (an E1A frame shift mutant that does not cause active E1A to be produced), and (3) complex of liposome and E1A DNA. Booster injections of the same compositions were given each respective mouse on a weekly basis for the remainder of the mouse's life. Mouse 1 developed extensive bloody ascites and died 65 days after SK-OV-3 injection. Mouse 2 developed extensive blood ascites and a large tumor and died 76 days after the injection of SK-OV-3 cells. Mouse 3 appeared healthy and was alive 160 days after SK-OV-3 injection.

Figure 22:
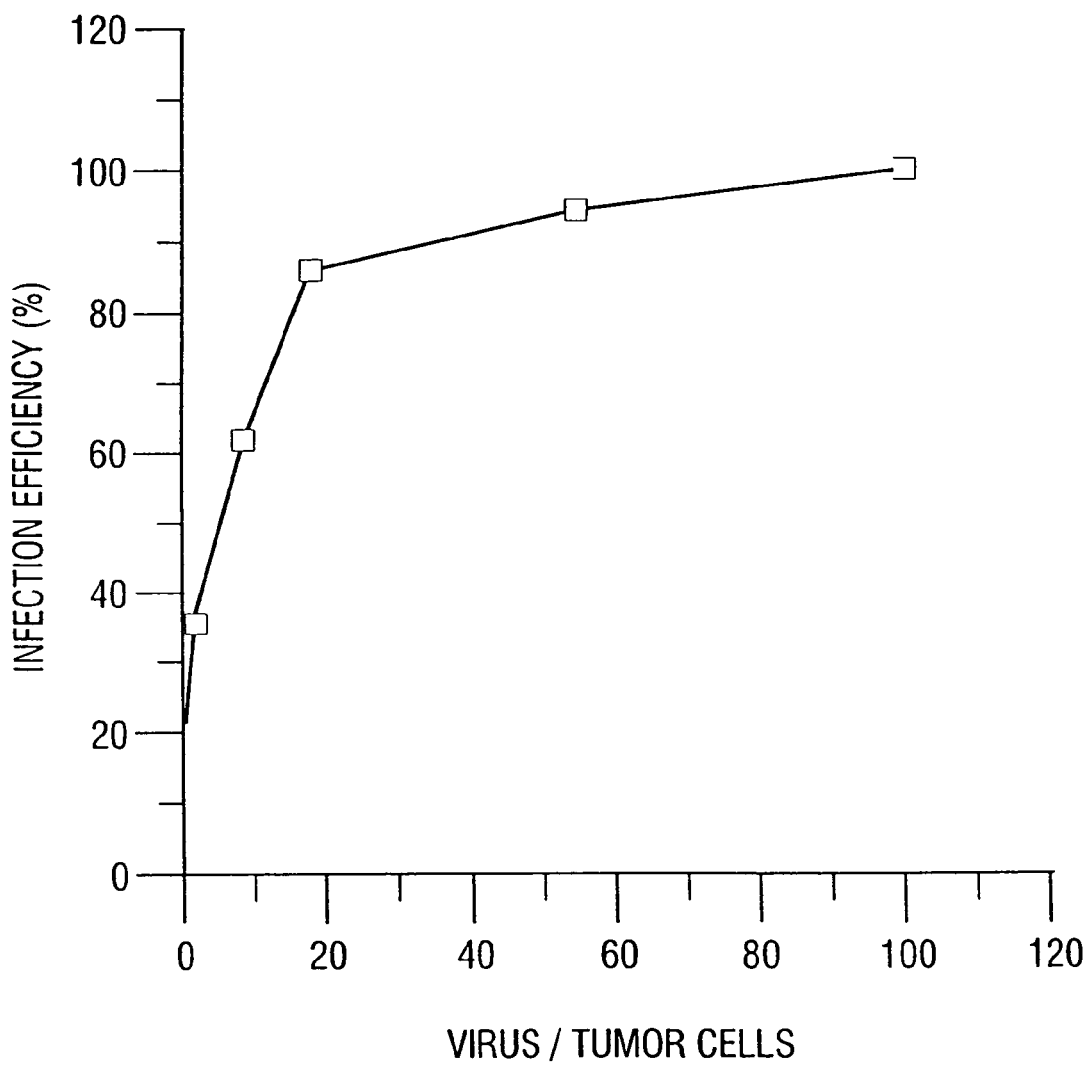

FIG. 22 shows the infection efficiency of adenovirus in ovarian cancer SK-OV3(i.p.). SK-OV-3(i.p.) in 6 well plates ($2.5 \times 10^5$/well) were infected once by Ad.RSVβgal at different virus/tumor cell ratios. Two days later, cells were fixed and stained with X-gal. Infection efficiency=No. of positive cells/No. of total cells×100%.

Figure 23:
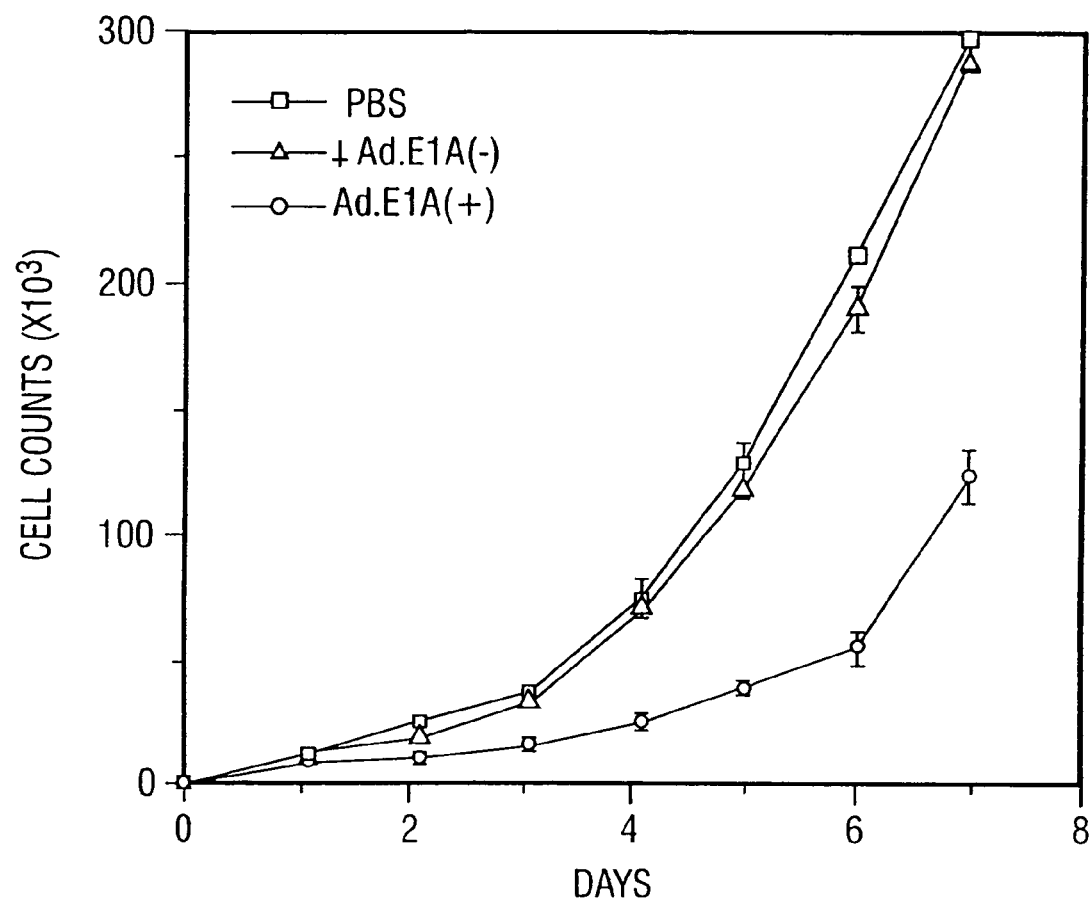

FIG. 23 shows a growth curve of SK-OV-3(i.p.) after treatment by Ad.E1A in vitro. SK-OV-3(i.p.) in 12 well plates ($10^4$/well) were infected once by $2 \times 10^5$ adenovirus and cell growth was followed for 7 days.

Figure 24:
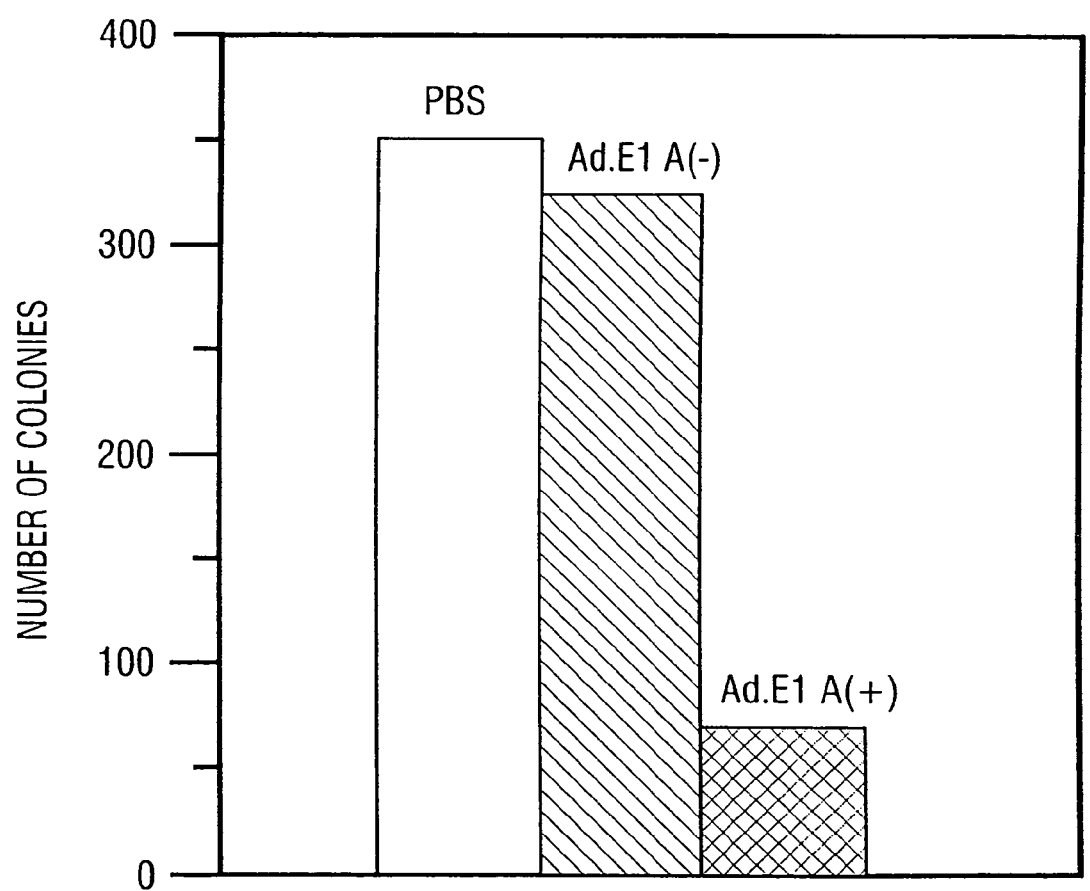

FIG. 24 shows colony formation in soft agarose. SK-OV-3(i.p.) cells were infected once with adenovirus at a virus/tumor ratio of 20/1. Aliquots of $5 \times 10^4$ cells were mixed with 0.35% agarose in DMEM medium and plated over a base layer of 0.7% agarose. Culture medium was allowed to harden in 6 well plates (n=3). Colonies were stained and counted about 6 weeks later.

Figure 25:
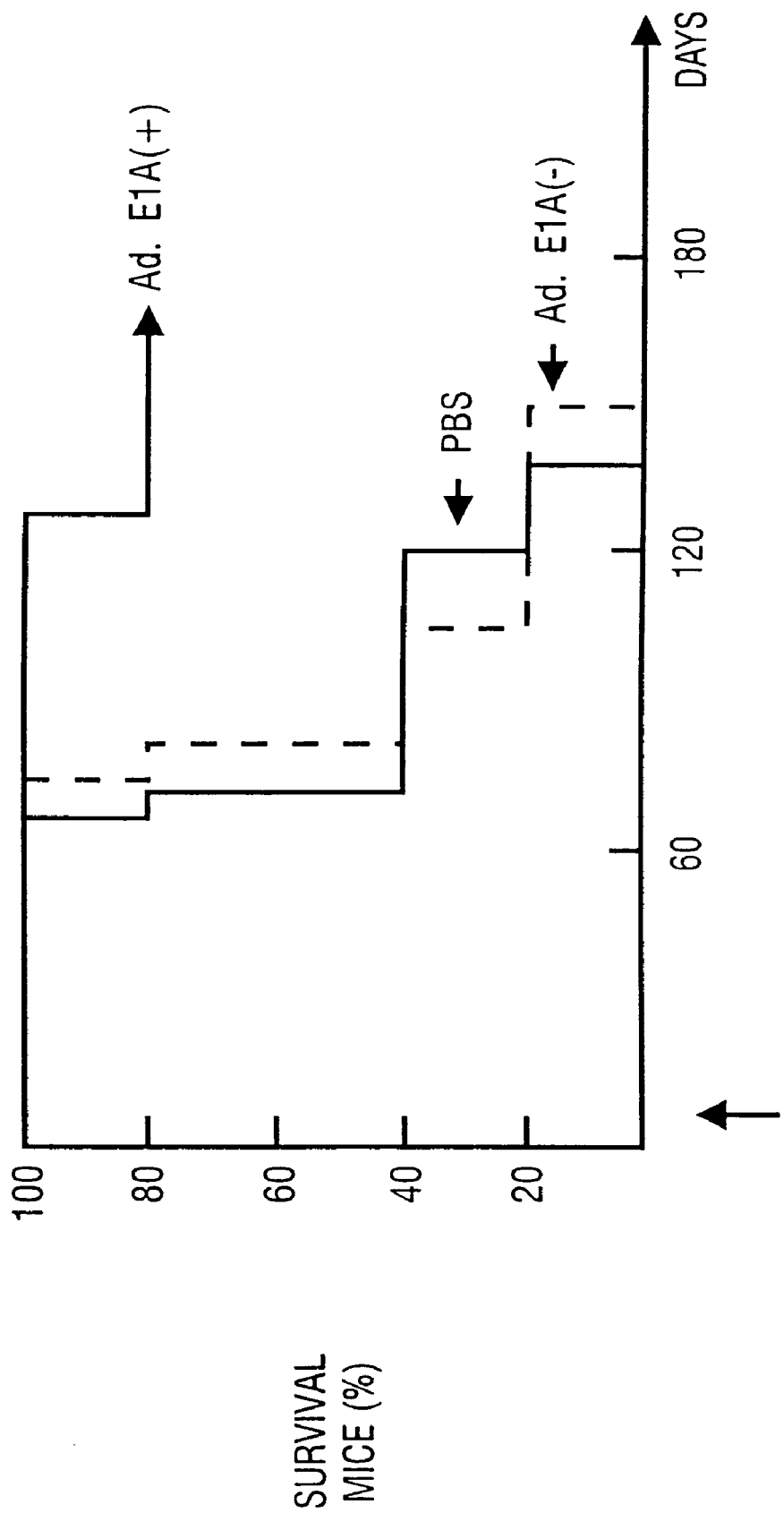

FIG. 25 shows the Ad. E1A therapeutic effect on ovarian cancer SK-OV-3(i.p.). SK-OV-3(i.p.) ($10^6$/mouse) were injected i.p. in female nu/nu mice. Five days later, mice were given i.p. injection of 0.1 ml of viral solution (titer: $2 \times 10^9$ PFU/ml) once/day for three days, then once/week for 4.5 months. The responses and survival rate were observed for more than one-half year (n=5).

Figure 26A:
Figure 26B:

FIG. 26A and FIG. 26B show in vivo Ad.RSVβgal-mediated transfer of the lacZ gene to intraperitoneal SK-OV-3(i.p.), 26A; and to intratracheal H820, 26B.

FIG. 26A Mice were administered intraperitoneal SK-OV-3(i.p.), two months later after tumor development, Ad.RSVβgal was administered intraperitoneally. Tumor and organs were evaluated for the presence of β-gal using X-gal. The lacZ gene was localized in tumor cells and only slight β-gal activity was detected in normal organs.

FIG. 26B Mice were administered intratracheally H820. Two months later, after tumor development, AD.RSβgal was administered intravenously. Tumor and organs were evaluated for the presence of β-gal using X-gal. The lacZ gene was localized in tumor cells and only slight β-gal activity was detected in some normal organs.

Figure 27:
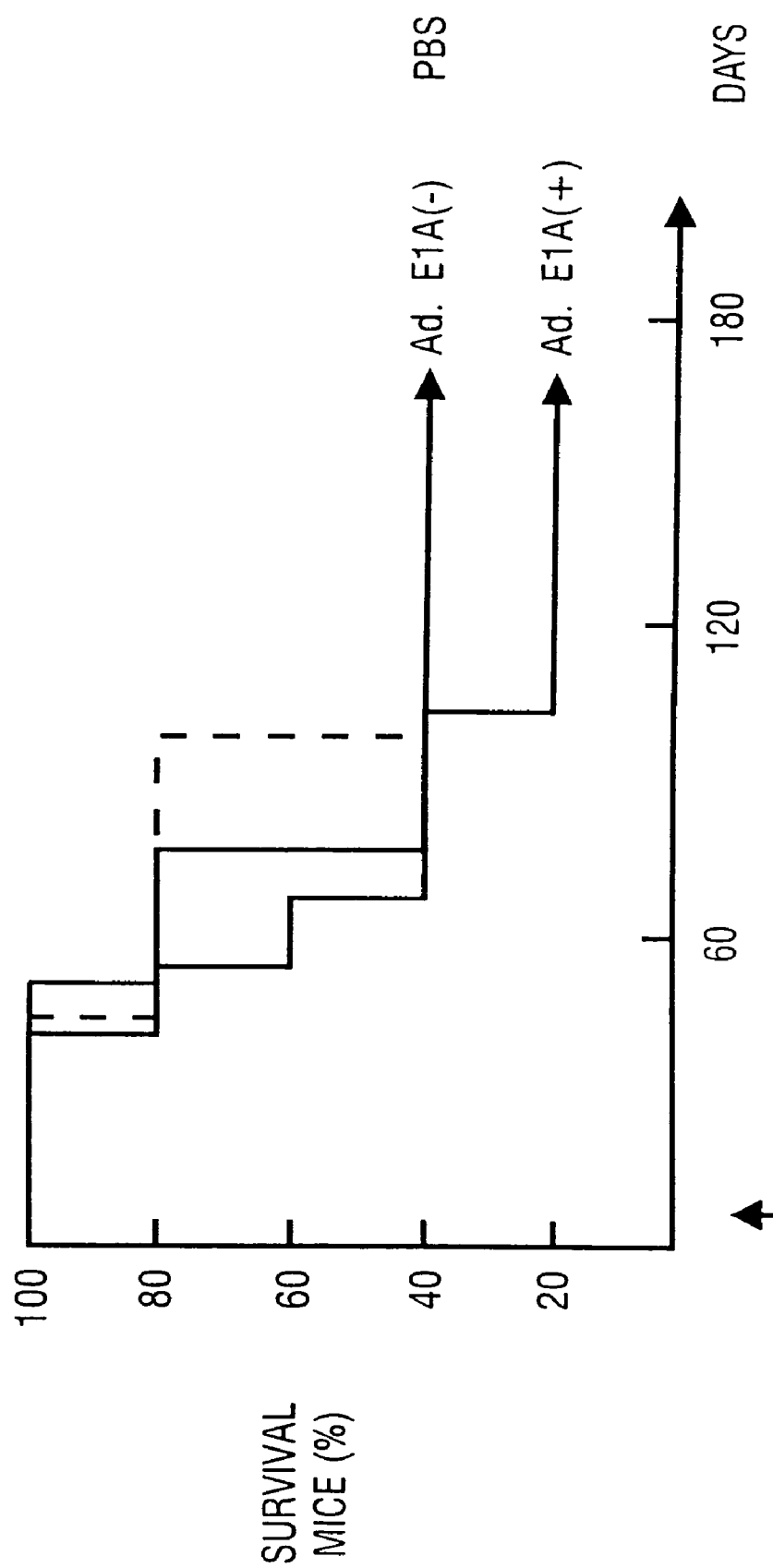

FIG. 27 shows the survival of mice bearing ovarian cancer 2774 after treatment by Ad.E1A. Human ovarian cancer cell line 2774 which has low level expression of HER-2/neu was injected i.p. into nu/nu mice ($5 \times 10^5$/mouse). Five days later, mice were given i.p. injection of 0.1 ml of viral solution (titer: $2 \times 10^9$/ml) once/day for three days, then once/week for 4.5 months. The responses and survival rate were observed. AD.E1A(+) did not have significant therapeutic effect in 2774. Analysis of the results and the data of SK-OV-3(i.p.) which has high expression level of HER-2/neu indicate that AD.E1A(+) can specifically inhibit the growth of tumor which has high expression level of HER-2/neu.

Figure 28A:
Figure 28B:
Figure 28C:
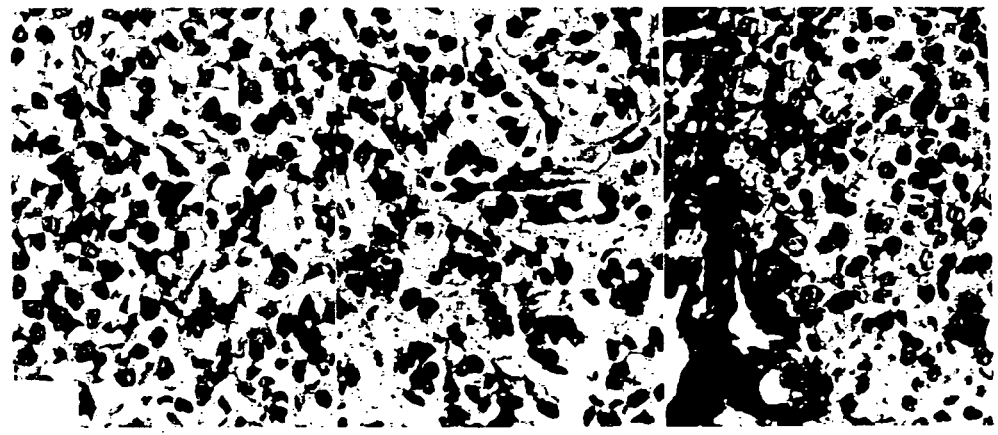

FIG. 28A, FIG. 28B and FIG. 28C show a histoimmunochemical analysis of representative histological sections of treated and control mice.

FIG. 28A Histological section from intraperitoneal SK-OV-3(i.p.) stained with hematoxylin and eosin.

FIG. 28B Expression level of BER-2/neu P185 protein: stained by polyclonal antibody against P185 with ABC alkaline phosphatase substrate kit. Positive: red color.

FIG. 28C Expression of AD.E1A protein: stained by monoclonal antibody against AD.E1A with ABC ACE substrate kit for horseradish peroxides. Positive: dark red color. Ad.E1A protein was detected in tumor tissue treated by Ad.E1A(+) in vivo. The expression level of HER-2/neu P185 was greatly inhibited in treated mouse tumor tissue.

Figures 29A, 29B, 29C:
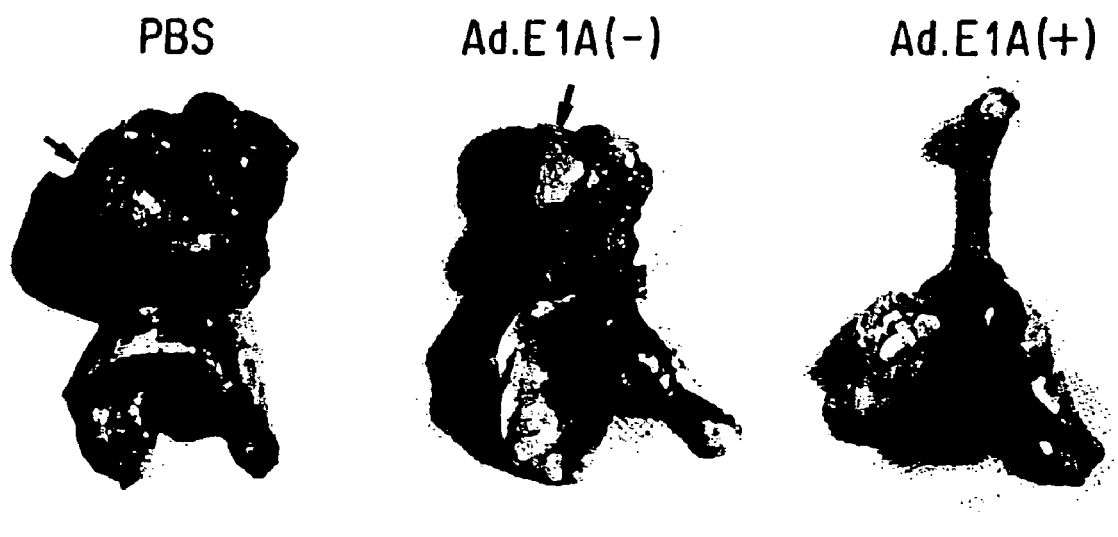

FIG. 29A FIG. 29B and FIG. 29C show representative mediastinal blocks of treated and control mice. Arrow: Tumor.

Figure 30A:
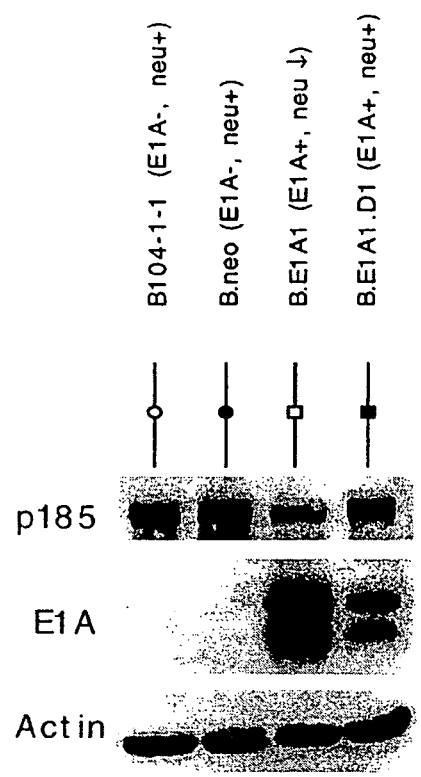

FIG. 30A. Effect of taxol (0.01–100 μM) on the cell growth of rat fibroblast with various HER-2/neu and E1A expression. Cell lysates were run through 8% SDS-PAGE and blotted with anti-p185 and anti-E1A antibody.

Figure 30B:
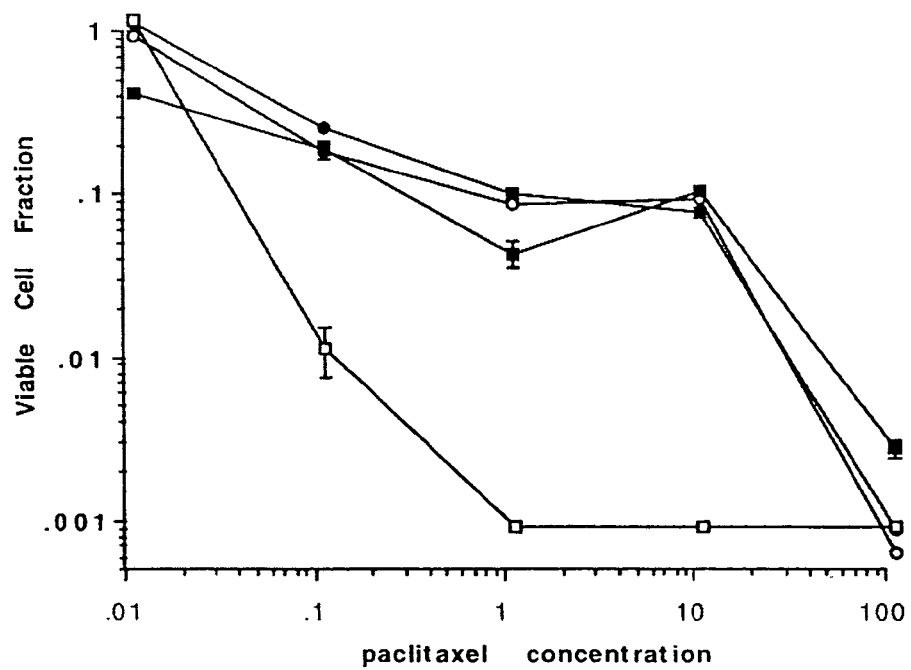

FIG. 30B. Effect of taxol (0.01–100 μM) on the cell growth of rat fibroblast with various HER-2/neu and E1A expression. B104-1-1, B.neo, B.E1A1.Hy, and B.E1A1.D1 were examined for the effect of taxol on cell growth by MTT assay, and the percentage of cell growth was calculated by defining the absorption of cells not treated with taxol as 100%. Bars, SD. The highest inhibition of cell growth was seen in B.E1A1.Hy with HER-2/neu down-regulated by E1A, with taxol of 0.1 to 10 μM.

Figure 31A:
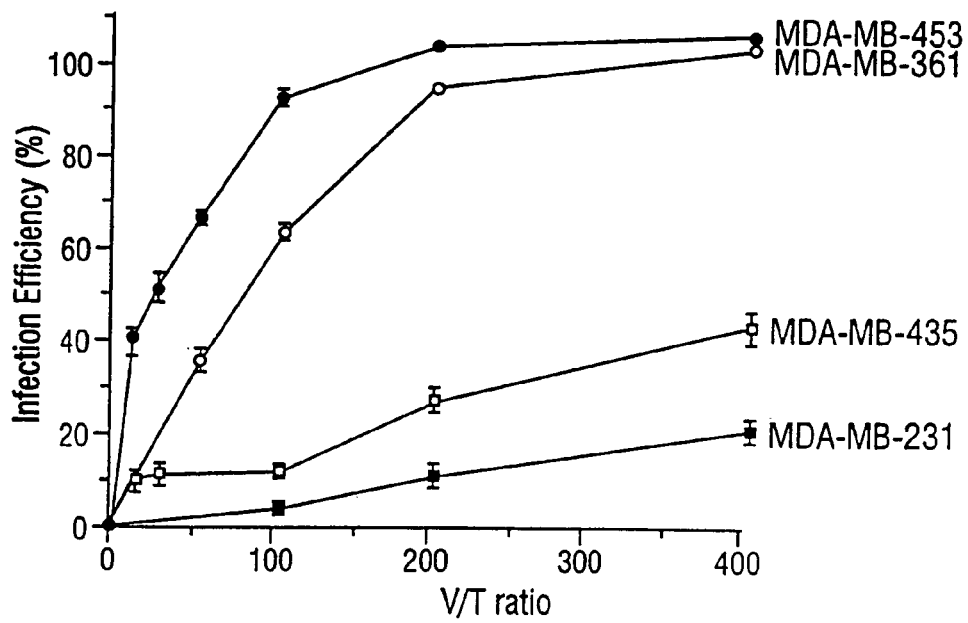

FIG. 31A. Infection efficacy of Ad.RSVlacZ. Beta-galactosidase expression was examined after exposure of the MDA-MB-435, and 453, 231, and 361 with various V/T ratio. Bars, SD. The infection efficiency was higher among HER-2/neu-overexpressing breast cancer cell lines, MDA-MB-453 and MDA-MB-361 than basal level HER-2/neu breast cancer cell line, MDA-MB-435 and MDA-MB-231.

Figure 31B:
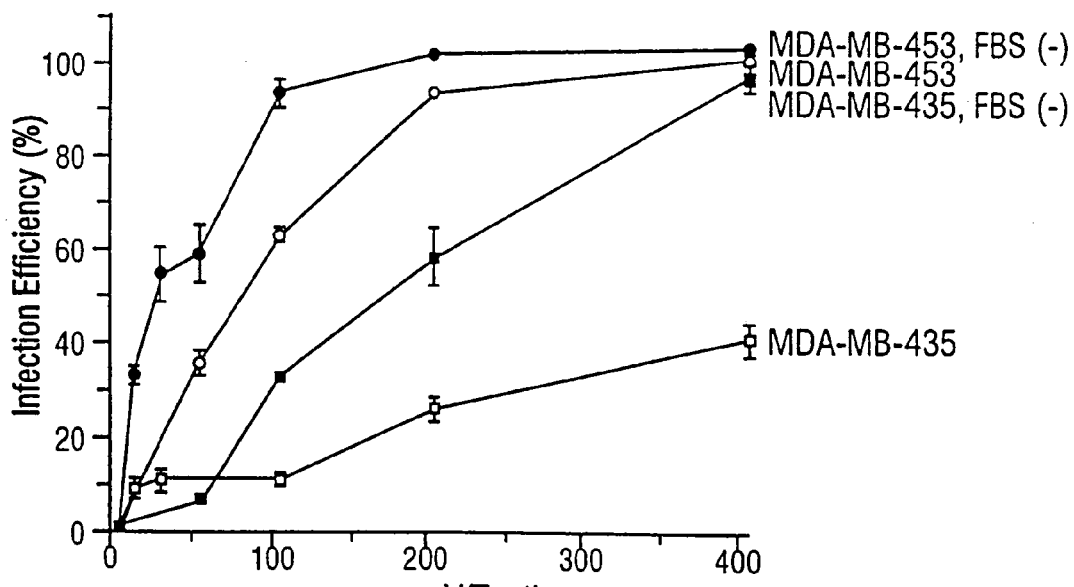

FIG. 31B. Infection efficacy of Ad.RSVlacZ. with high infection protocol, which depletes FBS during infection, infection efficiency higher than 95% can be obtained in MDA-MB-435, with a V/T ratio of 400:1 and MDA-MB-453, with a V/T ratio of 200:1.

Figure 32A:
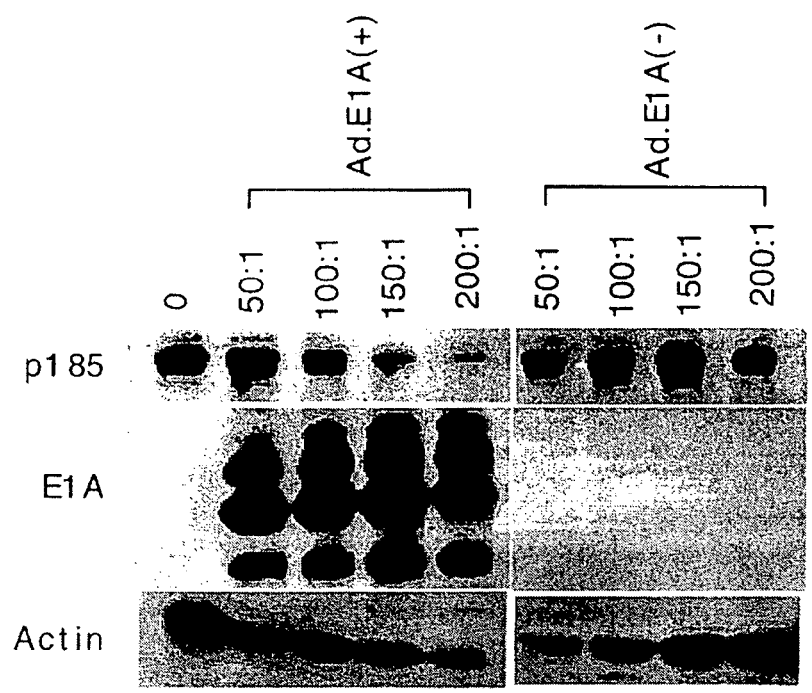

FIG. 32A. Effect of adenovirus 5 E1A on the expression of BER-2/neu among breast cancer cell lines. MDA-MB-453 cell were treated with various V/T ratio, (0, 50:1, 100:1, 150:1, 200:1) of Ad.E1A(+) and Ad.E1A(−). Cell lysates were run through 8% SDS-PAGE and blotted with anti-p185 and anti-E1A antibody. Down-regulation of p185 expression is seen in a dose-dependent fashion in MDA-MB-453.

Figure 32B:
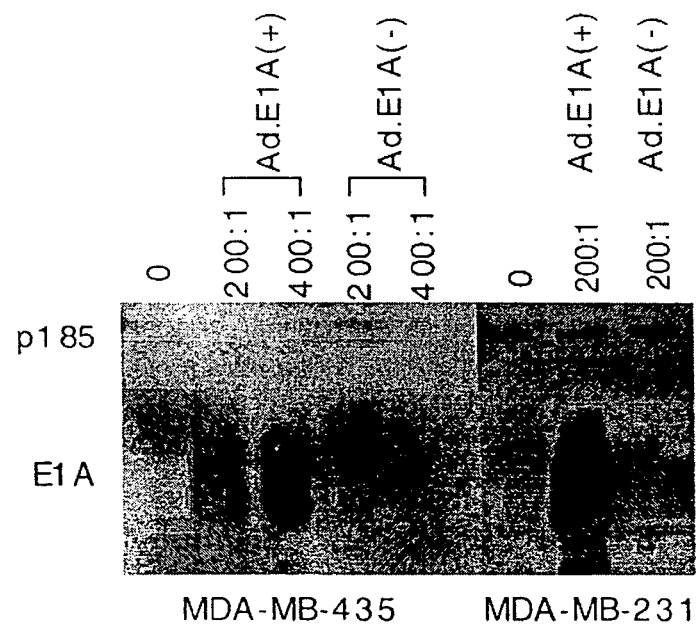

FIG. 32B. Effect of adenovirus 5 E1A on the expression of HER-2/neu among breast cancer cell lines. MDA-MB435 cell were treated with V/T ratio, 400:1 with Ad.E1A(+) and Ad.E1A(−) using high infection protocol. Cell lysates were run through 8% SDS-PAGE and blotted with anti-p185 and anti-E1A antibody. There was no difference in the basal level of the HER-1/neu. Comparable level of E1A expression was seen.

FIG. 33 Synergistic effect of E1A and taxol against HER-2/neu-overexpressing breast cancel line MDA-MB-453. Adenoviral vector was delivered under high (FIG. 4A. and FIG. 4B) or regular (FIG. 33C. and FIG. 33D) infection protocol for 48 hours, then exposed to various concentration of taxol was applied. The percentage of cell growth was calculated by defining the absorption of cells not treated with taxol or E1A as 100%. Bars, SD.

Figure 33A:
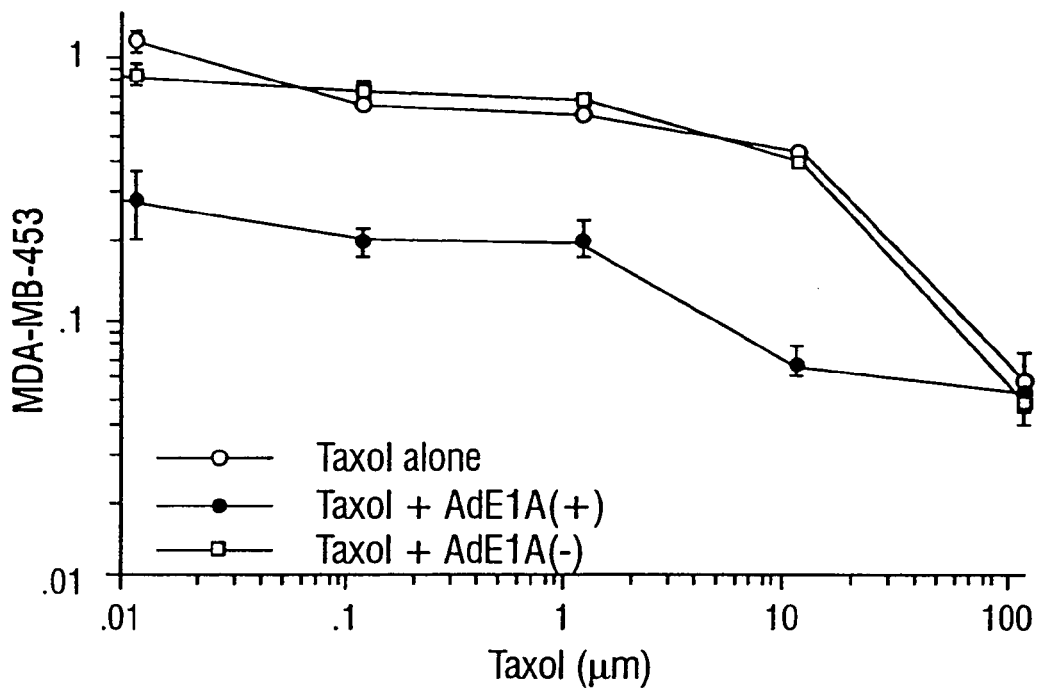

FIG. 33A. Synergist effect of Ad.E1A(+) V/T ratio of 200:1 and Taxol on MDA-MB-453.

Figure 33B:
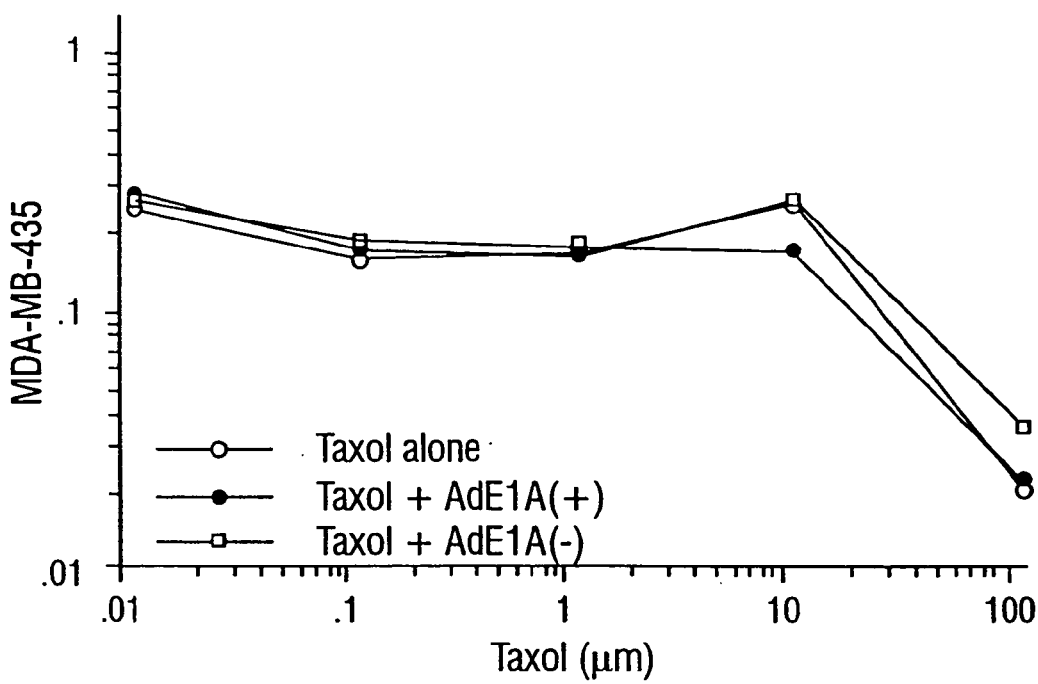

FIG. 33B. No synergistic effect of Ad.E1A(+) V/T ratio of 400:1 and taxol on MDA-MB-435.

Figure 33C:
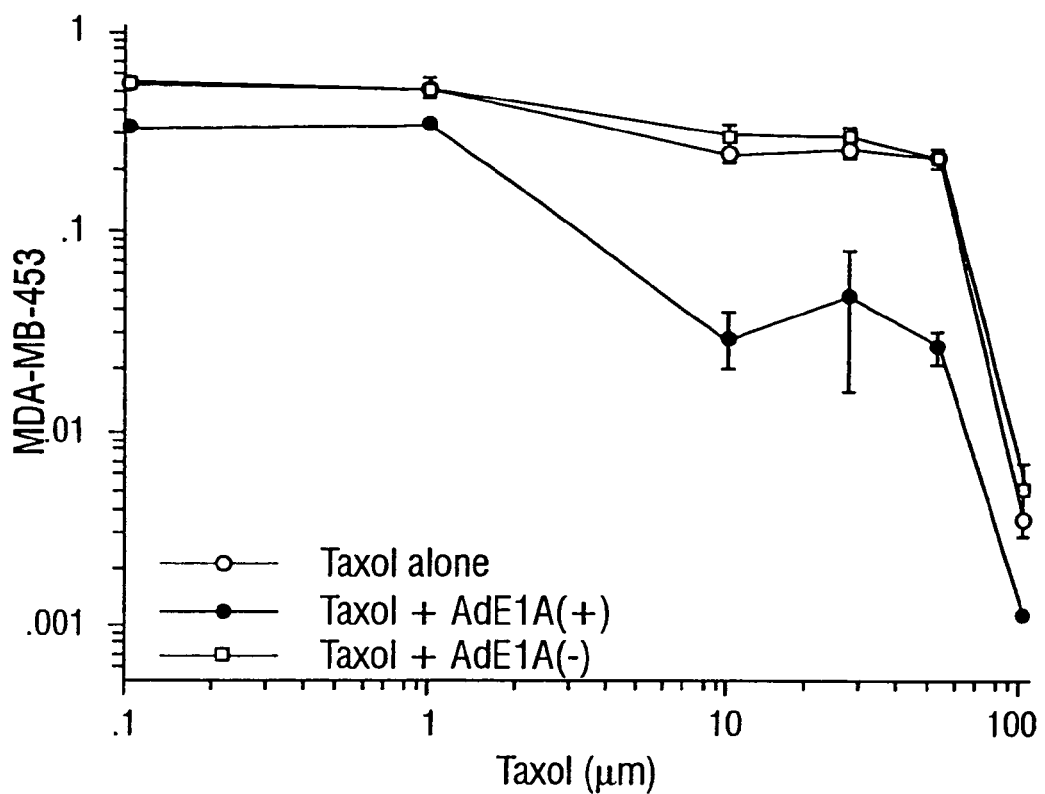

FIG. 33C. Synergist effect of Ad.E1A(+) V/T ratio of 200:1 and Taxol on MDA-MB-453.

Figure 33D:
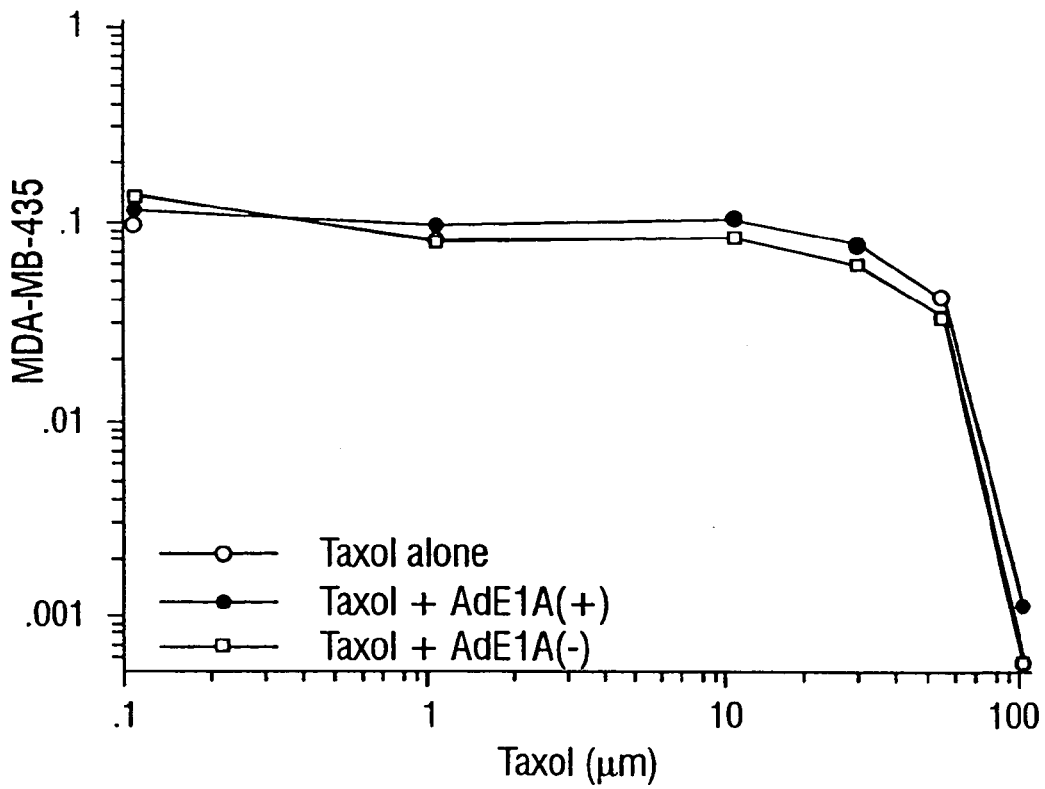

FIG. 33D. No synergistic effect of Ad.E1A(+) V/T ratio of 400:1 and taxol on the viable cell fraction of MDA-MB435.

FIG. 34. Synergistic effect of E1A and taxol 10 $\mu$M against HER-2neu-overexpressing breast cancel cell line MDA-MB-453 based on time scale. Adenoviral vector was delivered under high (FIG. 5A. and FIG. 5B) or regular (FIG. 5C. and FIG. 5D.) infection protocol for 48 hours, then exposed to taxol 10 $\mu$M. the viability of cells were followed by MTT assay, Day 0 is when the taxol was applied. The percentage of cell growth was calculated by defining the absorption of cells not treated with taxol or E1A as 100%. Bars, SD.

Figure 34A:
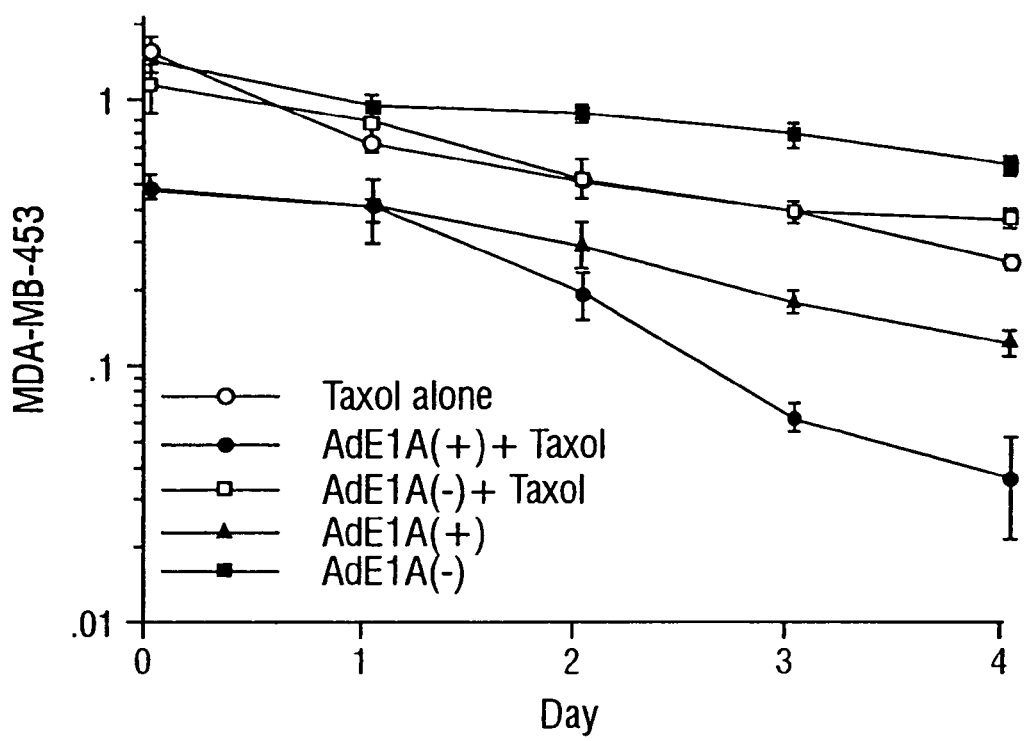

FIG. 34A. Synergist effect of Ad.E1A(+) alone shows cell growth suppression.

Figure 34B:
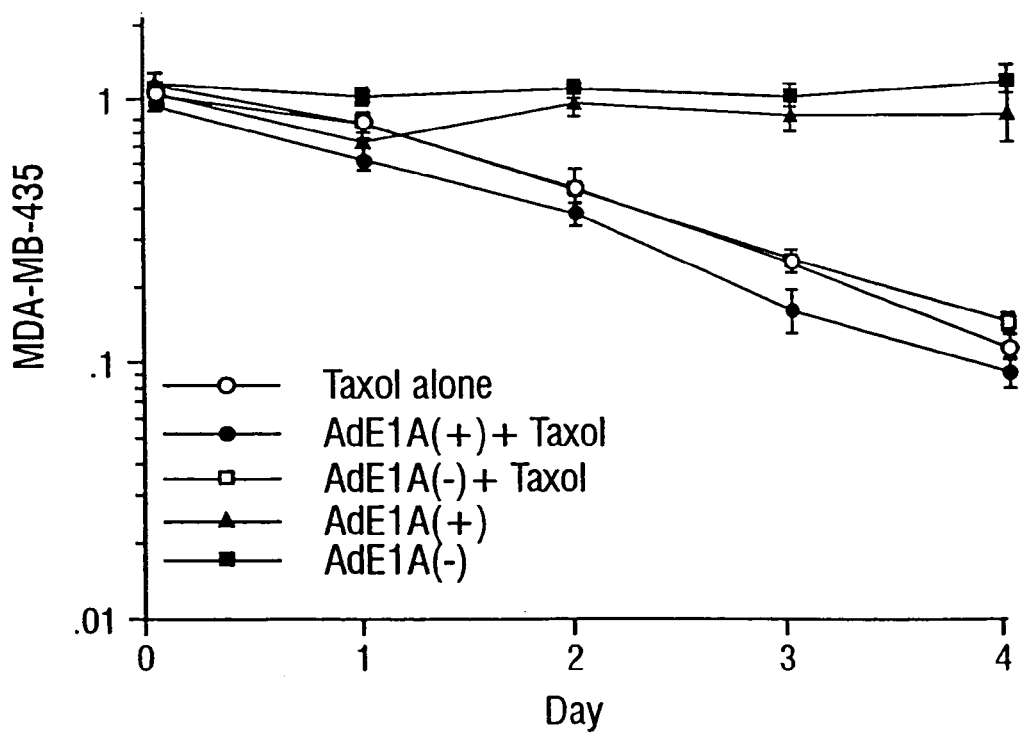

FIG. 34B. No synergistic effect of AD.E1A(+) V/T ratio of 400:1 and taxol on MDA-MB435. Ad.E1A(+) does not suppress cell growth. Low HER-2/neu is more sensitive to taxol.

Figure 34C:
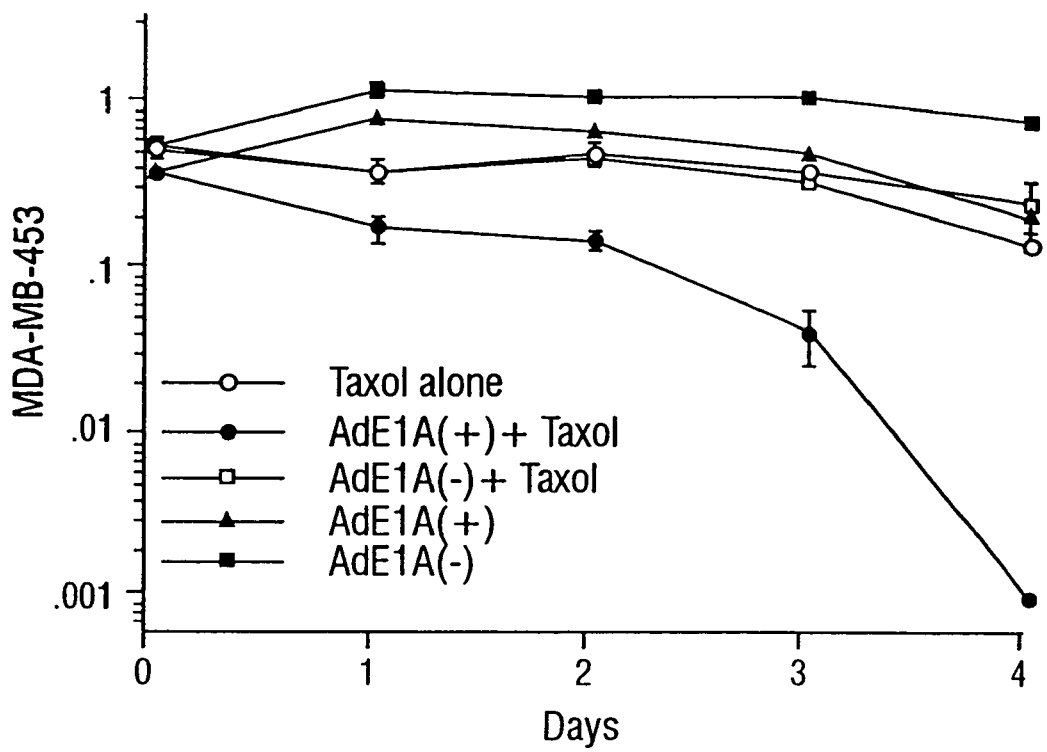

FIG. 34C. Synergist effect of AD.E1A(+) V/T ratio of 200:1 and Taxol on MDA-MB-453.

Figure 34D:
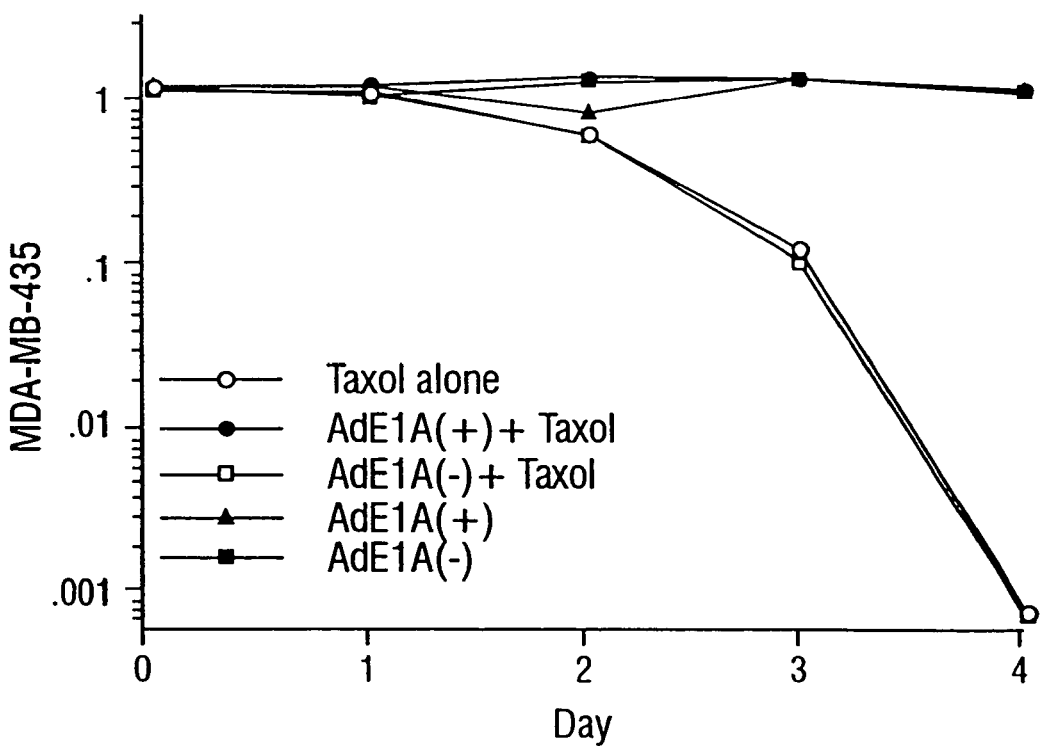

FIG. 34D. No synergistic effect of Ad.E1A(+) V/T ratio of 400:1 and taxol on the viable cell fraction of MDA-MBA435. Regular infection protocol results in more higher degree of cell kill due to continuous existing of FBS, which results in activation of cell cycles.

Figure 35:
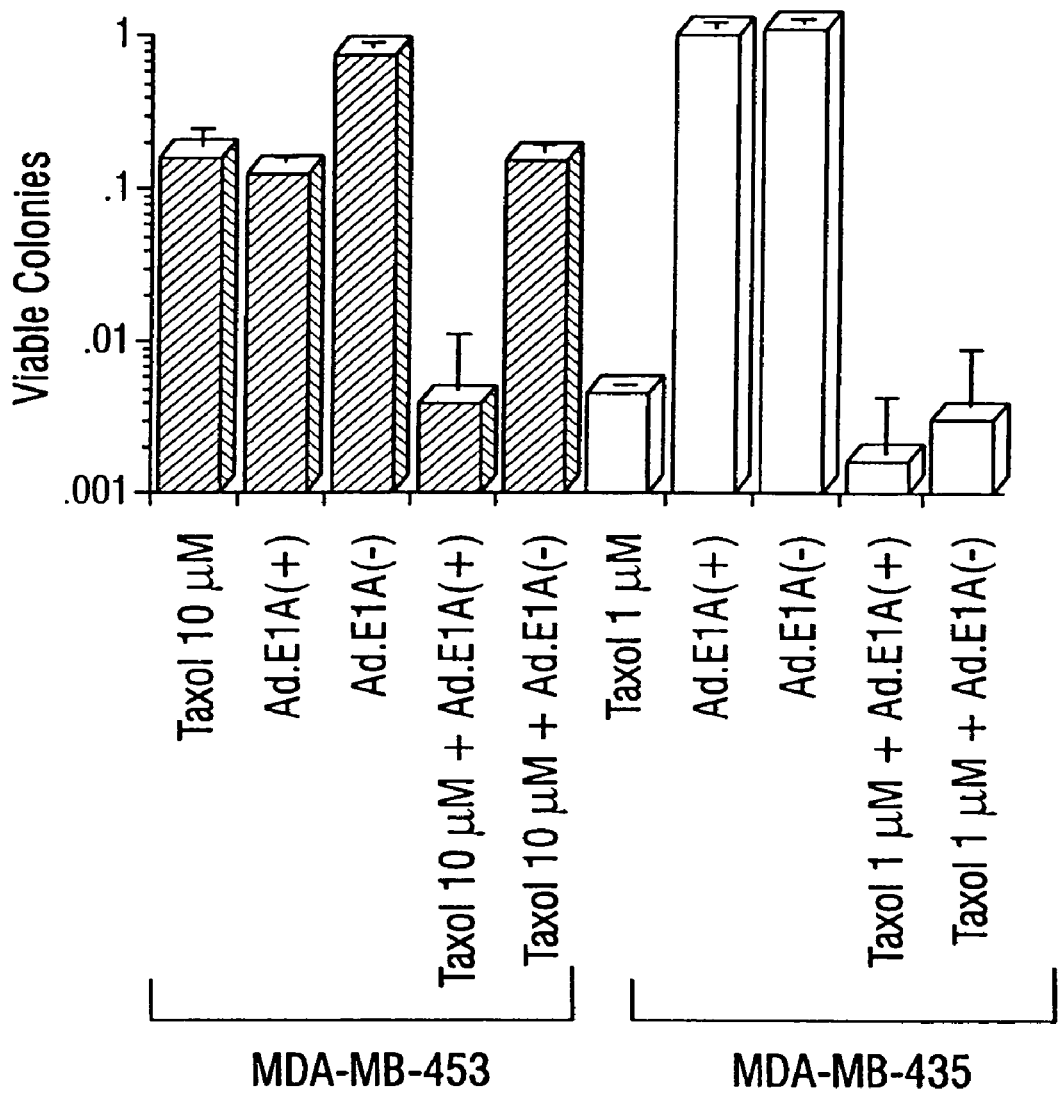

FIG. 35. Synergist effect of E1A and taxol 10 $\mu$M against BER-2/neu-overexpressing breast cancer line MDA-MB-453 on clonogenic assay. MDA-MB-453 shows synergistic suppression effect on the colony formation the soft agar with anchorage independent fashion by Ad.E1A(+) V/T ratio of 200:1 and Taxol 20 $\mu$M, adenoviral vector was delivered under regular infection protocol and the percentage of colonies was calculated by defining the colony number not treated with taxol and E1A as 100%. Bars, SD. No synergistic effect of adenovirus 5 E1A V/T ratio of 400:1 and Taxol (1 $\mu$M) on the viable cell fraction of MDA-MA435, adenoviral vector was delivered under high infection protocol and the percentage of colonies was calculated by defining the colony no. not treated with taxol and E1A as 100%. Bars, SD.

FIG. 36. Synergistic effect of E1A and taxol 10 $\mu$M against HER-2/neu-overexpressing breast cancer cell line MDA-MB-453 on direct cell counting.

Figure 36A:
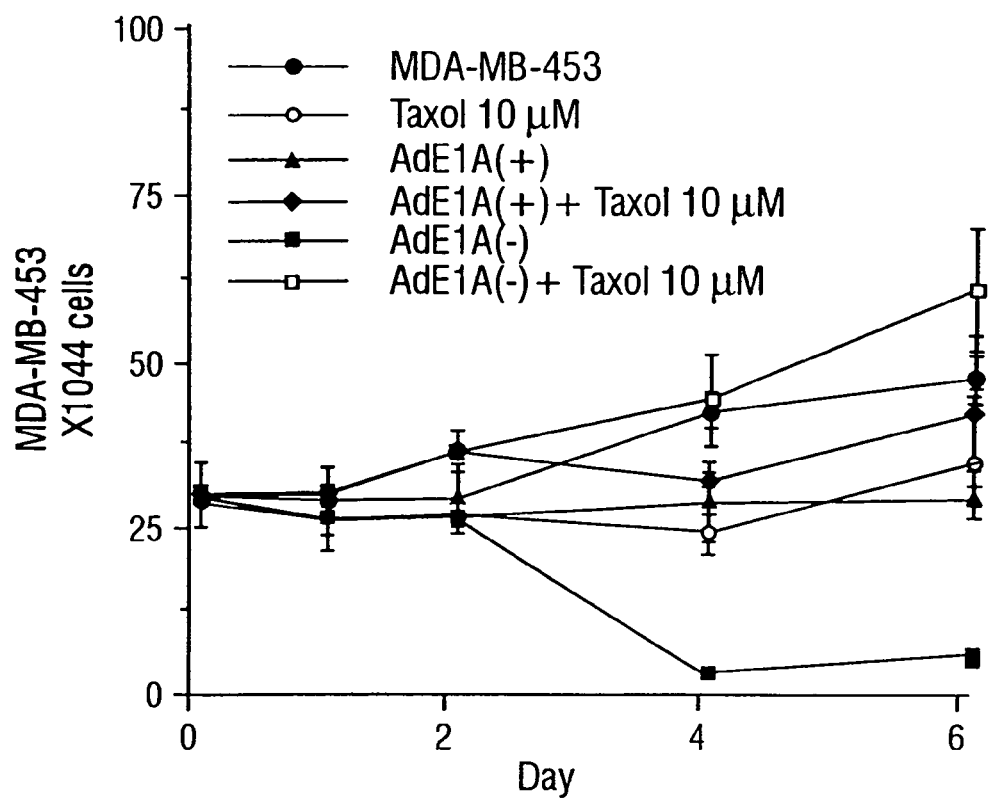

FIG. 36A. Growth curve of MDA-Mb-453. There was significant suppression of cell proliferation by Ad.E1A(+) V/T ratio of 200:1 and taxol 10 $\mu$M. Adenoviral vector was delivered without serum.

Figure 36B:
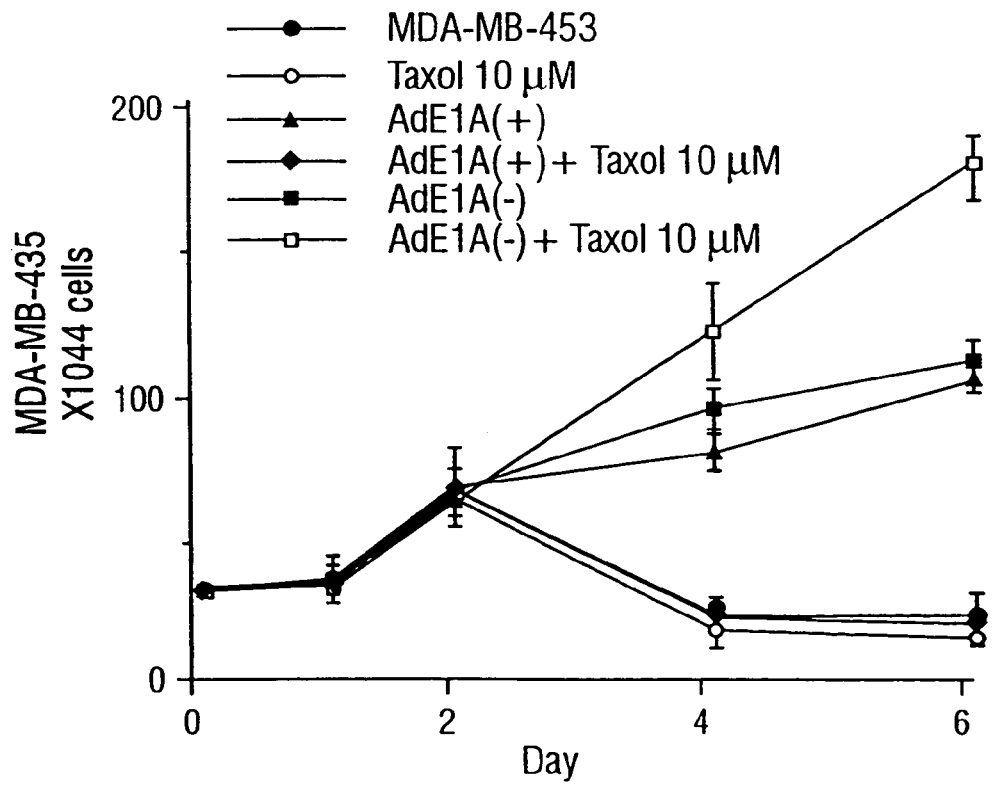

FIG. 36B. No synergistic effect of Ad.E1A(+) V/T ratio of 400:1 and taxol (10 $\mu$M) on the viable cell fraction of MDA-MB435, adenoviral vector was delivered under high infection protocol. The percentage of cell growth was calculated by defining the absorption of cells not treated with taxol or E1A as 100%. Bars, SD. Viable cells were checked by trypan blue 0.5%.

DETAILED DESCRIPTION OF THE INVENTION

The present invention seeks to overcome drawbacks inherent in the prior art by providing new treatment methods, compositions and kits for increasing the efficacy of antineoplastic agents against neu-mediated cancer.

The invention provides methods for treating neu-mediated cancers using a neu-suppressing gene product and a chemotherapeutic drug in order to inhibit neu-tyrosine kinase activity. The methods of the invention generally rest in using genes, for example, the E1A or the LT gene in combination with an anti-cancer agent effective to treat the cancer cells associated with neu over-expression.

A. Definitions and Techniques Affecting Gene Products and Genes.

E1A Gene Products and Genes

In this patent the terms "E1A gene product" and "E1A" refers to proteins having amino acid sequences which are substantially identical to the native E1A amino acid sequence and which are biologically active in that they are capable of binding to Rb, suppressing neu oncogene-mediated transformation, immortalizing cells, or crossreacting with anti-E1A antibody raised against E1A. Such sequences are disclosed, for example, in Berk et al., 1978. The term "E1A gene product" also includes analogs of E1A molecules which exhibit at least some biological activity in common with native E1A. Furthermore, those skilled in the art of mutagenesis will appreciate that other analogs, as yet undisclosed or undiscovered, may be used to construct E1A analogs. Such analogs may be generated in the manners described for the generation of LT mutants in Kalderon et al. (1984). There is no need for an "E1A gene product" or "E1A" to comprise all, or substantially all of the amino acid sequence of the native E1A gene. Shorter or longer sequences are anticipated to be of use in the invention. For example, the invention contemplates the use of a "mini-E1A gene product" comprising less than the entire E1A amino acid sequence. For example, such a mini-E1A gene product may comprise the N-terminal domain and the CR1 domain of an E1A gene product. Such a mini-E1A gene product may further comprise a spacer domain and/or a C-terminal domain of the E1A-gene product. Other preferred mini-E1A gene products are E1A gene products from which the CR2 region has been ablated.

The term "E1A gene" refers to any DNA sequence that is substantially identical to a DNA sequence encoding an E1A gene product as defined above. The term also refers to RNA, or antisense sequences compatible with such DNA sequences. An "E1A gene" may also comprise any combination of associated control sequences.

The term "substantially identical", when used to define either an E1A amino acid sequence or E1A gene nucleic acid sequence, means that a particular subject sequence, for example, a mutant sequence, varies from the sequence of natural E1A by one or more substitutions, deletions, or additions, the net effect of which is to retain at least some biological activity of the E1A protein. Alternatively, DNA analog sequences are "substantially identical" to specific DNA sequences disclosed herein if: (a) the DNA analog sequence is derived from coding regions of the natural E1A gene; or (b) the DNA analog sequence is capable of hybridization of DNA sequences of (a) under moderately stringent conditions and which encode biologically active E1A; or (c) DNA sequences which are degenerative as a result of the genetic code to the DNA analog sequences defined in (a) or (b). Substantially identical analog proteins will be greater than about 80% similar to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequence.

LT Gene Products and Genes

In this patent the terms "LT gene product" and "LT" refers to proteins having amino acid sequences which are substantially identical to the native LT amino acid sequence and which are biologically active in that they are capable of binding to Rb, suppressing neu oncogene-mediated transformation, immortalizing cells, inducing anchorage independency, or cross-reacting with anti-LT antibody raised against LT. Such sequences are disclosed, for example, in Tooze—*Molecular Biology of the Tumor Viruses*, Fiers et al., 1978, and Reddy et al. 1978. The term "LT gene product" also includes analogs of LT molecules which exhibit at least some biological activity in common with native LT. Examples of such LT analogs are K1 and K7, which are defective for transformation of cells (Kalderon et al., 1984). Many other exemplary LT analogs are disclosed in Kalderon et al. 1984, particularly in Table 2. Furthermore, those skilled in the art of mutagenesis will appreciate that other analogs, as yet undisclosed or undiscovered, may be used to construct LT analogs. There is no need for an "LT gene product" or "LT" to comprise all, or substantially all of the amino acid sequence of the native LT gene. Shorter or longer sequences are anticipated to be of use in the invention.

The term "LT gene" refers to any DNA sequence that is substantially identical to a DNA sequence encoding an LT gene product as defined above. The term also refers to RNA, or antisense sequences compatible with such DNA sequences. An "LT gene" may also comprise any combination of associated control sequences.

The term "substantially identical", when used to define either an LT amino acid sequence or an LT nucleic acid sequence, means that a particular subject sequence, for example, a mutant sequence, varies from the sequence of natural LT by one or more substitutions, deletions, or additions, the net effect of which is to retain at least some biological activity of the LT protein. Alternatively, DNA analog sequences are "substantially identical" to specific DNA sequences disclosed herein if: (a) the DNA analog sequence is derived from coding regions of the natural LT gene; or (b) the DNA analog sequence is capable of hybridization of DNA sequences of (a) under moderately stringent conditions and which encode biologically active LT; or (c) DNA sequences which are degenerative as a result of the genetic code to the DNA analog sequences defined in (a) or (b). Substantially identical analog proteins will be greater than about 80% similar to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequence.

Percent Similarity

Percent similarity may be determined, for example, by comparing sequence information using the GAP computer program, available from the University of Wisconsin Geneticist Computer Group. The GAP program utilizes the alignment method of Needleman et al., 1970, as revised by Smith et al., 1981. Briefly, the GAP program defines similarity as the number of aligned symbols (i.e. nucleotides or amino acids) which are similar, divided by the total number of symbols in the shorter of the two sequences. The preferred default parameters for the GAP program include (1) a unitary comparison matrix (containing a value of 1 for identities and 0 for non-identities) of nucleotides and the weighted comparison matrix of Gribskov et al., 1986, as described by Schwartz et al., 1979; (2) a penalty of 3.0 for each gap and an additional 0.01 penalty for each symbol and each gap; and (3) no penalty for end gaps.

Nucleic Acid Sequences

In certain embodiments, the invention concerns the use of neu-suppressing genes and gene products, such as the LT antigen gene product or the E1A gene product, or both, that include within their respective sequences a sequence which is essentially that of the known LT antigen gene or E1A gene, or the corresponding proteins. The term "a sequence essentially as that of LT antigen or E1A" means that the sequence substantially corresponds to a portion of the LT antigen or E1A gene and has relatively few bases or amino acids (whether DNA or protein) which are not identical to those of LT or E1A (or a biologically functional equivalent thereof, when referring to proteins). The term "biologically functional equivalent" is well understood in the art and is further defined in detail herein. Accordingly, sequences which have between about 70% and about 80%; or more preferably, between about 81% and about 90%; or even more preferably, between about 91% and about 99%; of amino acids which are identical or functionally equivalent to the amino acids of LT antigen or E1A will be sequences which are "essentially the same".

LT antigen and E1A genes which have functionally equivalent codons are also covered by the invention. The term "functionally equivalent codon" is used herein to refer to codons that encode the same amino acid, such as the six codons for arginine or serine, and also refers to codons that encode biologically equivalent amino acids (Table 1).

TABLE 1

FUNCTIONALLY EQUIVALENT CODONS.

| Amino Acids | | | Codons | | | |
|---|---|---|---|---|---|---|
| Alanine | Ala | A | GCA GCC | GCG | GCU | |
| Cysteine | Cys | C | UGC UGU | | | |
| Aspartic Acid | Asp | D | GAC GAU | | | |
| Glutamic Acid | Glu | E | GAA GAG | | | |
| Phenylalanine | Phe | F | UUC UUU | | | |
| Glycine | Gly | G | GGA GGC | GGG | GGU | |
| Histidine | His | H | CAC CAU | | | |
| Isoleucine | Ile | I | AUA AUC | AUU | | |
| Lysine | Lys | K | AAA AAG | | | |
| Leucine | Leu | L | UUA UUG | CUA | CUC | CUG CUU |
| Methionine | Met | M | AUG | | | |
| Asparagine | Asn | N | AAC AAU | | | |
| Proline | Pro | P | CCA CCC | CCU | | |
| Glutamine | Gln | Q | CAA CAG | | | |
| Arginine | Arg | R | AGA AGG | CGA | CGC | CGG CGU |
| Serine | Ser | S | AGC AGU | UCA | UCC | UCG UCU |
| Threonine | Thr | T | ACA ACC | ACG | ACU | |
| Valine | Val | V | GUA GUC | GUG | GUU | |
| Tryptophan | Trp | W | UGG | | | |
| Tyrosine | Tyr | Y | UAC UAU | | | |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

The present invention also encompasses the use of DNA segments which are complementary, or essentially complementary, to the sequences set forth in the specification. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment in question under relatively stringent conditions such as those described herein.

Biologically Functional Equivalents

As mentioned above, modification and changes may be made in the structure of E1A or LT and still obtain a molecule having like or otherwise desirable characteristics. For example, certain amino acids may be substituted for other amino acids in a protein structure without appreciable loss of interactive binding capacity with structures such as, for example, the neu-gene. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated by the inventors that various changes may be made in the sequence of the E1A or LT proteins or peptides (or underlying DNA) without appreciable loss of their biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged. This is the case in the present invention, where it any changes in the neu-binding region of either E1A or LT that render the peptide incapable of suppressing neu-mediated transformation would result in a loss of utility of the resulting peptide for the present invention.

Amino acid substitutions, such as those which might be employed in modifying either E1A or LT are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

Sequence Modification Techniques

Modifications to the E1A and LT peptides may be carried out using techniques such as site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes the E1A gene or the LT gene. An oligonucleotide primer bearing the desired mutated sequence is prepared, generally synthetically, for example by the method of Crea el al. (1978). This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

Kalderon et al. (1984) report several mutagenic methods which have proved useful in mutating the native LT gene. Specifically, Kalderon et al. teach deletion mutations by displacement-loop mutagenesis and by the random insertion of EcoRI linkers into the LT gene. Further, point mutation by deletion-loop mutagenesis is taught. The reference also teaches screening procedures for determining the success of such mutations. The teachings of Kalderon et al. (1984) are incorporated by reference in this application.

The preparation of sequence variants of the selected gene using site-directed mutagenesis is provided as a means of producing potentially useful E1A, LT, or other neu-suppressing species and is not meant to be limiting as there are other ways in which sequence variants of these peptides may be obtained. For example, recombinant vectors encoding the desired genes may be treated with mutagenic agents to obtain sequence variants (see, e.g., a method described by Eichenlaub, 1979) for the mutagenesis of plasmid DNA using hydroxylamine.

Other Structural Equivalents

In addition to the E1A and LT peptidyl compounds described herein, the inventors also contemplate that other sterically similar compounds may be formulated to mimic the key portions of the peptide structure. Such compounds may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

B. Chemotherapeutic Agents

A wide variety of chemotherapeutic agents may be used in combination with the therapeutic genes of the present invention. These can be, for example, agents that directly cross-link DNA, agents that intercalate into DNA, and agents that lead to chromosomal and mitotic aberrations by affecting nucleic acid synthesis.

Agents that directly cross-link nucleic acids, specifically DNA, are envisaged and are shown herein, to eventuate DNA damage leading to a synergistic antineoplastic combination. Agents such as cisplatin, and other DNA alkylating agents may be used.

Agents that damage DNA also include compounds that interfere with DNA replication, mitosis, and chromosomal segregation. Examples of these compounds include adriamycin (also known as doxorubicin), VP-16 (also known as etoposide), verapamil, podophyllotoxin, and the like. Widely used in clinical setting for the treatment of neoplasms these compounds are administered through bolus injections intravenously at doses ranging from 25–75 mg/m$^2$ at 21 day intervals for adriamycin, to 35–100 mg/m$^2$ for etoposide intravenously or orally.

(i) Antibiotics

Doxorubicin

Doxorubicin hydrochloride, 5,12-Naphthacenedione, (8s-cis)-10-[(3-amino-2,3,6-trideoxy-a-L-lyxo-hexopyranosyl) oxy]-7,8,9,10-tetrahydro-6,8,11-trihydroxy-8-(hydroxyacetyl)-1-methoxy-hydrochloride (hydroxydaunorubicin hydrochloride, Adriamycin) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of ovarian, endometrial and breast tumors, bronchogenic oat-cell carcinoma, non-small cell lung carcinoma, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkinds disease, adrenal tumors, osteogenic sarcoma soft tissue sarcoma, Ewing's sarcoma, rhabdomyosarcoma and acute lymphocytic leukemia. It is an alternative drug for the treatment of islet cell, cervical, testicular and adrenocortical cancers. It is also an immunosuppressant.

Doxorubicin is absorbed poorly and must be administered intravenously. The pharmacokinetics are multicompartmental. Distribution phases have half-lives of 12 minutes and 3.3 hr. The elimination half-life is about 30 hr. Forty to 50% is secreted into the bile. Most of the remainder is metabolized in the liver, partly to an active metabolite (doxorubicinol), but a few percent is excreted into the urine. In the presence of liver impairment, the dose should be reduced.

Appropriate doses are, intravenous, adult, 60 to 75 mg/m$^2$ at 21-day intervals or 25 to 30 mg/m$^2$ on each of 2 or 3 successive days repeated at 3- or 4-wk intervals or 20 mg/m$^2$ once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/m$^2$ in patients with normal heart function and 400 mg/m$^2$ in persons having received mediastinal irradiation. Alternatively, 30 mg/m$^2$ on each of 3 consecutive days, repeated every 4 wk. Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

In the present invention the inventors have employed E1A and LT as exemplary genes for therapy to synergistically enhance the antineoplastic effects of the doxorubicin in the treatment of cancers. Those of skill in the art will be able to use the invention as exemplified potentiate the effects of doxorubicin in a range of different neu-mediated cancers.

Daunorubicin

Daunorubicin hydrochloride, 5,12-Naphthacenedione, (8S-cis)-8-acetyl-10-[(3amino-2,3,6-trideoxy-a-L-lyxo-hexanopyranosyl)oxy]-7,8,9,10-tetrahydro-6,8,11-trihydroxy-10-methoxy-, hydrochloride; also termed cerubidine and available from Wyeth. Daunorubicin intercalates into DNA, blocks DAN-directed RNA polymerase and inhibits DNA synthesis. It can prevent cell division in doses that do not interfere with nucleic acid synthesis.

In combination with other drugs it is included in the first-choice chemotherapy of acute myelocytic leukemia in adults (for induction of remission), acute lymphocytic leukemia and the acute phase of chronic myelocytic leukemia. Oral absorption is poor, and it must be given intravenously. The half-life of distribution is 45 minutes and of elimination, about 19 hr. The half-life of its active metabolite, daunorubicinol, is about 27 hr. Daunorubicin is metabolized mostly in the liver and also secreted into the bile (ca 40%). Dosage must be reduced in liver or renal insufficiencies.

Suitable doses are (base equivalent), intravenous adult, younger than 60 yr. 45 mg/m$^2$/day (30 mg/m$^2$ for patients older than 60 yr.) for 1, 2 or 3 days every 3 or 4 wk or 0.8 mg/kg/day for 3 to 6 days every 3 or 4 wk; no more than 550 mg/m$^2$ should be given in a lifetime, except only 450 mg/m$^2$ if there has been chest irradiation; children, 25 mg/m$^2$ once a week unless the age is less than 2 yr. or the body surface less than 0.5 m, in which case the weight-based adult schedule is used. It is available in injectable dosage forms (base equivalent) 20 mg (as the base equivalent to 21.4 mg of the hydrochloride). Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

Mitomycin

Mitomycin (also known as mutamycin and/or mitomycin-C) is an antibiotic isolated from the broth of *Streptomyces caespitosus* which has been shown to have antitumor activity. The compound is heat stable, has a high melting point, and is freely soluble in organic solvents.

Mitomycin selectively inhibits the synthesis of deoxyribonucleic acid (DNA). The guanine and cytosine content correlates with the degree of mitomycin-induced cross-linking. At high concentrations of the drug, cellular RNA and protein synthesis are also suppressed.

In humans, mitomycin is rapidly cleared from the serum after intravenous administration. Time required to reduce the serum concentration by 50% after a 30 mg. bolus injection is 17 minutes. After injection of 30 mg., 20 mg., or 10 mg. I.V., the maximal serum concentrations were 2.4 mg./mL, 1.7 mg./mL, and 0.52 mg./mL, respectively. Clearance is effected primarily by metabolism in the liver, but metabolism occurs in other tissues as well. The rate of clearance is inversely proportional to the maximal serum concentration because, it is thought, of saturation of the degradative pathways.

Approximately 10% of a dose of mitomycin is excreted unchanged in the urine. Since metabolic pathways are saturated at relatively low doses, the percent of a dose excreted in urine increases with increasing dose. In children, excretion of intravenously administered mitomycin is similar.

Actinomycin D

Actinomycin D (Dactinomycin) [50-76-0]; $C_{62}H_{86}N_{12}O_{16}$ (1255.43) is an antineoplastic drug that inhibits DNA-dependent RNA polymerase. It is a component of first-choice combinations for treatment of choriocarcinoma, embryonal rhabdomyosarcoma, testicular tumor and Wilms' tumor. Tumors which fail to respond to systemic treatment sometimes respond to local perfusion. Dactinomycin potentiates radiotherapy. It is a secondary (efferent) immunosuppressive.

Actinomycin D is used in combination with primary surgery, radiotherapy, and other drugs, particularly vincristine and cyclophosphamide. Antineoplastic activity has also been noted in Ewing's tumor, Kaposi's sarcoma, and soft-tissue sarcomas. Dactinomycin can be effective in women with advanced cases of choriocarcinoma. It also produces consistent responses in combination with chlorambucil and methotrexate in patients with metastatic testicular carcinomas. A response may sometimes be observed in patients with Hodgkin's disease and non-Hodgkin's lymphomas. Dactinomycin has also been used to inhibit immunological responses, particularly the rejection of renal transplants.

Half of the dose is excreted intact into the bile and 10% into the urine; the half-life is about 36 hr. The drug does not pass the blood-brain barrier. Actinomycin D is supplied as a lyophilized powder (0/5 mg in each vial). The usual daily dose is 10 to 15 mg/kg; this is given intravenously for 5 days; if no manifestations of toxicity are encountered, additional courses may be given at intervals of 3 to 4 weeks. Daily injections of 100 to 400 mg have been given to children for 10 to 14 days; in other regimens, 3 to 6 mg/kg, for a total of 125 mg/kg, and weekly maintenance doses of 7.5 mg/kg have been used. Although it is safer to administer the drug into the tubing of an intravenous infusion, direct intravenous injections have been given, with the precaution of discarding the needle used to withdraw the drug from the vial in order to avoid subcutaneous reaction. Exemplary doses may be 100 mg/m$^2$, 150 mg/m, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

Bleomycin

Bleomycin is a mixture of cytotoxic glycopeptide antibiotics isolated fromn a strain of *Streptomyces verticillus*. It is freely soluble in water.

Although the exact mechanism of action of bleomycin is unknown, available evidence would seem to indicate that the main mode of action is the inhibition of DNA synthesis with some evidence of lesser inhibition of RNA and protein synthesis.

In mice, high concentrations of bleomycin are found in the skin, lungs, kidneys, peritoneum, and lymphatics. Tumor cells of the skin and lungs have been found to have high concentrations of bleomycin in contrast to the low concentrations found in hematopoietic tissue. The low concentrations of bleomycin found in bone marrow may be related to high levels of bleomycin degradative enzymes found in that tissue.

In patients with a creatinine clearance of >35 mL per minute, the serum or plasma terminal elimination half-life of bleomycin is approximately 115 minutes. In patients with a creatinine clearance of <35 mL per minute, the plasma or serum terminal elimination half-life increases exponentially as the creatinine clearance decreases. In humans, 60% to 70% of an administered dose is recovered in the urine as active bleomycin.

Bleomycin should be considered a palliative treatment. It has been shown to be useful in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), skin, penis, cervix, and vulva. It has also been used in the treatment of lymphomas and testicular carcinoma.

Because of the possibility of an anaphylactoid reaction, lymphoma patients should be treated with two units or less for the first two doses. If no acute reaction occurs, then the regular dosage schedule may be followed.

Improvement of Hodgkin's Disease and testicular tumors is prompt and noted within 2 weeks. If no improvement is seen by this time, improvement is unlikely. Squamous cell cancers respond more slowly, sometimes requiring as long as 3 weeks before any improvement is noted.

Bleomycin may be given by the intramuscular, intravenous, or subcutaneous routes.

(ii) Miscellaneous Agents

Cisplatin

Cisplatin has been widely used to treat cancers such as metastatic testicular or ovarian carcinoma, advanced bladder cancer, head or neck cancer, cervical cancer, lung cancer or other tumors. Cisplatin can be used alone or in combination with other agents, with efficacious doses used in clinical applications of 15–20 mg/m$^2$ for 5 days every three weeks for a total of three courses. Exemplary doses may be 0.50 mg/m$^2$, 1.0 mg/m$^2$, 1.50 mg/m$^2$, 1.75 mg/m$^2$, 2.0 mg/m$^2$, 3.0 mg/m$^2$, 4.0 mg/m$^2$, 5.0 mg/m$^2$, 10 mg/m$^2$. Of course, all of these dosages are exemplary, and any dosage in-between these points is also expected to be of use in the invention.

Cisplatin is not absorbed orally and must therefore be delivered via injection intravenously, subcutaneously, intratumorally or intraperitoneally.

In certain aspects of the current invention cisplatin may be used in combination with E1A or LT in the treatment of breast carcinoma. It is clear, however, that the combination of cisplatin and therapeutic genes could be used for the treatment of any other neu-mediated cancer.

VP16

VP16 is also know as etoposide and is used primarily for treatment of testicular tumors, in combination with bleomycin and cisplatin, and in combination with cisplatin for small-cell carcinoma of the lung. It is also active against non-Hodgkin's lymphomas, acute nonlymphocytic leukemia, carcinoma of the breast, and Kaposi's sarcoma associated with acquired immunodeficiency syndrome (AIDS).

VP16 is available as a solution (20 mg/ml) for intravenous administration and as 50-mg, liquid-filled capsules for oral use. For small-cell carcinoma of the lung, the intravenous dose (in combination therapy) is can be as much as 100 mg/m$^2$ or as little as 2 mg/m$^2$, routinely 35 mg/m$^2$, daily for 4 days, to 50 mg/m$^2$, daily for 5 days have also been used. When given orally, the dose should be doubled. Hence the doses for small cell lung carcinoma may be as high as 200–250 mg/m$^2$. The intravenous dose for testicular cancer (in combination therapy) is 50 to 100 mg/m$^2$ daily for 5 days, or 100 mg/m$^2$ on alternate days, for three doses. Cycles of therapy are usually repeated every 3 to 4 weeks. The drug should be administered slowly during a 30- to 60-minute infusion in order to avoid hypotension and bronchospasm, which are probably due to the solvents used in the formulation.

Tumor Necrosis Factor

Tumor Necrosis Factor [TNF; Cachectin] is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-α also has been found to possess anti-cancer activity.

(iii) Plant Alkaloids

Taxol

Taxol is an experimental antimitotic agent, isolated from the bark of the ash tree, *Taxus brevifolia*. It binds to tubulin (at a site distinct from that used by the vinca alkaloids) and promotes the assembly of microtubules. Taxol is currently being evaluated clinically; it has activity against malignant melanoma and carcinoma of the ovary. Maximal doses are 30 mg/m$^2$ per day for 5 days or 210 to 250 mg/m$^2$ given once every 3 weeks. Of course, all of these dosages are exemplary, and any dosage in-between these points is also expected to be of use in the invention.

Vincristine

Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

The relatively low toxicity of vincristine for normal marrow cells and epithelial cells make this agent unusual among anti-neoplastic drugs, and it is often included in combination with other myelosuppressive agents.

Unpredictable absorption has been reported after oral administration of vinblastine or vincristine. At the usual clinical doses the peak concentration of each drug in plasma is approximately 0.4 mM.

Vinblastine and vincristine bind to plasma proteins. They are extensively concentrated in platelets and to a lesser extent in leukocytes and erythrocytes.

Vincristine has a multiphasic pattern of clearance from the plasma; the terminal half-life is about 24 hours. The drug is metabolized in the liver, but no biologically active derivatives have been identified. Doses should be reduced in patients with hepatic dysfunction. At least a 50% reduction in dosage is indicated if the concentration of bilirubin in plasma is greater than 3 mg/dl (about 50 mM).

Vincristine sulfate is available as a solution (1 mg/ml) for intravenous injection. Vincristine used together with corticosteroids is presently the treatment of choice to induce remissions in childhood leukemia; the optimal dosages for these drugs appear to be vincristine, intravenously, 2 mg/m$^2$ of body-surface area, weekly, and prednisone, orally, 40 mg/m$^2$, daily. Adult patients with Hodgkin's disease or non-Hodgkin's lymphomas usually receive vincristine as a part of a complex protocol. When used in the MOPP regimen, the recommended dose of vincristine is 1.4 mg/m$^2$. High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine has been effective in Hodgkin's disease and other lymphomas. Although it appears to be somewhat less beneficial than vinblastine when used alone in Hodgkin's disease, when used with mechlorethamine, prednisone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisone. Vincristine is more useful than vinblastine in lymphocytic leukemia. Beneficial response have been reported in patients with a variety of other neoplasms, particularly Wilnis' tumor, neuroblastoma, brain tumors, rhabdomyosarcoma, and carcinomas of the breast, bladder, and the male and female reproductive systems.

Doses of vincristine for use will be determined by the clinician according to the individual patients need. 0.01 to 0.03 mg/kg or 0.4 to 1.4 mg/m$^2$ can be administered or 1.5 to 2 mg/m$^2$ can also be administered. Alternatively 0.02 mg/m$^2$, 0.05 mg/m$^2$, 0.06 mg/m$^2$, 0.07 mg/m$^2$, 0.08 mg/m$^2$, 0.1 mg/m$^2$, 0.12 mg/m$^2$, 0.14 mg/m$^2$, 0.15 mg/m$^2$, 0.2 mg/m$^2$, 0.25 mg/m$^2$ can be given as a constant intravenous infusion. Of course, all of these dosages are exemplary, and any dosage in-between these points is also expected to be of use in the invention.

Vinblastine

When cells are incubated with vinblastine, dissolution of the microtubules occurs. Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes.

After intravenous injection, vinblastine has a multiphasic pattern of clearance from the plasma; after distribution, drug disappears from plasma with half-lives of approximately 1 and 20 hours.

Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 mM).

Vinblastine sulfate is available in preparations for injection. The drug is given intravenously; special precautions must be taken against subcutaneous extravasation, since this may cause painful irritation and ulceration. The drug should not be injected into an extremity with impaired circulation. After a single dose of 0.3 mg/kg of body weight, myelosuppression reaches its maximum in 7 to 10 days: If a moderate level of leukopenia (approximately 3000 cells/mm$^3$) is not attained, the weekly dose may be increased gradually by increments of 0.05 mg/kg of body weight. In regimens designed to cure testicular cancer, vinblastine is used in doses of 0.3 mg/kg every 3 weeks irrespective of blood cell counts or toxicity.

The most important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, neuroblastoma, and Letterer-Siwe disease (histiocytosis X), as well as in carcinoma of the breast and choriocarcinoma in women.

Doses of vinblastine for use will be determined by the clinician according to the individual patients need. 0.1 to 0.3 mg/kg can be administered or 1.5 to 2 mg/m$^2$ can also be administered. Alternatively, 0.1 mg/m$^2$, 0.12 mg/m$^2$, 0.14 mg/m$^2$, 0.15 mg/m$^2$, 0.2 mg/m$^2$, 0.25 mg/m$^2$, 0.5 mg/m$^2$, 1.0 mg/m$^2$, 1.2 mg/m$^2$, 1.4 mg/m$^2$, 1.5 mg/m$^2$, 2.0 mg/m$^2$, 2.5 mg/m$^2$, 5.0 mg/m$^2$, 6 mg/m$^2$, 8 mg/m$^2$, 9 mg/m$^2$, 10 mg/m$^2$, 20 mg/m$^2$, can be given. Of course, all of these dosages are exemplary, and any dosage in-between these points is also expected to be of use in the invention.

(iv) Alkylating Agents

Carmustine

Carmustine (sterile carmustine) is one of the nitrosoureas used in the treatment of certain neoplastic diseases. It is 1,3 bis (2-chloroethyl)-1-nitrosourea. It is lyophilized pale yellow flakes or congealed mass with a molecular weight of 214.06. It is highly soluble in alcohol and lipids, and poorly soluble in water. Carmustine is administered by intravenous infusion after reconstitution as recommended. Sterile carmustine is commonly available in 100 mg single dose vials of lyophilized material.

Although it is generally agreed that carmustine alkylates DNA and RNA, it is not cross resistant with other alkylators. As with other nitrosoureas, it may also inhibit several key enzymatic processes by carbamoylation of amino acids in proteins.

Carmustine is indicated as palliative therapy as a single agent or in established combination therapy with other approved chemotherapeutic agents in brain tumors such as glioblastoma, brainstem glioma, medullobladyoma, astrocytoma, ependymoma, and metastatic brain tumors. Also it has been used in combination with prednisone to treat multiple myeloma. Carmustine has proved useful, in the treatment of Hodgkin's Disease and in non-Hodgkin's lymphomas, as secondary therapy in combination with other approved drugs in patients who relapse while being treated with primary therapy, or who fail to respond to primary therapy.

The recommended dose of carmustine as a single agent in previously untreated patients is 150 to 200 mg/m$^2$ intravenously every 6 weeks. This may be given as a single dose or divided into daily injections such as 75 to 100 mg/m$^2$ on 2 successive days. When carmustine is used in combination with other myelosuppressive drugs or in patients in whom bone marrow reserve is depleted, the doses should be adjusted accordingly. Doses subsequent to the initial dose should be adjusted according to the hematologic response of the patient to the preceding dose. It is of course understood that other doses may be used in the present invention for example 10 mg/m², 20 mg/m², 30 mg/m² 40 mg/² 50 mg/m² 60 mg/m² 70 mg/m² 80 mg/m² 90 mg/m² 100 mg/m². The skilled artisan is directed to, "Remington's Pharmaceutical Sciences" 15th Edition, chapter 61. Some variation in dosage will necessarily occur depending on the condition of the subject being treated. The person responsible for administration will, in any event, determine the appropriate dose for the individual subject.

Melphalan

Melphalan also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. It is known chemically as 4-[bis(2-chloroethyl)amino]-L-phenylalanine.

Melphalan is the active L-isomer of the compound and was first synthesized in 1953 by Bergel and Stock; the D-isomer, known as medphalan, is less active against certain animal tumors, and the dose needed to produce effects on chromosomes is larger than that required with the L-isomer. The racemic (DL-) form is known as merphalan or sarcolysin. Melphalan is insoluble in water and has a $pKa_1$ of ~2.1. Melphalan is available in tablet form for oral administration and has been used to treat multiple myeloma.

Available evidence suggests that about one third to one half of the patients with multiple myeloma show a favorable response to oral administration of the drug.

Melphalan has been used in the treatment of epithelial ovarian carcinoma. One commonly employed regimen for the treatment of ovarian carcinoma has been to administer melphalan at a dose of 0.2 mg/kg daily for five days as a single course. Courses are repeated every four to five weeks depending upon hematologic tolerance (Smith and Rutledge, 1975; Young et al., 1978). Alternatively the dose of melphalan used could be as low as 0.05 mg/kg/day or as high as 3 mg/kg/day or any dose in between these doses or above these doses. Some variation in dosage will necessarily occur depending on the condition of the subject being treated. The person responsible for administration will, in any event, determine the appropriate dose for the individual subject.

Cyclophosphamide

Cyclophosphamide is 2H-1,3,2-Oxazaphosphorin-2-amine, N,N-bis(2-chloroethyl)tetrahydro-, 2-oxide, monohydrate; termed Cytoxan available from Mead Johnson; and Neosar available from Adria. Cyclophosphamide is prepared by condensing 3-amino-1-propanol with N,N-bis(2-chlorethyl) phosphoramidic dichloride [(ClCH$_2$CH$_2$)$_2$N—POCl$_2$] in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parental routes and does not cause local vesication, necrosis, phlebitis or even pain.

Suitable doses for adults include, orally, 1 to 5 mg/kg/day (usually in combination), depending upon gastrointestinal tolerance; or 1 to 2 mg/kg/day; intravenously, initially 40 to 50 mg/kg in divided doses over a period of 2 to 5 days or 10 to 15 mg/kg every 7 to 10 days or 3 to 5 mg/kg twice a week or 1.5 to 3 mg/kg/day. A dose 250 mg/kg/day may be administered as an antineoplastic. Because of gastrointestinal adverse effects, the intravenous route is preferred for loading. During maintenance, a leukocyte count of 3000 to 4000/mm³ usually is desired. The drug also sometimes is administered intramuscularly, by infiltration or into body cavities. It is available in dosage forms for injection of 100, 200 and 500 mg, and tablets of 25 and 50 mg the skilled artisan is referred to "Remington's Pharmaceutical Sciences" 15th Edition, chapter 61, incorporate herein as a reference, for details on doses for administration.

Chlorambucil

Chlorambucil (also known as leukeran) was first synthesized by Everett et al. (1953). It is a bifunctional alkylating agent of the nitrogen mustard type that has been found active against selected human neoplastic diseases. Chlorambucil is known chemically as 4-[bis(2-chlorethyl)amino] benzenebutanoic acid.

Chlorambucil is available in tablet form for oral administration. It is rapidly and completely absorbed from the gastrointestinal tract. After single oral doses of 0.6–1.2 mg/kg, peak plasma chlorambucil levels are reached within one hour and the terminal half-life of the parent drug is estimated at 1.5 hours. 0.1 to 0.2 mg/kg/day or 3 to 6 mg/m²/day or alternatively 0.4 mg/kg may be used for antineoplastic treatment. Treatment regimes are well know to those of skill in the art and can be found in the "Physicians Desk Reference" and in "Remingtons Pharmaceutical Sciences" referenced herein.

Chlorambucil is indicated in the treatment of chronic lymphatic (lymphocytic) leukemia, malignant lymphomas including lymphosarcoma, giant follicular lymphoma and Hodgkin's disease. It is not curative in any of these disorders but may produce clinically useful palliation.

Busulfan

Busulfan (also known as myleran) is a bifunctional alkylating agent. Busulfan is known chemically as 1,4-butanediol dimethanesulfonate.

Busulfan is not a structural analog of the nitrogen mustards. Busulfan is available in tablet form for oral administration. Each scored tablet contains 2 mg busulfan and the inactive ingredients magnesium stearate and sodium chloride.

Busulfan is indicated for the palliative treatment of chronic myelogenous (myeloid, myelocytic, granulocytic) leukemia. Although not curative, busulfan reduces the total granulocyte mass, relieves symptoms of the disease, and improves the clinical state of the patient. Approximately 90% of adults with previously untreated chronic myelogenous leukemia will obtain hematologic remission with regression or stabilization of organomegaly following the use of busulfan. It has been shown to be superior to splenic irradiation with respect to survival times and maintenance of hemoglobin levels, and to be equivalent to irradiation at controlling splenomegaly.

Lomustine

Lomustine is one of the nitrosoureas used in the treatment of certain neoplastic diseases. It is 1-(2-chloro-ethyl)-3-cyclohexyl-1 nitrosourea. It is a yellow powder with the empirical formula of $C_9H_{16}ClN_3O_2$ and a molecular weight of 233.71. Lomustine is soluble in 10% ethanol (0.05 mg per mL) and in absolute alcohol (70 mg per mL). Lomustine is relatively insoluble in water (<0.05 mg per mL). It is relatively unionized at a physiological pH. Inactive ingredients in lomustine capsules are: magnesium stearate and mannitol.

Although it is generally agreed that lomustine alkylates DNA and RNA, it is not cross resistant with other alkylators. As with other nitrosoureas, it may also inhibit several key enzymatic processes by carbamoylation of amino acids in proteins.

Lomustine may be given orally. Following oral administration of radioactive lomustine at doses ranging from 30 mg/m$^2$ to 100 mg/m$^2$, about half of the radioactivity given was excreted in the form of degradation products within 24 hours.

The serum half-life of the metabolites ranges from 16 hours to 2 days. Tissue levels are comparable to plasma levels at 15 minutes after intravenous administration.

Lomustine has been shown to be useful as a single agent in addition to other treatment modalities, or in established combination therapy with other approved chemotherapeutic agents in both primary and metastatic brain tumors, in patients who have already received appropriate surgical and/or radiotherapeutic procedures. It has also proved effective in secondary therapy against Hodgkin's Disease in combination with other approved drugs in patients who relapse while being treated with primary therapy, or who fail to respond to primary therapy.

The recommended dose of lomustine in adults and children as a single agent in previously untreated patients is 130 mg/m$^2$ as a single oral dose every 6 weeks. In individuals with compromised bone marrow function, the dose should be reduced to 100 mg/m$^2$ every 6 weeks. When lomustine is used in combination with other myelosuppressive drugs, the doses should be adjusted accordingly. It is understood that other doses may be used for example, 20 mg/m$^2$ 30 mg/m$^2$, 40 mg/m$^2$, 50 mg/m$^2$, 60 mg/m$^2$, 70 mg/m$^2$, 80 mg/m$^2$, 90 mg/m$^2$, 100 mg/m$^2$, 120 mg/m$^2$ or any doses between these FIGS. as determined by the clinician to be necessary for the individual being treated.

C. Pharmaceutical Compositions and Routes of Administration

Compositions of the present invention will have an effective amount of a gene for therapeutic administration in combination with an effective amount of a compound (second agent) that is a chemotherapeutic agent as exemplified above. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants and the like.

The expression vectors and delivery vehicles of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The vectors of the present invention are advantageously administered in the form of injectable compositions either as liquid solutions or suspensions; solid forms suitable for solution in, or suspension in, liquid prior to injection also may be prepared. These preparations also may be emulsified. A typical compositions for such purposes comprises a 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters, such as theyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

All the essential materials and reagents required for inhibiting tumor cell proliferation may be assembled together in a kit. When the components of the kit are provided in one or more liquid solutions, the liquid solution preferably is an aqueous solution, with a sterile aqueous solution being particularly preferred.

For in vivo use, a chemotherapeutic agent may be formulated into a single or separate pharmaceutically acceptable syringeable composition. In this case, the container means may itself be an inhalant, syringe, pipette, eye dropper, or other such like apparatus, from which the formulation may be applied to an infected area of the body, such as the lungs, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the gene therapy and/or the chemotherapeutic drug.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle.

Parenteral Administration

The active compounds of the present invention will often be formulated for parenteral administration, e.g., formulated for injection via the intravenous, intramuscular, sub-cutaneous, or even intraperitoneal routes. The preparation of an aqueous composition that contains a second agent(s) as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

D. In vivo Delivery and Treatment Protocols

Where the gene itself is employed to introduce the gene products, a convenient method of introduction will be through the use of a recombinant vector which incorporates the desired gene, together with its associated control sequences. The preparation of recombinant vectors is well known to those of skill in the art and described in many references, such as, for example, Sambrook et al. (1989), specifically incorporated herein by reference.

In vectors, it is understood that the DNA coding sequences to be expressed, in this case those encoding the neu-suppressing gene products, are positioned adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One may also desire to incorporate into the transcriptional unit of the vector an appropriate polyadenylation site (e.g., 5'-AATAAA-3'), if one was not contained within the original inserted DNA. Typically, these poly A addition sites are placed about 30 to 2000 nucleotides "downstream" of the coding sequence at a position prior to transcription termination.

While use of the control sequences of the specific gene (i.e., the E1A promoter for E1A and the LT promoter for LT) will be preferred, there is no reason why other control sequences could not be employed, so long as they are compatible with the genotype of the cell being treated. Thus, one may mention other useful promoters by way of example, including, e.g., an SV40 early promoter, a long terminal repeat promoter from retrovirus, an actin promoter, a heat shock promoter, a metallothionein promoter, and the like.

For introduction of the E1A or LT gene, it is proposed that one will desire to preferably employ a vector construct that will deliver the desired gene to the affected cells. This will, of course, generally require that the construct be delivered to the targeted tumor cells, for example, breast, genital, or lung tumor cells. It is proposed that this may be achieved most preferably by introduction of the desired gene through the use of a viral vector to carry either the E1A or LT sequences to efficiently infect the tumor, or pretumorous tissue. These vectors will preferably be an adenoviral, a retroviral, a vaccinia viral vector or adeno-associated virus. These vectors are preferred because they have been successfully used to deliver desired sequences to cells and tend to have a high infection efficiency.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bg1 I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

A particularly desirable vector, at least as a starting point, is the E1A containing retroviral vector, termed pSVXE1A-G, described by Robert et al., 1985. This vector comprises the E1A gene which has been brought under the control of the SV-40 early promoter. For LT expression, the pZ189 (driven by the SV-80 promoter) and the pVU-O vectors both contain LT. LT mutants are contained in, for example, pK1 and pK7 as well as other vectors described by Kalderon et al. 1984. The inventors propose that these constructs could either be used directly in the practice of the invention, or could be used as a starting point for the introduction of other more desirable promoters such as those discussed above.

(i) Adenovirus

One of the preferred methods for in vivo delivery involves the use of an adenovirus vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized. Adenoviral transfer of E1A is especially useful, because E1A is itself an adenoviral gene. Therefore, there need be no non-viral genetic sequences inserted into an adenoviral vector to accomplish adenoviral delivery of E1A. Of course, LT-encoding DNA, or other neu-suppressing gene product encoding sequences may be introduced via adenoviral vectors as well.

The expression vector comprises a genetically engineered form of adenovirus. Knowledge of the genetic organization or adenovirus, a 36 kB, linear, double-strained DNA virus, allows substitution of large pieces of adenoviral DNA with foreign sequences up to 7 kB (Grunhaus and Horwitz, 1992). In contrast to retrovirus, the infection of adenoviral DNA in host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is a particularly suitable gene transfer vector because of its midsized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, located at 16.8 m$\mu$ is particularly efficient during the late phase of infection, and all the mRNA's issued from this promoter possess a 5'-tripartite leader (TL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system in is an alternative approach for the production of recombinant adenovirus.

A preferred method of introducing the E1A gene to an animal is to introduce a replication-deficient adenovirus containing the E1A gene. An example of such an adenovirus is Ad.E1A(+). Since adenovirus is a common virus infecting humans in nature and the E1A gene is a gene that is present in native adenovirus, the use of a replication deficient E1A virus to introduce the gene may efficiently deliver and express E1A into target cells.

The replication-deficient E1A virus made by E1B and E3 deletion also avoids the viral reproduction inside the cell and transfer to other cells and infection of other people, which means the viral infection activity is shut down after it infects the target cell. The E1A gene is still expressed inside the cells. Also, unlike retrovirus, which can only infect proliferating cells, adenovirus is able to transfer the E1A gene into both proliferating and non-proliferating cells. Further, the extrachromosomal location of adenovirus in the infected cells decreases the chance of cellular oncogene activation within the treated animal.

While the wild-type adenovirus may be used directly to transfer the E1A gene into HER-2/neu expressing cancer cells, wild-type virus will produce large amounts of adenovirus in the human body and therefore might cause potential side effects due to the replication competent nature of the wild type adenovirus. It is therefore an advantage to use the replication-deficient adenovirus such as E1B and E3 deletion mutant Ad.E1A(+) to prevent such side effects. In fact, many modifications in the native adenovirus will result in a modified virus that will be useful for the purpose of the invention. Further modification of adenovirus such as E2A deletion may improve the E1A expression efficiency and reduce the side effects. The only requirement of a native or modified adenovirus is that it should express an E1A gene in order to have the utility of the invention.

Adenovirus can be used is by introducing an LT gene product into such a cell. The LT gene product can be an LT mutant, especially a nontransforming mutant such as K1. Such introduction can typically involve the introduction of an LT gene. In some preferred methods, the LT gene can be introduced by the use of an adenovirus that contains both the E1A gene and the LT gene. In this case, adenovirus is a preferably a replication-deficient adenovirus such as the Ad.E1A(+) adenovirus. However, the introduction of the LT gene can be by any manner described in this specification or known to those of skill in the art such as viral, plasmid, retroviral vectors or liposomes.

Introduction of the adenovirus containing the neu-suppressing gene product gene into a suitable host is typically done by injecting the virus contained in a buffer.

The nature of the adenovirus vector is not believed to be crucial to the successful practice of the invention. Of course, as discussed above, it is adventageous if the adenovirus vector is replication defective, or at least conditionally defective, The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, a particularly useful vector according to the present invention is replication defective and will not have an adenovirus E1 region. Thus, it will be convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration in to the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adendoviruses have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotatic inoculation into the brain (Le Gal La Salle et al., 1993).

(ii) Retroviruses

The retroviruses are a group of single-stranded RNA viruses characterized by an ability to convert their RNA to double-stranded DNA to infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, termed ψ components is constructed (Mann et al., 1983). When a recombinant plasmid containing a human cDNA, together with the retroviral LTR and ψ sequences is introduced into this cell line (by calcium phosphate precipitation for example), the ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact ψ sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

One limitation to the use of retrovirus vectors in vivo is the limited ability to produce retroviral vector titers greater than $10^6$ infections U/mL. Titers 10- to 1,000-fold higher are necessary for many in vivo applications.

Several properties of the retrovirus have limited its use in lung cancer treatment (Stratford-Perricaudet and Perricaudet, 1991; (i) Infection by retrovirus depends on host cell division. In human cancer, very few mitotic cells can be found in tumor lesions (Warner and Heston, 1991). (ii) The integration of retrovirus into the host genome may cause adverse effects on target cells, because malignant cells are high in genetic instability. (iii) Retrovirus infection is often limited by a certain host range. (iv) Retrovirus has been associated with many malignancies in both mammals and vertebrates. (v) The titer of retrovirus, in general, is 100- to 1,000-fold lower than that of adenovirus.

(iii) Other Viral Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpes viruses may be employed. They offer several attractive features for various mammalian cells (Friedmann, 1989; Ridgeway, 1988; Baichwal and Sugden, 1986; Coupar et al., 1988; Howrich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Cultures media containing high titers of the recombinant virus were used to infect primary duckling hepatocytes. Stable CAT gene expression was detected for at least 24 days after transfection (Change et al., 1991).

(iv) Liposomal Transfection

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

The present invention also provides particularly useful methods for introducing neu-suppressing gene products into cells. One method of in vivo gene transfer which can lead to expression of genes transfected into cells involves the use of liposomes. Liposomes can be used for both in vitro and in vivo transfection. Liposome-mediated gene transfer seems to have great potential for certain in vivo applications in animals (Nicolau et al., 1987). Studies have shown that intravenously injected liposomes are taken up essentially in the liver and the spleen, by the macrophages of the reticuloendothelial system. The specific cellular sites of uptake of injected liposomes appears to be mainly spleen macrophages and liver Kupffer cells. Intravenous injection of liposomes/DNA complexes can lead to the uptake of DNA by these cellular sites, and result in the expression of a gene product encoded in the DNA (Nicolau, 1983).

The inventors contemplate that neu-suppressing gene products can be introduced into cells using liposome-mediated gene transfer. It is proposed that such constructs can be coupled with liposomes and directly introduced via a catheter, as described by Nabel et al. (1990). By employing these methods, the neu-suppressing gene products can be expressed efficiently at a specific site in vivo, not just the liver and spleen cells which are accessible via intravenous injection. Therefore, this invention also encompasses compositions of DNA constructs encoding a neu-suppressing gene product formulated as a DNA/liposome complex and methods of using such constructs.

Liposomal transfection can be via liposomes composed of, for example, phosphatidylcholine (PC), phosphatidylserine (PS), cholesterol (Chol), N-[1-(2,3-dioleyloxy) propyl]-N,N-trimethylammonium chloride (DOTMA), dioleoylphosphatidylethanolamine (DOPE), and/or 3βN-(N'N'-dimethylaminoethane)carbarmoyl cholesterol (DC-Chol), as well as other lipids known to those of skill in the art. Those of skill in the art will recognize that there are a variety of liposomal transfection techniques which will be useful in the present invention. Among these techniques are those described in Nicolau et al., 1987, Nabel et al., 1990, and Gao et al., 1991. The inventors have had particular success with liposomes comprising DC-Chol. More particularly, the inventors have had success with liposomes comprising DC-Chol and DOPE which have been prepared following the teaching of Gao et al., 1991, in the manner described in the Preferred Embodiments Section. The inventors also anticipate utility for liposomes comprised of DOTMA, such as those which are available commercially under the trademark Lipofectin™, from Vical, Inc., in San Diego, Calif.

Liposomes may be introduced into contact with cells to be transfected by a variety of methods. In cell culture, the liposomes can simply be dispersed in the cell culture solution. For application in vivo, liposomes are typically injected. Intravenous injection allow liposome-mediated transfer of DNA complex to the liposomes to, for example, the liver and the spleen. In order to allow transfection of DNA into cells which are not accessible through intravenous injection, it is possible to directly inject the liposome-DNA complexes into a specific location in an animal's body. For example, Nabel et al. teach injection via a catheter into the arterial wall. In another example, the inventors have used intraperitoneal injection to allow for gene transfer into mice.

The present invention also contemplates compositions comprising a liposomal complex. This liposomal complex will comprise a lipid component and a DNA segment encoding a neu-suppressing gene. The neu-suppressing gene employed in the liposomal complex can be, for example, an LT gene or an E1A gene. Liposomal complexes comprising LT mutants may have certain advantages. These advantages may be particularly distinct when the LT gene encodes non-transforming LT mutant, such as K1. An E1A gene encoding either the E1A 12S or E1A 13S gene product, or both, may be complexed with a lipid to form the liposomal complex.

The lipid employed to make the liposomal complex can be any of the above-discussed lipids. In particular, DOTMA, DOPE, and/or DC-Chol may form all or part of the liposomal complex. The inventors have had particular success with complexes comprising DC-Chol. In a preferred embodiment, the lipid will comprise DC-Chol and DOPE. While any ratio of DC-Chol to DOPE is anticipated to have utility, it is anticipated that those comprising a ratio of DC-Chol: DOPE between 1:20 and 20:1 will be particularly advantageous. The inventors have found that liposomes prepared from a ratio of DC-Chol:DOPE of about 1:10 to about 1:5 have been useful.

The 12S E1A, 13S E1A, and LT gene products are capable of suppressing neu gene expression, it is proposed that one may employ any product, or two or more together, in the practice of the invention. Of course, in that the 12S and 13S products are derived from essentially the same gene sequences, and are merely the result of differential splicing, where the E1A gene itself is employed it will be most convenient to simply use the wild type E1A gene directly. However, it is contemplated that certain regions of either the E1A or the LT gene may be employed exclusively without employing the entire wild type E1A or LT gene respectively.

It is proposed that it will ultimately be preferable to employ the smallest region needed to suppress the neu gene so that one is not introducing unnecessary DNA into cells which receive either an E1A or LT gene construct. This may especially be true with regards to the rather large, 708 amino acid, LT protein. Techniques well known to those of skill in the art, such as the use of restriction enzymes, will allow for the generation of small regions of E1A and LT. The ability of these regions to inhibit new can easily be determined by the assays reported in the Examples.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

(v) Other Non-Viral Vectors

In order to effect expression of sense or antisense gene constructs, the expression construct must be delivered into a cell. This delivery may be accomplished in vitro, as in laboratory procedures for transforming cells lines, or in vivo or ex vivo (see below), as in the treatment of certain disease states. As described above, delivery may be via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct may simply consist of naked recombinant DNA or plasmids. Transfer of the construct may be performed by any of the methods mentioned above which physically or chemically permeabilize the cell membrane. This is particularly applicable for transfer permeabilize the cell membrane. This is particularly applicable for transfer in vitro but it may be applied to in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al, 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

The Examples which follow set forth studies wherein the inventors demonstrate the ability of the E1A gene to suppress neu gene expression (Example I), neu gene-mediated tumorigenicity (Example II), neu gene-mediated metastasis (Example III), to suppress c-erbB-2/neu expression in human ovarian carcinoma (Example IV), and gene therapy with E1A (Example VIII). Examples V and VI demonstrate suppression of neu with LT antigen. While these studies are believed to be exemplary of the invention, it will be appreciated by those of skill in the art that many modifications and alterations may be made in these embodiments without departing from the spirit and scope of the invention.

EXAMPLE I

Transcriptional Repression of the neu Protooncogene by Adenovirus 5 E1A Gene Products This Example relates to studies conducted by the inventors which demonstrate that the adenovirus E1A 12S and 13S products are effective in repressing the transcriptional activity of the neu promoter. In particular, it is demonstrated that the conserved region 2 (CR2) of the E1A proteins are required for repression. Moreover, these studies indicated that a cis-acting DNA element in the upstream region of the neu promoter is responsible for the trans inhibition of the promoter by the E1A gene products.

1. Materials and Methods
    a. Plasmids

The recombinants used in this study have been described. pE1A (Chang et al., 1989: Hearing et al., 1985) is a plasmid expressing only the E1A region gene; pE1A12S and pE1A13S (Hearing et al., 1985) express 12S E1A protein and 13S E1A protein, respectively; pE1A-d1343 (Hearing et al., 1985) contains a 2-base-pair (bp) frameshift deletion in the E1A coding sequences (adenovirus nucleotide sequence positions 621 and 622); pE1A-d1346 (Hearing et al., 1985) contains an in-frame deletion of nucleotides 859–907 (48 bp), resulting in the deletion of 16 amino acids inside the CR2 of the E1A proteins; pE1Apr contains only the E1A promoter (−499 to +113 relative to the E1A cap site); pE2A-CAT (Chung et al., 1989) is a reporter plasmid containing E2 early promoter fused with the chloramphenicol acetyltransferase (CAT) reporter gene; pRSV-CAT is a reporter plasmid containing the CAT gene under the control of the Rous sarcoma virus (RSV) long terminal repeat (LTR); pE1B, pE2, and pE3 are plasmids expressing E1B, E2, and E3 genes, respectively. pneuEcoR1-CAT contains the 2.2-kilobase (kb) rat neu promoter and upstream sequences linked to the CAT gene. The deletion mutant of the neu promoter used in this study are described in the legends to FIGS. 3 and 4A. pRSV-β-gal contains the RSV LTR linked to β-galactosidase gene used as an internal control for transfection efficiency.

b. Cell Cultures

Cell cultures were performed as described (Hung et al., 1989; Matin, et al., 1984). The Rat-1 and SK-BR-3 cells were grown in dulbecco's modified Eagle's medium (DMEM) supplemented with 10% calf serum and fetal calf serum, respectively.

c. DNA Transfection

All transfections were carried out with the calcium phosphate precipitation technique of Graham and Van der EB as modified by Anderson et al. (Hung et al., 1989; Anderson et al., 1979; Ausubel et al., 1987). In each transfection, $8 \times 10^5$ Rat-1 cells or $2 \times 10^6$ SK-BR-3 cells ($2 \times 10$ cm dishes) were seeded 24 hr before transfection. Total transfection DNA was kept constant (maximum, 30 μg) among different samples in the same experiment by adding approximate amounts of carrier DNA (pSP64).

d. CAT Assays

Cell extracts were prepared 40 hr after transfection. Portions of cell lysates were assayed for β-galactosidase activity from the cotransfected pRSV-β-gal plasmid. All CAT assays (Gorman et al., 1982) were normalized to the internal transfection efficiency control. The CAT assay monitors acetylation of [$^{14}$C]chloramphenicol in cell extracts; [$^{14}$C]-chloramphenicol and its products are separated by thin-layer chromatography (TLC) and visualized by autoradiography. Individual spots on TLC paper were cut, their radioactivities were assayed by liquid scintillation spectrometry, and the relative CAT activities were calculated accordingly. Each experiment has been reproducibly repeated at least three times and a representative of several studies is shown.

e. Immunoblot

SK-BR-3 cell lysates were made 40 hr after transfection and immunoblots were performed as described (Matin et al., 1984). The mAB-3 monoclonal antibody against the human neu gene product—p185 protein—was purchased from Oncogene Science.

Figure 1A:
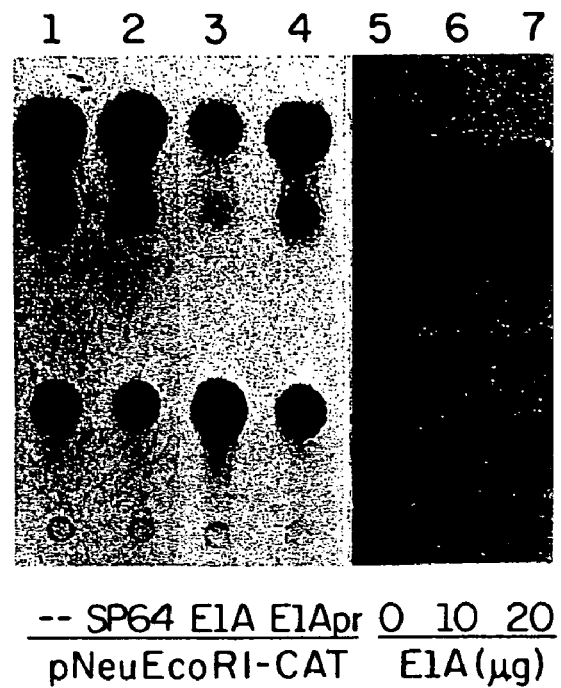
FIG. 1A and FIG. 1B show E1A gene product effects on the neu promoter.

2. Results
    a. Transcriptional Repression of neu by the Adenovirus 5(AD5) E1A Products A DNA segment of 2.2 kb containing the neu promoter and upstream sequences was fused with the CAT expression vector to generate the pneuEcoR1-CAT plasmid. In transient-expression assays using Rat-1 cells (FIG. 1A), a cotransfection of pneuEcoR1-CAT with pE1A, a plasmid expressing the E1A gene, led to a significant decrease of CAT activity. Cotransfection with pSP64, a plasmid vector, had no effect on CAT activity. To rule out the possibility that decreased transcription from neu promoters could be due to the titration of cellular transcription factors by the cotransfected E1A promoter, a deletion mutant, pE1Apr, which contains only the E1A promoter, was cotransfected with pneuEcoR1-CAT. No effect on CAT activity was observed. A reporter plasmid containing the CAT gene under the control of the RSV LTR was not E1A responsive, indicating that decreased CAT expression was not due to a general decrease of transcription by E1A.

Figure 1B:
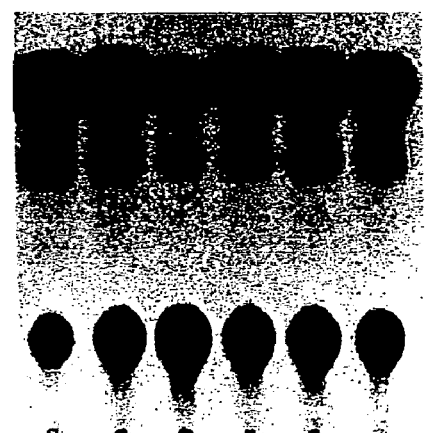

In parallel studies, stimulation of transcription from the E2A transcription unit by the E1A products was assayed by cotransfecting pE1A and pE2A-CAT (CAT gene driven by E2 early promoter). The results showed that repression of neu and transactivation of E2A promoter occur in the same range of pE1A concentration. To see if other adenovirus early genes can repress the neu promoter, plasmids expressing the early genes of adenovirus individually were cotransfected with pneuEcoR1-CAT (FIG. 1B). No change in CAT activity was observed with E1B, E2, or E3 alone, indicating the among these early genes of adenovirus, only the E1A gene could function as a repressor of the neu promoter.

b. Repression of neu Is E1A Concentration Dependent and Requires the E1A Conserved Region 2

Figure 2A:
FIG. 2A, FIG. 2B FIG. 2C FIG. 2D and FIG. 2E show transient expression from neu promoter with cotransfection with increasing amounts of pE1A (FIG. 2A), pE1A-13S (FIG. 2B), pE1A-12S (FIG. 2C), and pE1Ad1346 (FIG. 2D). A constant amount (5 $\mu$g) of the pneuEcoR1-CAT construct was cotransfected into Rat-1 cells with 5, 10, 15, and 20 $\mu$g of the test constructs. The total amount of the transfected DNA were kept constant by adding the appropriate amount of carrier DNA pSP64. The relative CAT activities without E1A (lanes 0 in FIG. 2A, FIGS. 2B, 2C and FIG. 2D) are defined as 100%. The relative CAT activities with 5, 10, 15 and 20 $\mu$g of test constructs are as follows: E1A, 68%, 35%, 26%, 17%; E1A-13S, 72%, 48%, 36%, 24%; E1A-12S, 66%, 46%, 28%, 21%; E1Ad1346, 102%, 103%, 99%, 102%, (FIG. 2E). Summary of the effects of different E1A mutants on transient expression from the neu promoter. Schematic structures of the proteins encoded by different E1A mutants are shown on the bar diagram. Hatched areas represent the conserved protein regions of the E1A products. Bar diagrams are not drawn to scale.

To further study the interactions of E1A genes products with the neu promoter, increasing amounts of pE1A were cotransfected with pneuEcoR1-CAT in ratios of 1:1, 2:1, 3:1, and 4:1 (FIG. 2A). Inhibition of the gene expression directed by the neu promoter was found to be dependent on pE1A concentration, and 50% repression could be observed at as low as a 1:1 ratio of pE1A:pneuEcoR1-CAT.

Figure 2B:
Figure 2C:
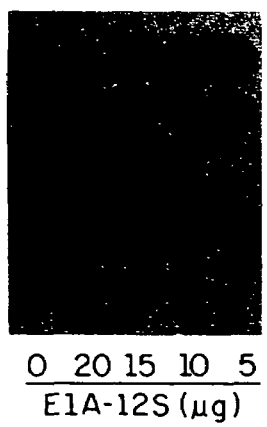

The Ad5 E1A gene produces two major spliced products, the 12S and 13S mRNAs, that encode proteins 243 and 289 amino acids long, respectively (Moran et al., 1987). To determine which E1A gene product was responsible for the observed repression, the same studies were performed with recombinant plasmids expressing either 12S or 13S E1A gene product (pE1A-12S and pE1A-13S). As shown in FIGS. 2B and C, both the 12S and 13S products were effective at repressing neu transcription in a concentration-dependent manner.

The E1A gene products contain three highly conserved regions; CR1, CR2, and CR3 (Moran et al., 1987; Van Dam et al., 1989). CR1 and CR2 exist in the 12S and 13S, whereas CR3 is unique to the 13S product. Since 12S itself can repress neu efficiently, the inventors reasoned that the CR3 is dispensable for transcriptional repression of neu by E1A.

Figure 2D:
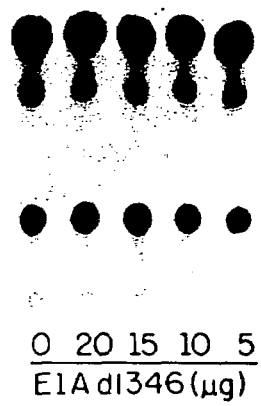
Figure 2E:
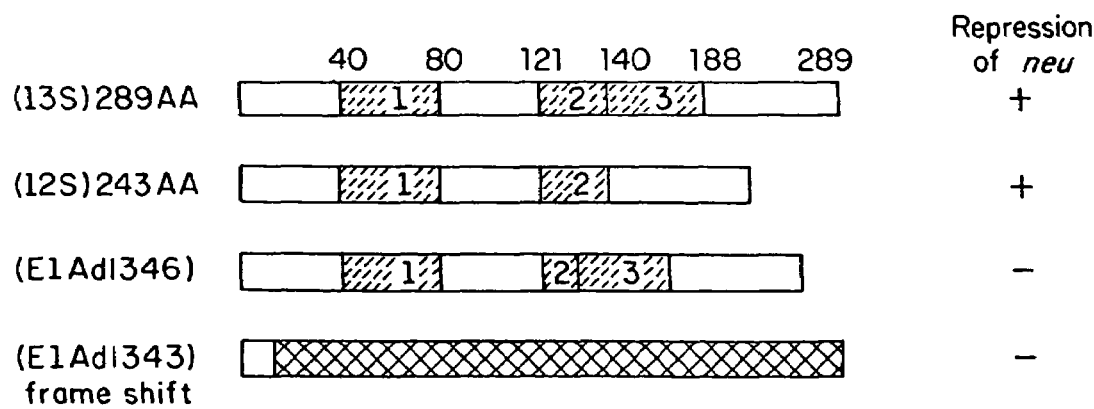

To further localize whether the CR1 or the CR2 in the E1A protein was required for efficient repression of neu, parallel studies were performed using deletion mutants pE1Ad1343 and pE1Ad1346 (Hearing et al., 1985). The pE1Ad1343 mutant contains a 2-bp deletion in the E1A coding sequence, resulting in a frame shift in all three conserved regions of the E1A products and leaving only the N-terminal 40 amino acids intact. No effect on CAT activity was observed when pE1Ad1343 mutant was cotransfected with pneuEcoR1-CAT. The pE1Ad1346 mutant containing an in-frame deletion, which removed 16 amino acids within the CR2 but reserved the CR1, failed to express neu transcription (FIG. 2D). The inventors concluded that the CR2 of E1A gene products is required for efficient transcriptional repression of neu (FIG. 2E).

c. Localization of Target DNA Element in the neu Promoter Responding to E1A Repression.

Figure 3A:
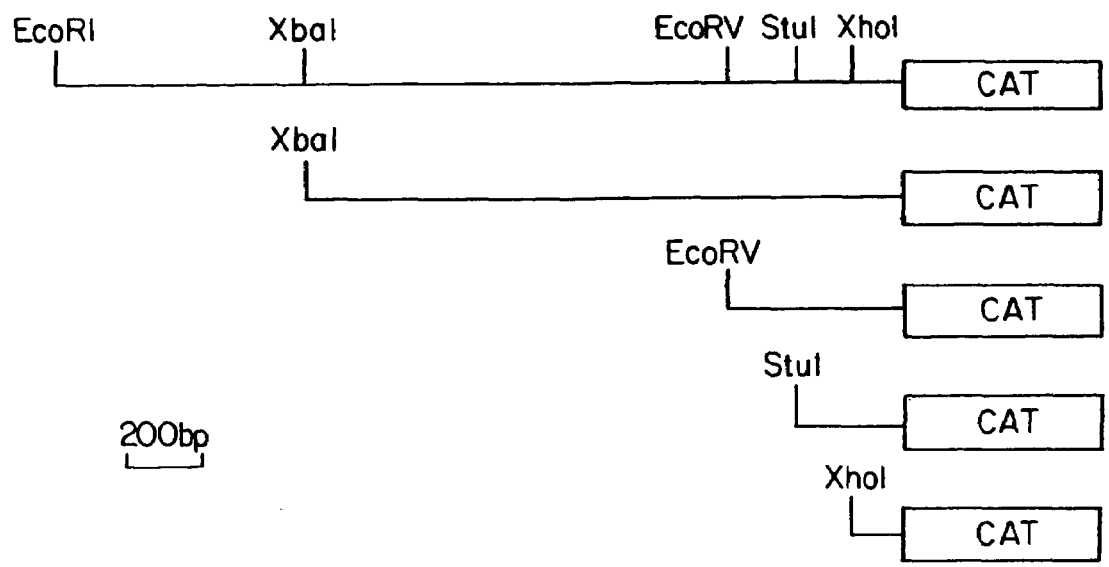
FIG. 3A and FIG. 3B show localization of E1A-responsive DNA element in the upstream region of neu promoter.
Figure 3B:
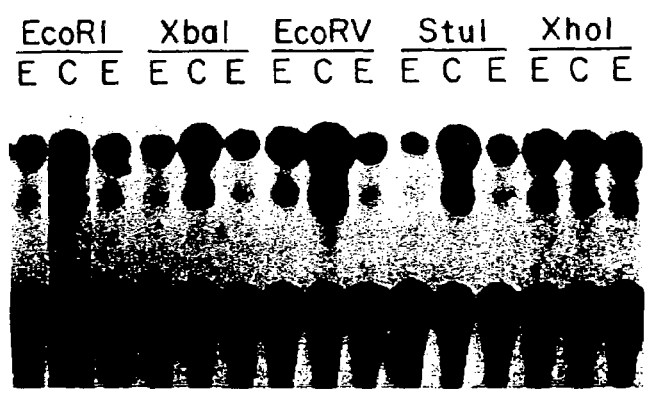

To localize the DNA element in the neu promoter that mediates the transcriptional repression by the E1A products, a series of 5' deletion constructs containing portions of the neu promoter linked to a functional CAT gene were cotransfected with pE1A into Rat-1 cells (FIG. 3A). The transient expression of the CAT gene driven by each of these promoter fragments after transfection with control plasmid vector pSP64 or with pE1A in a ratio of 1:2 is shown in FIG. 3B. Only the pneuXhoI-CAT containing the smallest promoter fragment was not repressed by E1A. Clearly the activity of a site within the Stu I-Xho I restriction fragment is sensitive to E1A repression. This Stu I-Xho I fragment is sensitive to E1A repression. This Stu I-Xho fragment is located between −198 and −59 with respect to the transcriptional start site of neu. The inventors concluded that the target DNA element responding to E1A repression resides inside this 139-bp Stu I-Xho I fragment.

d. Evidence for the Involvement of Trans-Acting Factor(s).

Figure 4A:
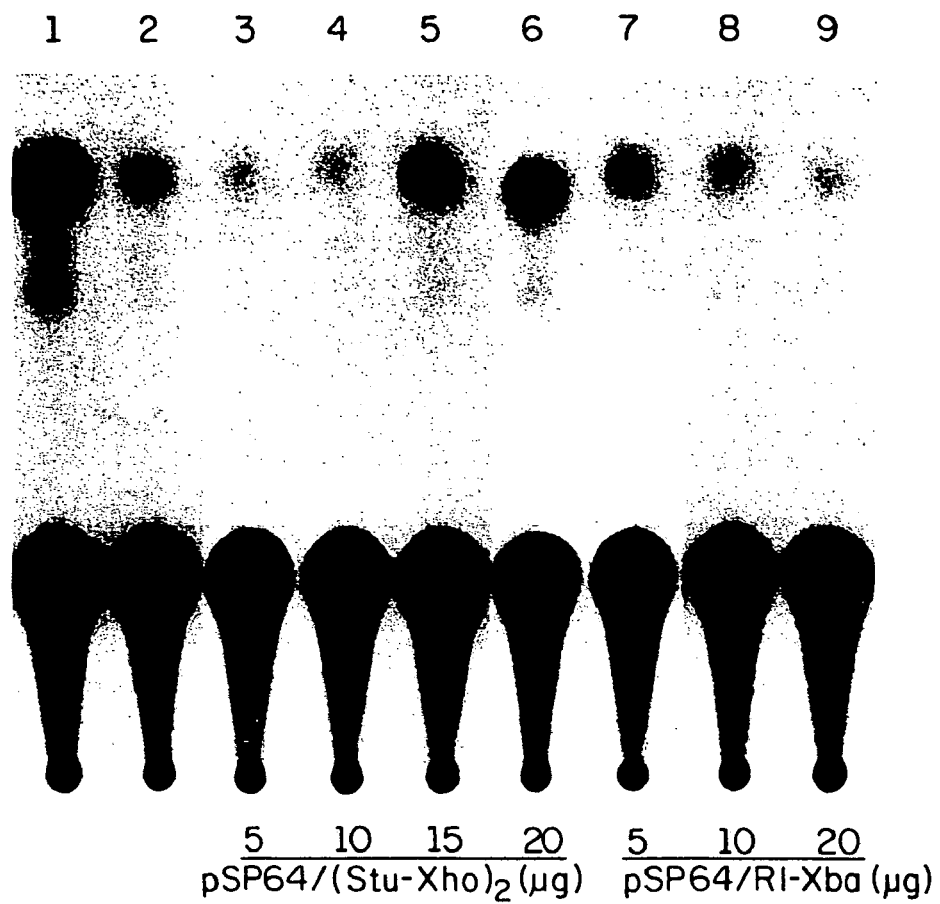
FIG. 4A and FIG. 4B show derepression of neu by cotransfection of competing amounts of Stu I-Xho I neu promoter fragments.

To examine whether this repression by the E1A products is a trans-acting process, the inventors attempted to remove the repression by cotransfecting a third recombinant, pSP64/Stu-Xho, containing only the Stu I-Xho I restriction fragment cloned in pSP64. Increasing amounts of pSP64/Stu-Xho, in cotransfections in which transcription of pneuEcoR1-CAT was repressed by pE1A, relieved the repression of neu transcription in a concentration-dependent manner (FIG. 4A). In contrast, no derepression was observed when pSP64/RI-Xba containing the EcoRI-XBA I restriction fragment cloned in pSP64 was cotransfected. The derepression was effective at a 4:1 ratio of pSP64/Stu-Xho: pneuEcoR1-CAT (FIG. 4A, lane 6), indicating that the Stu I-Xho I fragment can efficiently compete with the neu promoter for the transcription factor(s) involved in the repression of neu by E1A. These results confirm that the target for the E1A repression in the neu promoter is a cis DNA element within the Stu I-Xho I fragment of this promoter. Furthermore, this repression of transcription may involve an interaction between the DNA element and either the E1A products or some cellular transcription factors(s) interacting with or induced by the E1A products.

e. Repression of Human neu Expression in SK-BR-3 Cells.

Comparison of the Stu I-Xho I fragment of rat neu promoter sequence with its counterpart sequence in human neu promoter (Tal et al., 1982) reveals >86% homology. It was suspected by the inventors that the human neu gene might also be repressed by E1A at transcriptional level by way of similar mechanisms. If this is the case, cotransfection of the Stu I-Xho I fragment of rat neu promoter might be able to relieve the repression of human neu incurred by E1A.

Figure 4B:
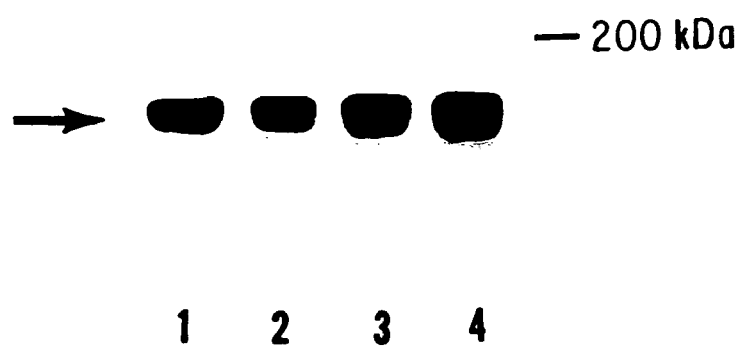

To test this possibility, cotransfection studies were carried out by using as recipient cells human breast cancer cell line Sk-Br-3, which is known to overexpress human neu mRNA and p185 proteins (Kraus et al., 1987). Immunoblotting studies with SK-BR-3 cell lysates showed that the expression of human neu gene products, the p185 protein, was reduced by introduction of E1A (FIG. 4B, compare lane 1 with lane 4). Cotransfection of pSP64/R1-Xba plasmids with pE1A at a 4:1 ratio was ineffective in removing the repression of p185 expression by E1A, whereas cotransfection of pSP64/Stu-Xho with pE1A at the same ratio relieved the repression by E1A It is known that the maximum efficiency of transient transfection can reach only 50% (Chen et al., 1988); the other 50% of nontransfected Sk-Br-3 cells should still produce high levels of p185 proteins, which can result in high background in the E1A-mediated repression of p185. Therefore, the repression effect on the endogenous neu-encoded p185 by transiently transfected E1A in the immunoblotting assay was not as dramatic as that observed in CAT assays. However, the small difference was detected reproducibly. The best interpretation of the results is that E1A can repress human neu promoter at transcriptional level by targeting at the cis-acting DNA element in human neu promoter corresponding to the Stu I-Xho I fragment of rat neu promoter.

f. The Sequence TGGAATG is an Important Site for the E1A-Mediated Repression.

E1A has been reported to repress enhancer mediated transcription activation of simian virus 40 (Borrell et al., 1984), polyomavirus (Velcich et al., 1986), immunoglobulin heavy chain (Hen et al., 1985), and insulin genes (Stein et al., 1987). Comparison of the enhancer sequences of these genes reveals a consensus sequence which is likely to be the core sequence of the E1A-responding element.

AAA (G)TGGTTT(G)

However, there has been no experimental evidence to support this notion. A sequence, TGGAATG, that matches the consensus sequence has been fund in the Stu 1-Xho 1 E1A-responding element of the rat neu promoter. An identical sequence also exists in the corresponding region of the human neu promoter (Tal et al., 1987). It is therefore conceivable that the sequence TGGAATG may be an important target sequence for the E1A-induced repression.

Figure 5:
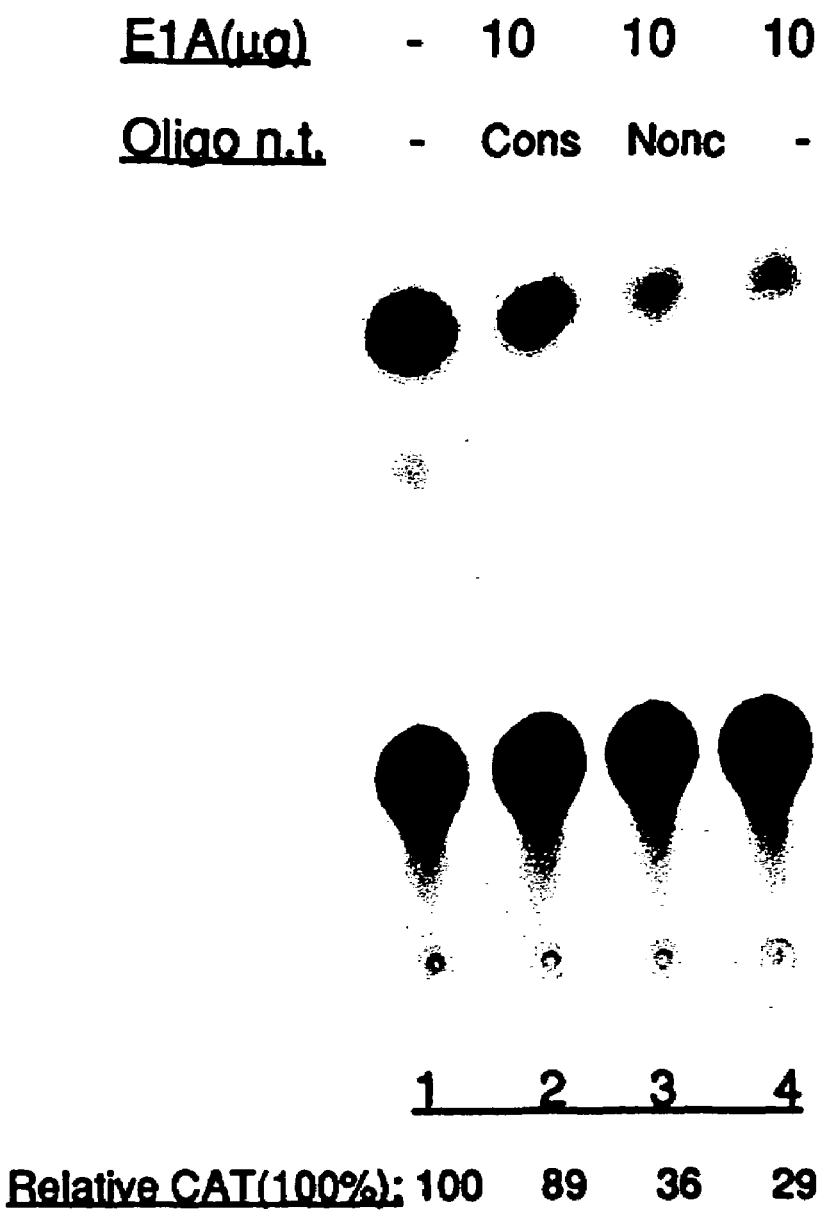
FIG. 5 shows removal of the E1A-mediated repression of neu by cotransfection of a 20-mer oligonucleotide containing the consensus sequence. Rat-1 cells were transfected with 3 µg of pneuEcoRV-CAT plasmids, giving basal neu promoter activity (lane 1); CAT activity after cotransfection with 10 µg of pE1A is shown in lane 4. Two micrograms of the 20-mer double-stranded oligonucleotide containing the consensus sequence (lane 2, Cons) was cotransfected with pneuEcoRV-CAT and pE1A (molar ratio of oligomer: pNeuEcoRV-CAT=35:1), resulting in significant derepression; cotransfection of 2 µg of a 22-mer random nonhomologous oligonucleotide with pneuEcoRV-CAT and pE1A had no significant derepression effect (lane 3, None). The values for relative CAT activity are the average of three studies. The upper strand sequence of the synthetic 20-mer oligonucleotide is shown at the bottom; the proposed E1A-responding sequence is underlined.

To investigate this possibility, a 20-mer oligonucleotide from the rat neu promoter containing the sequence TGGAATG was synthesized (FIG. 5). This oligonucleotide efficiently competed with the neu promoter for the transcriptional factors(s) involved in the repression of neu by E1A, resulting in a derepression effect (FIG. 5, lane 2), whereas a 22-mer random nonhomologous oligonucleotide had no derepression effect (FIG. 5, lane 3). These data provide experimental evidence that the 20-mer oligonucleotide harbors a critical sequence required for the E1A-induced inhibition. Since the sequence TGGAATG within this 20-mer oligonucleotide resembles the consensus sequence in the enhancer sequences of other genes that can be repressed by E1A, it is likely that this 7-bp sequence is the critical sequence that is mediating the E1A effect.

3. Discussion

The foregoing results show that in a cotransfection system, the E1A gene products repressed the neu expression at the transcriptional level. It is further demonstrated that the repressive effect on neu expression is lost in E1A products when part of the CR2 (amino acids 120–136) is deleted. Notably, a structure motif in this deleted part of the adenoviral E1A CR2 region is shared among the papovaviral large tumor antigens, the v- and c-myc oncoproteins, the E7 transforming proteins of human papilloma viruses, and the yeast mitotic regulator DCD25 gene product (Figge et al., 1988). This region encoding the shared motif is also required by E1A, simian virus 40 large tumor antigen, and human papilloma viruses 16 E7 for their specific binding to the human retinoblastoma gene product, RB protein (Whyte et al, 1988; Whyte et al., 1989).

These studies further elucidate the oligonucleotide sequence mediating E1A-induced repression in the upstream region of neu promoter. The sequence TGGAATG is perfectly conserved between rat and human neu promoter, which is indicative of functional importance. In addition, this sequence matches the consensus sequence of other genes that can also be repressed by E1A at transcriptional level. Taken together, these findings suggest that there may be common mechanisms involved in this type of E1A-mediated repression. It has been proposed that E1A may form a complex with cellular transcription factor(s) and thereby modulate the specific binding of the transcription factor(s) to enhancer elements that are important for transcription (Mitchell et al., 1989). Identification of the defined DNA sequences responsible for the E1A-mediated inhibition of neu transcription will allow us to identify the transcription factor(s) involved in this process.

The neu protooncogene is notably amplified in patients with metastatic breast cancer. Expression of the E1A gene can inhibit experimental metastasis of ras oncogene-transformed rat embryo cells. Here, it is shown that neu transcription can be repressed by E1A products in an established rat embryo fibroblast cell line, Rat-1. Furthermore, the inventors have found that in SK-BR-3 human breast cancer cells expression of the p185 protein, the human neu gene product, was reduced by introduction of E1A gene. The derepression effect observed in the cotransfection experiment with the Stu 1-Xho 1 fragment has demonstrated that this reduction of p185 proteins is likely due to the similar transcriptional repression mechanisms.

EXAMPLE II

Adenovirus-5 E1A Gene Products Act as a Transformation Suppressor of Neu Oncogene In Example I, transcription of the neu protooncogene was shown to be strongly repressed by adenovirus-5 E1A gene products through the use of a transient transfection assay. In the present Example, the E1A gene has been stably introduced into the neu-transformed B104-1-1 cells, to demonstrate that E1A-mediated neu repression can suppress neu-mediated transforming activity. In these studies, cells that expressed E1A products possessed reduced transforming and tumorigenic activity, as evidenced using standard assays for each. These results demonstrated that E1A gene products can act negatively to suppress the transforming phenotype of the neu oncogene, and is believed to be the first example of a gene, i.e., the E1A gene, that can act in one setting as a transforming oncogene, and in another as a transforming suppressor gene.

The B104-1-1 cell line, an NIH3T3 transfectant that has approximately 10–20 copies of mutation-activated genomic neu oncogene has been shown to be highly transforming and tumorigenic (Bargmann et al., 1986; Stern et al., 1986). For the present studies, B104-1-1 cells and control NIH3T3 cells were transfected with either E1A plasmids expressing adenovirus-5 E1A gene, (pE1A), or a derivative plasmid containing only the E1A promoter without the E1A coding sequence (pE1Apr). Cells were cotransfected with pSV2neo plasmids carrying a neomycin resistant marker gene (Southern et al., 1982).

The transfections were carried out with the modified calcium phosphate precipitation procedure of Chen and Okayama (1988). In each transfection, $5 \times 10^5$ B104-1-1 cells or NIH3T3 cells ($2 \times 10$ cm dishes) were seeded 24 h before transfection. The cells were transfected with either 10 μg of the E1A expressing pE1A plasmid DNA or its derivative pE1Apr plasmid DNA, along with 1 μg of pSV2-neo plasmid DNA (Southern et al., 1982). Approximately 14 h post-transfection, cells were washed and cultured in fresh medium for 24 h and split at a 1:10 ratio. The cells were then grown in selection medium containing 500 µg/ml of G418 for 2–3 weeks and individual G418 resistant colonies were cloned using cloning rings and expanded to mass culture.

Three kinds of stable transfectants were thus established: (1) B-E1A transfectants: B104-1-1 transfectants harboring the E1A gene; (2) B-E1Apr transfectants: B104-1-1 transfectants containing E1A promoter sequence, which is used as a control cell line in this study; and (3) N-E1A transfectants: NIH3T3 cells transfected with the E1A gene.

Cells cultures were performed as described previously (Hung et al., 1989; Matin et al., 1989). The B104-1-1 cell line and NIH3T3 cell line were grown in Dulbecco's modified Eagle's medium (DMEM) supplemented with 10% calf serum in a humidified atmosphere at 5% $CO_2$ at 37° C. The B-E1A transfectants and N-E1A transfectants were grown under the same condition with addition of G418 (500 µg/ml) into the culture media.

FIG. 6 shows the molecular characterization of the representative stable transfectants used in this study, employing both Southern blot and immunoblot analyses. Southern blot analyses were performed essentially by published techniques as previously described (Zhang et al., 1989). Genomic DNAs extracted from cultured cells were digested overnight at 37° C. with a 2-fold excess of a restriction endonuclease (either EcoR1, Sst1, or BamH1). Ten µg of each sample were then resolved by electrophoresis on a 1% agarose gel and transferred to Nytran membrane (Schleicher & Schuell, Keen, NH) using a 10×SSC (1.5 m NaCl, 0.15 M sodium citrate). The blotted DNA were hybridized under high stringent conditions (68° C.) with [$^{32}$P] radioactive probe (1–5×10$^8$ CPM µg$^{-1}$) labeled by using Random Primed DNA Labeling Kit (Boehringer Mannheim Biochemicals, Indianapolis, Ind.). The blots were washed twice for 15 min each in 2×SSC, 0.1% SDS at room temperature, and then twice for 30 min each in 0.1×SSC, 0.1% SDS at 68° C. with constant agitation. The filters were dried at room temperature and then exposed to Kodak X-OMAT™ AR film at −80° C. for 1 to 3 days.

Immunoblot analysis were performed basically by published techniques (Towbin et al., 1979) as previously described (Matin et al., 1990). Confluent cells growing in 10 cm plates were lysed with RIPA-B buffer (20 mM sodium phosphate, pH 7.4, 150 mM NaCl, 5 mM EDTA, 1% Triton, 10 µg/ml Aprotinin, 2 mM PMSF, 10 µg/ml Leupeptin and 4 mM iodoacetic acid) and then centrifuged at 10×g for 20 min at 4° C. The protein concentration of the supernatants was determined by Bio-Rad protein assay (Bio-Rad Laboratories, Richmond, Calif.). 50 µg of each sample were subjected to SDS polyacrylamide gel electrophoresis (10%) and transferred to nitrocellulose. The nitrocellulose filters were treated with 3% nonfat dry milk in TPBS buffer (0.05% Tween-20, 138 mM NaCl, 2.7 mM KCl, 4.3 mM Na2HPO4.7$H_2O$ and 1.4 mM $KH_2PO_4$) for 1 h at room temperature, followed by an overnight incubation at 4° C. with primary monoclonal antibodies M73 against the E1A proteins or mAb-3 against the neu encoded p185 protein (purchased from Oncogene Science Inc., Manhasset, N.Y.). After three 10 min washes with TPBS buffer, the nitrocellulose was then incubated for 1 h at room temperature with 1:1000 dilution of horseradish peroxidase-conjugated goat anti-mouse immunoglobulin (Bio-Rad Laboratories). The nitrocellulose filters were washed 3 times in TPBS buffer and were subjected to color developing reaction with horseradish peroxidase substrate (Kirkegaard & Perry Laboratories, Inc., Gaithersburg, Md.).

Figure 6A:
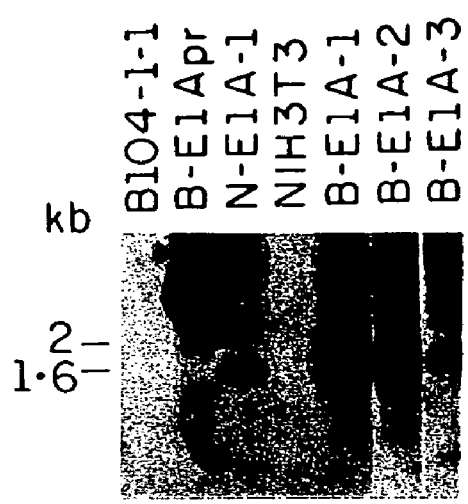
FIG. 6A, FIG. 6B, FIG. 6C and FIG. 6D show E1A gene presence and protein production in cells.
Figure 6B:
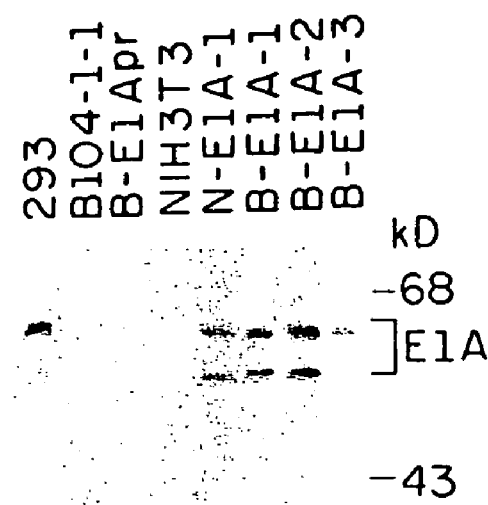

To assure that the exogenous E1A gene or E1A promoter DNA had integrated into the genome of the transfectants, DNA blot analysis with the E1A probe was performed and the results confirmed the integration of transfected foreign DNA (FIG. 6A). Noticeably, the three B-E1A transfectants studied (B-E1A-1, B-E1A-2 and B-E1A-3) acquired different copy numbers of the E1A gene. Immunoblot detection of E1A further confirmed that the B-E1A and N-E1A transfectants actually produced E1A proteins and the E1A protein levels in these transfectants are lower than that in the 293 cell line, an established cell line of primary human embryonal kidney transformed by adenovirus DNA. (FIG. 6B).

Figure 6C:
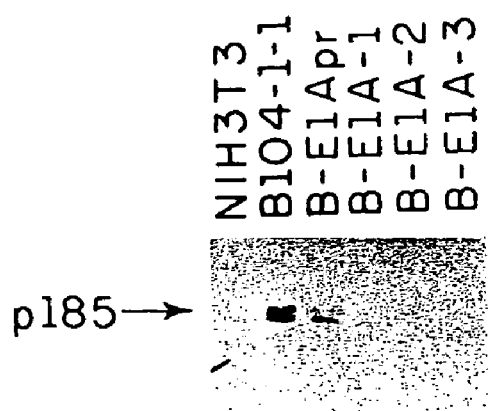
Figure 6D:
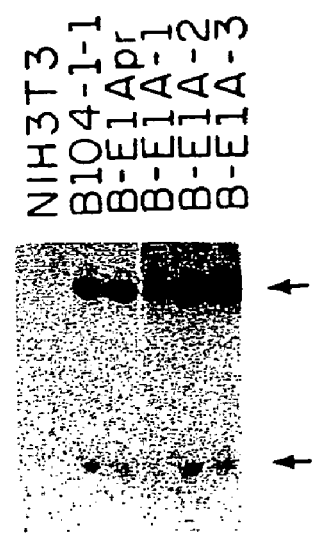
Figure 7A:
FIG. 7A, FIG. 7B, FIG. 7C, FIG. 7D, FIG. 7E, FIG. 7F show morphologic effects of E1A expression in neu-transformed B104-1-1 cells.
Figure 7D:
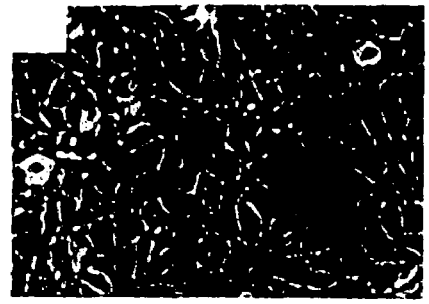
Figure 7B:
Figure 7E:
Figure 7C:
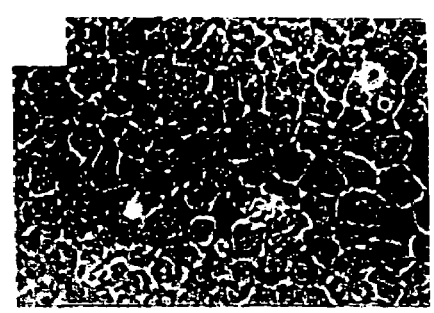
Figure 7F:

To examine if expression of E1A can inhibit neu expression, immunoblot analysis for the neu-encoded p185 protein was also performed and the p185 proteins were virtually undetectable in all the transfectants using horse radish peroxidase detection method (FIG. 6C). However, slightly higher levels of p185 proteins could be detected in B-E1A-3 than those in B-E1A-1 and B-E1A-2 when the more sensitive $^{125}$I-protein-A detection method was used. Since p185 proteins were barely detectable in B-E1A transfectants, DNA blot analysis for rat neu gene was conducted to make sure that the neu gene was not lost. As shown in FIG. 6D, the incorporation of E1A gene into the genome did not alter the neu gene at the DNA level.

Among the three B-E1A transfectants, B-E1A-2 and B-E1A-3 had levels of the neu gene that were comparable to those of the parental B104-1-1 cell line; while B-E1A-1 appeared to have a lower level neu gene. This may be due to partial loss of the neu gene in this line during the establishment of this transfected cell line. The three B-E1A transfectants shown in FIG. 6 were chosen for further transformation assay because they represented three different subtypes of B-E1A transfectants: (1) B-E1A1 had fewer copies of neu gene compared to B104-1-1 and more copies of E1A gene; (2) B-E1A-2 retained the same level of neu as B 104-1-1 and high levels of E1A gene; (3) B-E1A-3 contained the same amount of neu as B104-1-1, but a low quantity of the E1A gene.

The transforming phenotype of the neu-transformed cells usually includes a transformed morphology, non-contact-inhibited growth pattern, increased DNA synthesis rate, anchorage-independent growth and the ability to induce tumors in nu/nu mice. To determine the effect of E1A expression on the transforming ability of neu-transformed B104-1-1 cells, the B-E1A transfectants as well as the control cell lines were assayed for all the above mentioned transforming parameters using standard protocols.

The results of these studies demonstrated that the highly transformed morphology of B104-1-1 cells was essentially unchanged after pE1Apr transfection but was markedly altered by pE1A transfection (FIG. 7). The B-E1A transfectants exhibit non-transformed flattened morphology and a contact-inhibited growth pattern (FIG. 7). Expression of E1A proteins in NIH3T3 cells did not significantly alter the monolayered morphology. The results indicated that E1A gene products could specifically reverse the transforming morphology of the neu-transformed cells.

DNA synthesis was also studied as a measure of cell growth, to determine whether the B-E1A transfectants were actively synthesizing DNA as compared to controls. These studies were conducted through the use of a [$^3$H]-thymidine incorporation assay. For these studies, cells were plated in ten replica into 96 well plates at a density of 9×10$^3$ cells/well and cultured in DMEM supplemented with 10% calf serum. [$^3$H]-thymidine (1 µCi) was added to each well at time points of 16, 40 and 64 h and continuously incubated at 37° C. for 2 h. Cells were then harvested and cellular DNA were bound to glass fiber filters. Radioactivities of individual samples were counted by Scintillation counter. Average cpm were calculated from ten replicate samples.

Figure 8A:
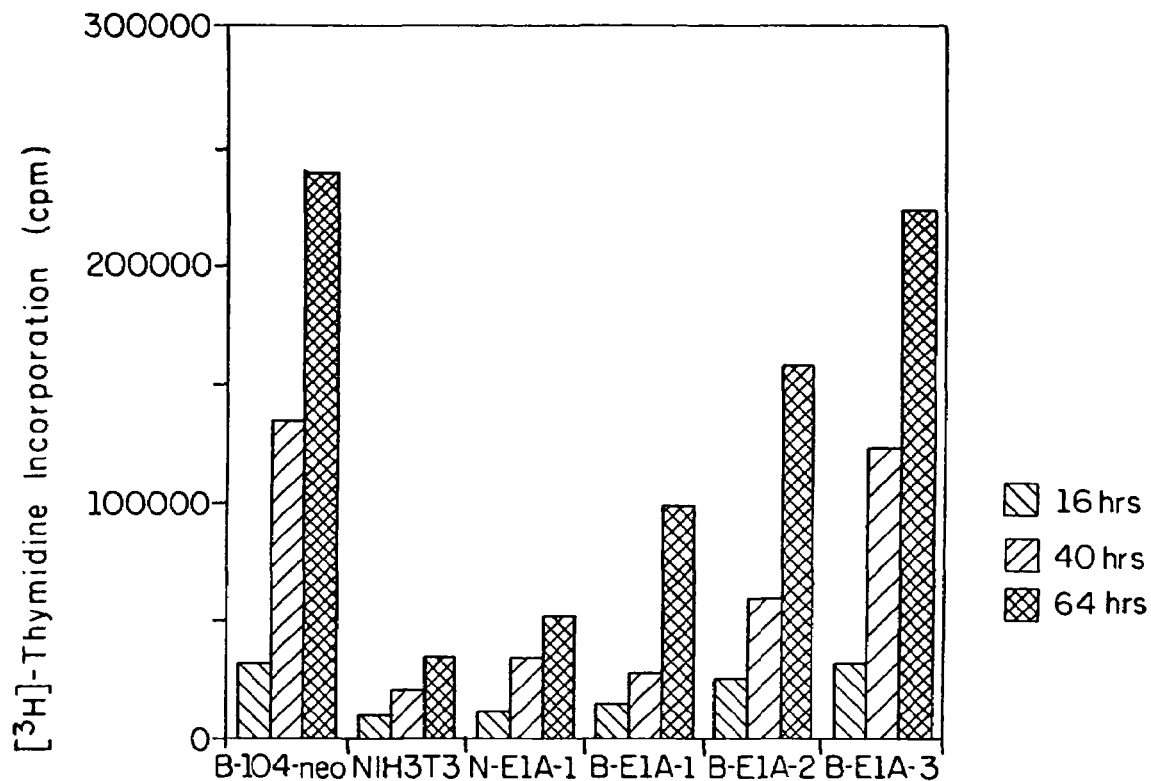
FIG. 8A and FIG. 8B show E1A effects on DNA synthesis.

The rate of DNA synthesis, as indicated by [$^3$H]-thymidine incorporation, was different among the three B-E1A transfectants (FIG. 8A). B-E1A-1 and B-E1A-2 displayed a much lower DNA synthesis rate, which coincided with their slower cell growth rate compared to B104-1-1 cells. This E1A-induced decrease in [$^3$H]-thymidine incorporation was not as dramatic in the B-E1A-3 cell line possibly due to the lower level of the E1A proteins. These data suggested that E1A proteins can inhibit the effect of the neu oncogene on DNA synthesis and cell growth.

To test the influence of the E1A proteins on anchorage-independent growth, B104-1-1 cells and the B-E1A transfectants were assayed for their ability to grow in soft agar. The ability of B104-1- cells, B-E1A transfectants, NIH3T3 cells and N-E1A transfectant to grow in soft agarose was determined as described previously (Matin et al., 1990). Cells (1×10$^3$ cells/plate) were plated in a 24 well plate in DMEM containing 10% calf serum and 0.35% agarose (BRL, Gaithersburg, Md.) over a 0.7% agarose lower layer. The cells were incubated at 37° C. for 3 weeks and the plates were stained with p-iodonitrotetrazolium violet (1 mg/ml) for 24 h at 37° C. and colonies were counted.

Figure 8B:
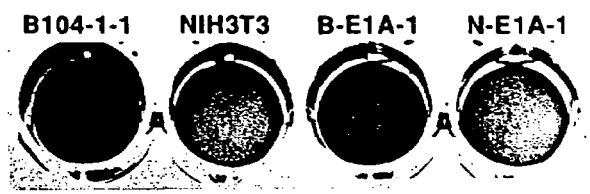

The results of the soft agar studies demonstrated that colony formation by the E1A transfectants were strikingly reduced compared to that of B104-1-1 and B-E1A pr transfectants (FIG. 8B). It is noteworthy that the colony formation by NIH3T3 and N-E1A-1 lines did not vary significantly.

The most stringent experimental test for neoplastic behavior is the ability of injected cells to form tumors in nude mice. Studies in nude mice were conducted because the examination of E1A repression of neu-mediated tumorigenicity in vivo was considered to be a critical test of E1A effectiveness. For conducting tumorigenicity studies, the B104-1-1 cells, B-E1A transfectants, NIH3T3 cells and N-E1A transfectant in log-phase growth were trypsinized and washed twice with phosphate buffered saline and centrifuged at 250×g. The viable cells were then counted, and 1×10$^5$ cells in 0.1 ml of phosphate buffered saline were injected subcutaneously into both the right and left flanks of 5 to 6-week old female homozygous nu/nu (nude) mice (Harlan Sprague Dawley Co.) under sterile conditions. Tumor formation was scored at indicated days as presence or absence of a visible tumor mass. Sixteen days after injection, tumor volumes were estimated as the product of three-dimensional caliper measurements (longest surface length and width and tumor thickness). The growth of tumors was monitored for a minimum of 16 days and maximum of 2 months.

Figures 9A, 9B:
FIG. 9A and FIG. 9B show the effects of a tumorigenicity study.

When cells of the parental B104-1-1 line were injected subcutaneously in nude mice, solid tumors developed by 8 days after injection; however, the same quantity of the E1A transfectants did not form tumors in nude mice until 12–26 days after injection and in every case the tumors were much smaller than those from B104-1-1 cells (FIG. 9A).

Although the B-E1A-1 and B-E1A-2 transfectants contained comparable amounts of the E1A gene, the B-E1A-1 cells did not cause tumor development until a much later time. This is probably due to the lower level of neu gene in this line. On the other hand, although both of the B-E1A-2 and B-E1A-3 transfectants contained the same level of the neu gene as B 104-1-1, the transforming suppression effect on BE1A-3 was not as strong as on B-E1A-2. This was likely due to the lower level of the E1A gene in B-E1A-3. Typical results of E1A expression on neu oncogene induced tumorigenicity are shown in the photographs in FIGS. 9B and 11A. Evaluated 18 days after injection, animals injected with B104-1-1 cells were found to bear huge tumors, whereas those injected with B-E1A-2 transfected cells had considerably smaller tumor nodules. As expected, control animals injected with NIH3T3 cells showed no evidence of tumor formation.

Previous studies of Wilms' tumor cells and human prostate carcinoma DU145 cells demonstrated that reintroduction of chromosome 11 to Wilm's tumor cells or restoration of RB gene to DU145 cells suppressed tumor formation but did not alter the cell morphology, growth rate or colony-forming ability (Weissman et al., 1987; Bookstine et al., 1990). These data suggest that growth rate in culture and tumorigenicity in nude mice are separable phenomena. In the present study, the B-E1A-1 and B-E1A-2 cells exhibited slower growth rate and much weaker tumorigenic activity. However, suppression of tumorigenicity cannot entirely be explained by their slower growth rate and decreased [$^3$H]-thymidine incorporation. For example, the B-E1A-3 cells possessed similar [$^3$H]-thymidine incorporation and cell growth rate as B104-1-1 cells, while their tumorigenic activity was markedly suppressed as well. Taken together, these results clearly demonstrate that introduction of the E1A gene into B104-1-1 cells suppresses all the transforming properties of the neu-transformed cells.

EXAMPLE III

Suppression of Neu-Mediated Metastasis by E1A Gene Products

Additional studies were conducted using B-E1A transfectants of B104-1-1 to demonstrate that E1A products also suppress neu-mediated metastasis. These studies employed B-E1A transfectants (B-E1A-1 through B-E1A-5) as well as the negative and positive controls, NIH/3T3 and B104-1-1, respectively, in a cell motility, in vitro invasion and an experimental metastasis assay.

The metastasis studies were performed essentially as described by Wexler, 1966. Briefly, six-week-old pathogen-free female nude mice (Harland) were quarantined for 1 week and then used in the studies. Seven to ten mice/experimental group were inoculated with 1×10$^5$ cells/0.1 ml in PBS via the lateral tail vein at day 0. Each cell line was then assessed at two different passage numbers. Mice were sacrificed at 21 days following injection and the number of lung metastases were determined by infiltration with India ink. Only those lung nodules >1 mm in diameter were counted. On further examination, no extrapulmonary metastases were found. Representative photographs illustrating the gross appearance of the lungs from these animals are shown in FIG. 11B, whilst the quantitative data from these studies are detailed below in Table 2.

TABLE 2

| | EXPERIMENTAL METASTASIS ASSAY | | |
| | Experimental metastasis | | |
| Cell Line | Transfected gene | Frequency | No. of lung nodules (mean + SE) |
|---|---|---|---|
| 2NIH/3T3 | — | 0/9 | 0.0 ± 0.0 |
| B104-1-1 | neu | 9/9 | 10.9 ± 10.3 |

TABLE 2-continued

EXPERIMENTAL METASTASIS ASSAY
Experimental metastasis

| Cell Line | Transfected gene | Frequency | No. of lung nodules (mean + SE) |
|---|---|---|---|
| N-E1A | E1A | 0/8 | 0.0 ± 0.0 |
| B-neo | neu + E1A | 7/7 | 9.5 ± 7.9 |
| B-E1A-1 | neu + E1A | 0/8 | 0.0 ± 0.0 |
| B-E1A-2 | neu + E1A | 3/9 | 0.8 ± 0.4 |
| B-E1A-3 | neu + E1A | 0/8 | 0.0 ± 0.0 |
| B-E1A-4 | neu + E1A | 1/7 | 0.1 ± 0.4 |
| B-E1A-5 | neu + E1A | 1/10 | 0.1 ± 0.4 |

The effectiveness of E1A at inhibiting neu-mediated metastasis is clearly illustrated in FIG. 11B. Furthermore, this single result was found to be representative of the entire study. None of the negative control mice, NIH/3T3 and E1A transfected NIH/3T3 (N-E1A), exhibited metastatic lung nodules. However, all of the positive controls (B104-1-1 and B-neo), exhibited metastatic nodules, at a mean frequency of about 10 nodules. In contrast, all of the experimental lines (B-E1A-1 through B-E1A-5) exhibited a reduced metastatic potential, with a frequency ranging from one to three (out of ten and nine, respectively.), and a mean number of 0.1 to 0.8 nodules in those animals that were positive. Note that two of the experimental lines, B-E1A-1 and B-E1A-3, were totally free of metastases.

An increase in cell motility has been shown to correlate with a higher metastatic potential. Therefore, a motility assay, which measures the migration of the tested cell to a chemo-attractant, fibronectin or hepatic sinusoidal endothelial cell conditioned media, was performed. As shown in FIG. 10A, all of the B-E1A transfectants showed decreased migration rate to different chemoattractants than that of B-neo cell line, which are B104-1-1 cells transfected with neomycin-resistant (neo) gene alone. he N-E1A cells also had a low migration rate which is comparable to that of NIH3T3 cells.

Another step in the metastatic process involves invasion of tissues and basement membranes. In vitro invasion assays also revealed significant differences between the B-neo cells and the B-E1A cell lines. B-neo cells demonstrated a high rate of invasion similar to that of B104-1-1 cells, while the B-E1A transfectants failed to invade the Matrigel. Injection of the B-neo cells and the five B-E1A cell lines into the tail vein of the nude mice showed dramatic differences in the frequencies and number of lung nodules (FIG. 10B and Table 2). Two of the five B-E1A transfectants did not give rise to any experimental metastatic tumors and the other three B-E1A lines had a very low incidence of experimental metastasis compared to that of B-neo cells (p>0.01). As expected, N-E1A cells were unable to produce any metastatic lung nodule. From these results, it is evident that E1A gene products can reduce the metastatic potential of neu-transformed 3T3 cells, possible by transcriptional repression of neu gene expression.

These results, typified by those shown in FIG. 11B, demonstrate that E1A gene products are able to suppress not only the tumorigenic and transformation events mediated by the neu gene (Example II), but are further able to suppress metastatic events that are neu mediated.

EXAMPLE IV

E1A Suppresses c-erbB-2/neu Expression Connected with Severe Malignancies in Human Ovarian Carcinoma The present example is directed to studies concerning the action of E1A in repressing c-erbB-2/neu overexpression in SKOV3.ip1 cells and the functions of E1A as a tumor suppressor gene in c-erbB-2/neu-overexpressing human cancer cells.

1. Inhibited Expression of c-erbB-2/neu-encoded p185 in E1A-Expressing Ovarian Carcinoma Transfectants The E1A-expressing plasmid was cotransfected into SKOV3.ip1 cells together with the pSV2-neo plasmid carrying the neomycin-resistance marker gene, thus generating the E1A-expressing ovarian carcinoma stable transfectants. The G418-resistant clones were selected and expanded into cell lines, which were designated ip1.E1A cell lines. The same approach was used to select control cell lines, in which the pE1Ad1343 plasmids containing a 2-base pair frameshift deletion in the E1A coding sequence and producing non-functional protein products were introduced into the SKOV3.ip1 cells to generate the ip1.Efs cell line.

It was possible that some of the stable transfectants selected by this cotransfection strategy only harbored the neomycin resistance gene but not the E1A gene. Therefore, to identify those ip1.E1A transfectants that integrated the E1A gene and actually produced E1A proteins, immunoblot analysis with anti-E1A antibodies was performed (FIG. 12A). Two of the ip1.E1A transfectants expressed multiple species of E1A proteins as described by Harlow et al., (1985), whereas the control ip1.Efs cell line, as expected, did not express E1A proteins.

In this manner, the inventors thus established two kinds of stable transfectants: (a) ip1.E1A cells (i.e., SKOV3.ip1 E1A-expressing transfectants), which were used to test the tumor-suppressing function of E1A; and (b) ip1.Efs cells (i.e., SKOV3.ip1 transfectants containing E1A frameshift mutants), which were used as a control cell line to make sure that the changes in transformation phenotypes (if any) in ip1.E1A transfectants were not due to the selection process or to transfection of the plasmids and the pSV2-neo gene.

As shown herein, E1A proteins can repress c-erbB-2/neu-encoded p185 expression in the c-erbB-2/neu oncogene-transformed N1H3T3 cells. In addition, it is also shown herein that E1A proteins can decrease the c-erbB-2/neu mRNA level as well as c-erbB-2/neu-encoded p185 in c-erbB-2/neu-overexpressing breast cancer cell lines. To determine if the expression of E1A in ip1.E1A transfectants can inhibit p185 expression, immunoblot analysis of c-erbB-2/neu-encoded p185 protein was performed.

It was found that p185 protein levels were dramatically decreased in both the ip1.E1A1 and ip1.E1A2 cell lines versus the control ip1.Efs cell line (FIG. 12B), which expressed an amount of c-erbB-2/neu-encoded p185 protein comparable to that of the parental SKOV3.ip1 cell line. Since p185 proteins were dramatically reduced in ip1.E1A transfectants, DNA blot analysis of the c-erbB-2/neu gene was conducted to ensure that the reduction in c-erbB-2/neu-encoded p185 protein level was not due to loss of the c-erbB-2/neu gene. As shown in FIG. 12C, both the ip1.E1A1 and ip1.E1A2 cell lines contained copy numbers of the c-erbB-2/neu gene similar to that of ip1.Efs cell line. Therefore, the incorporation of the E1A gene into the genome of SKOV3.ip1 cells did not alter the c-erbB-2/neu gene at the DNA level. Furthermore, these results indicate that the E1A can repress the c-erbB-2/neu-encoded p185 protein expression in ip1.E1A transfectants.

2. In Vitro Suppression of SKOV3.ip1 Cell Transformation by E1A Expression

Once the E1A-expressing ip1.E1A lines were established, the inventors examined the effect of E1A expression on the c-erbB-2/neu-overexpressing ovarian cancer cells in vitro, assessing growth properties, DNA synthesis rate, and colony formation in soft agar. The growth curves of the E1A-expressing ip1.E1A1 and ip1.E1A2 cell lines and control ip1.Efs cell line indicated that E1A expression slightly reduced the growth rate of these ovarian cancer cells versus the control cells (FIG. 13A). Measurement of the DNA synthesis rate by [$^3$H]thymidine incorporation assays revealed that the control ip1.Efs cells had a high level of [$^3$H]thymidine incorporation that was similar to that of SKOV3.ip1 cells and significantly higher than the [$^3$H]thymidine incorporation in the E1A-expressing ip1.E1A1 and ip1.E1A2 cell lines (FIG. 13B).

FIG. 13C shows that the c-erbB-2/neu-overexpressing ip1.Efs cells exhibited high efficiency in forming soft agar colonies, whereas the colony-forming efficiencies of the two ip1.E1A transfectants were strikingly reduced. These data suggested that E1A proteins can suppress the effect of the c-erbB-2/neu-overexpression in ovarian cancer cells and inhibit cell growth, DNA synthesis, and anchorage-independent growth.

3. E1A as a Tumor Suppressor Gene for c-erbB-2/neu-Overexpressing Human Ovarian Carcinoma SKOV3.ip1 Cells A critical test for E1A-mediated transformation suppression function in ovarian cancer cells is the ability of E1A to suppress tumor formation in vivo. Therefore, tumorigenicity assays were performed in mice that were injected s.o. with $3 \times 10^5$ cells from either the E1A-expressing ip1.E1A1 and ip1.E1A2 cell lines or the control ip1.Efs cell line (FIG. 14A). Like mice given injections of the parental SKOV3.ip1 cells, mice given injections of the control ip1.Efs cells formed tumors 7 days after injection and had huge tumor burdens of $3280 \pm 1310$ mm$^3$ by 80 days postinjection. However, nu/nu mice given injections of the same number of ip1.E1A1 transfectants did not form tumors until 21–30 days after injection, and their tumor burdens were only $460 \pm 170$ mm$^3$ by 80 days postinjection.

The tumor-suppressing function of E1A was more dramatic in mice given injections of the ip1.E1A2 transfectants, which did not induce tumors until 40–50 days postinjection, and 2 of 6 mice did not develop any tumor, even at 160 days postinjection. The tumor size in the four mice given injections of ip1.E1A2 were $290 \pm 220$ mm$^3$ at 160 days postinjection. Therefore, these results clearly demonstrated that E1A can suppress the tumorigenic potential of the ovarian carcinoma SKOV3.ip1 cells.

It is shown above that SKOV3.ip1 cells, when compared to SK-OV-3 cells, induced a higher mortality rate and shorter survival following i.p. injection into nu/nu mice. To determine whether E1A expression in SKOV3.ip1 cells could counteract the effect of c-erbB-2/neu overexpression and reduce the mortality rate, the inventors gave mice i.p. injections of the E1A-expressing ip1.E1A1 and ip1.E1A2 cell lines and the control ip1.Efs cell line. Mice given injections of $1 \times 10^4$ ip1.Efs cells developed tumor symptoms similar to those described in the previous section; one of the mice died of tumor as early as 19 days postinjection, and all of the other mice died within 75 days postinjection (FIG. 14A). However, there was a significant increase in survival for mice given injections of the E1A-transfected lines versus the parent SKOV3.ip1 and frameshift-transfectant ip1.Efs cell line (P<0.01) (FIG. 14B). The results indicated that E1A expression can reduce the mortality of mice given injections of c-erbB-2/neu overexpressing human ovarian carcinoma cells.

4. Discussion

The inventors have isolated a derivative cell line termed SKOV3.ip1 from the ascites that developed in mice given injections of human ovarian carcinoma SK-OV-3 cells. Compared with parental SK-OV-3 cells, the SKOV3.ip1 cell line expresses higher levels of c-erbB-2/neu-encoded p185 protein and corresponding exhibits more malignant phenotypes determined by in vitro and in vivo assays. This association between enhanced c-erbB-2/neu expression and more severe malignancy is very consistent with previous studies in which c-erbB-2/neu overexpression was shown to correlate with poor prognosis in ovarian cancer patients (Slamon et al., 1989).

The inventors data provided actual evidence to support those clinical studies that c-erbB-2/neu overexpression can be used as a prognostic factor for ovarian cancer patients and that c-erbB-2/neu overexpression may play an important role in the pathogenesis of certain human malignancies such as ovarian cancer. Although not important to the utility of the claimed invention, it will be interesting to further study the molecular mechanisms and biochemical pathways involved in c-erbB-2/neu overexpression and the associated malignant phenotype. The recent identification and molecular cloning of the ligands for the c-erbB-2/neu-encoded p185, which can increase the tyrosine phosphorylation of p185, will enable future direct examination of the molecular mechanisms and the biological effects of c-erbB-2/neu overexpression in human cancer and cancer metastasis (Peles et al., 1992; Holmes et al., 1992; Lupe et al., 1990; Yarden & Peles, 1991; Huang & Huang, 1992; Dobashi et al., 1991).

The adenovirus E1A gene was originally defined as a transforming oncogene that can substitute for the myo oncogene and simian virus 40 large tumor antigen gene in the ras cotransformation assay of primary embryo fibroblasts (Land et al., 1983; Ruley, 1983; Weinberg, 1985). As detailed herein, the inventors have found that E1A products can act as transformation and metastasis suppressors in the mutation-activated rat neu-transformed mouse 3T3 cells. In this particular example, it is further demonstrated that the E1A gene products effectively repressed c-erbB-2/neu gene expression in SKOV3.ip1 ovarian carcinoma cells, suppressed transformation phenotypes in vitro, and reduced tumorigenicity and mortality rate in vivo. These results indicate that the adenovirus E1A gene can function as a tumor suppressor gene for c-erbB-2/neu-over expressing human cancer cells as well as inhibit transformation induced by mutation-activated neu oncogene in rodent cells.

Since the inventors have previously demonstrated that E1A products can dramatically inhibit the c-erbB-2/neu mRNA level and c-erbB-2/neu-encoded p185 expression in human breast cancer cell lines, and have shown that the E1A gene products can repress neu gene expression at the transcriptional level by targeting at a specific DNA element in the neu gene promoter, it is likely that the reduced p185 expression in the ip1.E1A cell lines is due to transcriptional repression of the overexpressed c-erbB-2/neu gene, which may be one of the diverse molecular mechanisms that account for the tumor suppressor function of E1A in SKOV3.ip1 ovarian cancer cells. Interestingly, it has been shown that adenovirus E1A can render hamster cell lines more susceptible to lysis by natural killer cells and macrophages (Cook & Lewis, 1984; Sawada et al., 1985)

increased sensitivity to cytotoxicity by tumor necrosis factor in transfected NIH3T3 cells (Cook et al., 1989). Therefore, it is conceivable that the tumor-suppressing function of E1A may be partly due to an increased susceptibility to cytolytic lymphoid cells and molecules.

Recently, E1A protein was shown to induce a cytotoxic response that resembles programmed cell death (apoptosis) (Rao et al., 1992), which may also contribute to the tumor-suppressing function of E1A. In addition, E1A has been reported to convert three unrelated types of human cancer cells into a nontransformed state (Frisch, 1991). This suggests that E1A may also function as a tumor suppressor gene for certain human cancer cells in which c-erbB-2/neu is not overexpressed. It is not yet clear whether growth signals associated with the c-erbB-2/neu-encoded p185 protein might be activated in these human cancer cells and whether E1A might repress transforming phenotypes of these human cancer cells by blocking the signal transduction pathway associated with p185 protein via repressing c-erbB-2/neu expression; or E1A might suppress tumor formation through other mechanisms in certain human cancer cells. Despite the potential involvement of different molecular mechanisms, these results clearly establish E1A as a tumor suppressor gene for c-erbB-2/neu-overexpressing human ovarian cancer cells and indicate that E1A is a potential therapeutic reagent for the treatment of these human cancers.

It has been proposed that there are cellular "E1A-like" factors that may mimic the function of E1A in certain cell types (Nelson et al., 1990). Many common features between E1A and c-myc suggest that the c-myc gene product may be one of the cellular homologue of the E1A protein. These common features include the following: E1A and c-myc share a similar structural motif (Figge & Smith, 1988; Figge et al., 1988); both E1A and c-myc can transform primary embryo fibroblasts in cooperation the ras oncogene (Land et al., 1983; Ruley, 1983); both can bind specifically to the human Rb gene product, the RB protein (Whyte et al., 1988; Rustgi et al., 1991); both can induce apoptosis in certain cell types (Rao et al., 1992; Frisch, 1991; Nelson et al., 1990; Figge & Smith, 1988; Figge et al., 1988; Whyte et al., 1988; Rustgi et al., 1991; Evan et al., 1992); and both have been shown to block transformation of certain transformed cell lines (Frisch, 1991; Nelson et al., 1990; Figge & Smith, 1988; Figge et al., 1988; Whyte et al., 1988; Rustgi et al., 1991; Evan et al., 1992; Suen & Hung, 1991). In addition, the inventors have found that, similar to the E1A proteins, the c-myc gene product can repress c-erbB-2/neu gene expression at the transcription level, resulting in reversal of the neu-induced transformed morphology in NIH3T3 cells (Wang et al., 1991). Whether c-myc can suppress the malignancy of c-erbB-2/neu-overexpressing human cancer cells is an interesting issue that the inventors propose to examine.

E1A can inactivate the Rb tumor suppressor gene by complexing the Rb gene product, Rb protein, and by inducing RB protein phosphorylation (Whyte et al., 1988; Rustgi et al., 1991; Evan et al., 1992; Suen & Hung, 1991; Wang et al., 1991). Therefore, the inventors have recently examined whether RB might also regulate c-erbB-2/neu expression. Similar to E1A, RB can also repress c-erbB-2/neu gene expression at the transcriptional level (Yu et al., 1992). The cis-acting elements responding to E1A and RB are different but only a few base pairs away from each other. It will be interesting to study further the possibility that E1A and RB might interact with each other to regulate c-erbB-2/neu transcription.

The E1A gene of adenovirus 2, a close sera type of adenovirus 5, was shown to reduce the metastatic potential of ras-transformed rat embryo cells Pozzatti et al., 1988). It was hypothesized that the Ad-2 E1A gene may regulate the expression of one or more cellular genes that contribute to the metastatic phenotype and expression of nm23, a gene associated with low metastatic potential in certain cell types that was subsequently shown to be elevated in E1A-expressing ras-transformed rat embryo cells (Steeg et al., 1988). Although the inventors have found that E1A can repress c-erbB-2/neu gene expression and suppress the metastatic potential of c-erbB-2/neu-transformed 3T3 cell, the c-erbB-2/neu gene expression levels in the parental ras-transformed rat embryo cells and E1A-expressing ras-transformed rat embryo cells is not known. Therefore, it is not clear at this moment whether repression of c-erbB-2/neu gene expression contributes to the metastasis suppression function of E1A in ras-transformed rat embryo cells.

One of the interesting issues on the correlation between c-erbB-2/neu overexpression and poor clinical outcome in human breast and ovarian cancers is whether c-erbB-2/neu overexpression is the result of an aggressive tumor or has a causative role for aggressive tumors. The data presented here support a direct role for c-erbB-2/neu overexpression in the pathogenesis of aggressive tumors. First, comparison of the SK-OV-3 cell line and the derivative SKOV3.ip1 cell line revealed a direct relationship between an increased c-erbB-2/neu expression level and an enhanced malignant phenotype measured by in vitro and in vivo assays. Second, c-erbB-2/neu expression in the E1A-expressing ip1.E1A cells was dramatically repressed, and, accordingly, the malignant potential of these cells was diminished. Taken together, these observations argue for a causative role of c-erbB-2/neu overexpression in the more malignant tumor pattern. Since c-erbB-2/neu-overexpressing ovarian tumors may be more malignant, more aggressive therapy might be beneficial to those ovarian cancer patients whose tumors overexpress c-erbB-2/neu-encoded p185.

EXAMPLE V

Suppression of the Neu Promoter with LT

1. Materials and Methods a. Cell Culture

NIH 3T3, B104-1-1 and Rat-1 cells were maintained in 5% $CO_2$ in Dulbecco's modified Eagle's medium (DMEM/F-12) supplemented with 10% calf serum and 100 IU/mL penicillin and 100 mg/mL streptomycin. Cells transfected with the drug selection plasmid, pSV2neo, were grown in the above media containing 400 mg/mL G418.

b. Plasmids

The following plasmids have been described: neu deletion-CAT constructs (Suen et al., 1990), EGF receptor-CAT construct, pERCAT-9 (37), plasmid encoding activated genomic neu, cNeu-104 (Hung et al., 1986) and control filler plasmid, pSV2E (Suen et al., 1990). Two LT encoding plasmids were used, pZ189 or pVU-0, both of which showed similar results. Plasmids pVU-0 (Seidman et al., 1985) and mutant LT encoding plasmids, pK1 and pK7 (Kalderon et al., 1984).

c. Stable Transfections

The drug selection plasmid pSV2neo was cotransfected with plasmids encoding LT into B104-1-1 cells. The transfected plates were trypsinized after 48 h and split into 4 plates and subsequently maintained in media containing 400 mg/mL G418. After 3 weeks, colonies were isolated and established in media containing G418).

d. Transient Transfections and CAT Assays

Cells were transfected using the modified calcium phosphate precipitation technique (Chen et al., 1987). Cells were harvested 48 h after transfection and cell extracts obtained by freeze-thawing. For transfections involving LT, the protein concentration was determined using an aliquot of the extract. Aliquots of extracts containing equal amounts of protein were used for CAT assay (Gorman et al., 1982). Transfections and CAT assays were repeated 3–4 times and representative data is shown.

e. Immunoblotting

Immunoblotting was done as described (Matin et al., 1990). Confluent cells grown in 10-cm dishes were washed and lysed with lysis buffer and 100 mg protein was loaded for electrophoresis on SDS-polyacrylamide gels followed by transfer to nitrocellulose. To detect expression of p185, blots were incubated with anti-neu antibody (c-neu, Ab-3, Oncogene Science, Manhasset, N.Y.), then reacted with secondary antibody, goat anti-mouse conjugated with horse radish peroxidase. The nitrocellulose was subsequently developed with horse radish peroxidase substrate, 4-chloro-1-napthol and hydrogen peroxide. To analyze the expression of LT antigen, blots were probed with monoclonal antibody specific for LT (SV 40 T-Ag, Ab-2, Oncogene Science). Blots were incubated with 1 mg/mL [125I]-protein A. After further washing, dried blots were exposed for autoradiography.

f. Southern Blotting

Genomic DNA was harvested from cells and digested with Bam H1 for Southern blotting as described (Zhang et al., 1989). Blots were hybridized using 32P-labeled rat neu cDNA probe.

g. Focus Forming Assay

Focus forming assay was carried out as described (Yu et al., 1992). The cosmid clone, cNeu-104 (Hung et al., 1986), contains 30 kb of activating genomic rat neu including 2.2 kb of the neu promoter. cNeu-104 (0.5 mg) was cotransfected into normal fibroblasts (Rat-1 cells) with 0.1 mg of the drug selection plasmid, pSV2neo, and 5–10 mg plasmids encoding mutant LT (pK1) or control filler plasmid, pSV2E. Cells were trypsinized and split into 4 plates 48 h after transfection. Two plates were maintained in regular media while the other 2 plates were maintained in media supplemented with G418. For cells kept in regular media for 3 weeks, foci of transformed cells appeared on a background monolayer of nontransformed cells. G418 resistant colonies appeared for plates maintained in G418 media. Foci and G418 resistant colonies were stained with 1% crystal violet and counted. To normalize for transfection efficiency, the number of foci formed for each transfection was divided by the number of G418 colonies obtained.

2. Results a. LT Reduces Neu-Encoded p185 Levels in Cells that Overexpress p185

To test the effect of LT in cells that overexpress neu encoded p185, plasmids encoding LT, pZ189 (driven by the SV 40 promoter), together with pSV2neo (plasmids encoding the gene for neomycin resistance) were cotransfected into B104-1-1 cells. B104-1-1 cells are derived from NIH 3T3 cells transformed by the mutation-activated genomic rat neu oncogene (Shih et al., 1981; Hung et al., 1986). B104-1-1 cells express high levels of activated neu encoded p185, are phenotypically transformed (Padhy et al., 1982; Shih et al., 1981), highly tumorigenic (Yu et al., 1991; Hung et al. 1989) and have increased metastatic potential (Yu et al., 1991; Yu et al. 1992). The LT-transfected and G418 resistant B104-1-1 cells were cloned after 3 weeks and 2 cell lines expanded from the clones (named BTn14 and BTn16 cell lines) were analyzed for expression of LT and p185. Immunoblotting of cell lysates for LT using anti-LT antibody (SV 40 T-Ag, Ab-2, Oncogene Science), showed 2 bands of molecular weights less than 111 kd indicating expression of LT in BTn14 and BTn16 cell lines (FIG. 15-B, lanes 1 and 2). The bands are probably different phosphorylated forms of LT, as reported previously (Livingston et al., 1987). A control cell line, BEn5, was generated by transfecting B104-1-1 cells with pSV2neo and pSV2E (control plasmid similar to pZ189, containing the SV 40 promoter but lacking the LT coding region). As expected, BEn5 and NIH 3T3 cells do not express LT (FIG. 15-B, lanes 3 and 4).

The level of neu encoded p185 in these cell lines by immunoblotting whole cell lysates with monoclonal anti-p185 antibody (c-neu Ab-3, Oncogene Science), which recognizes the carboxy terminus of p185 was then analyzed. The control cell line, BEn5, expresses a high level of rat neu encoded p185 (FIG. 15-A, lane 3) similar to parental B104-1-1 cells (data not shown). No p185 expression was detected in the negative control cells, NIH 3T3, using this antibody and detection system (FIG. 15-A, lane 4). The two cell lines expressing LT antigen (BTn14 and BTn16 cell lines) had significantly lower levels of p185 expression (FIG. 15-A, lanes 1 and 2) compared to BEn 5 cell line which does not express LT. The expression of p185 in the LT transfected cells decreased by approximately 60% to 80%. BTn16 cells (FIGS. 15-A & B, lane 1) expressed higher levels of LT and had lower p185 expression, suggesting an inverse correlation between LT expression and p185 level.

To ensure that the decreased expression of p185 was not due to decreased copy number of rat genomic neu oncogene, the level of rat neu DNA in these cells was analyzed by Southern blot analysis. The levels of genomic rat neu oncogene in the BTn14 and BTn16 cell lines (FIG. 15-C, lanes 1 and 2) were equivalent to that in BEn5 cell line (FIG. 15-C, lane 3). The parental NIH 3T3 cells used as control does not have rat neu DNA. These studies show that when LT is stably expressed in cells that originally express high levels of neu-encoded p185, there is a resulting decrease in the level of p185, indicating that LT, similar to c-myc and E1A, can repress neu expression.

b. LT Specifically Inhibits the Neu Promoter

To determine whether the LT antigen inhibited rat neu expression at the transcriptional level, the effect of LT on the upstream regulatory sequences of neu using transient transfection assays was examined. Plasmids encoding LT antigen (pVU-0 or pZ 189) (Kalderon et al., 1984) were cotransfected with plasmids encoding 2.2 kb rat neu upstream regulatory sequences linked to a reporter chloramphenicol acetyl transferase (CAT) gene (pNeuEcoR1CAT) (Suen et al., 1990) into NIH 3T3 cells. The control plasmid, pSV2E, was used as a filler plasmid to adjust concentrations in cotransfections. About 80% inhibition of the 2.2 kb neu promoter activity was achieved by a 10-fold excess of LT plasmid (FIG. 16, lanes 1 & 2). The inhibitory activity of LT was specific to neu since the activity of the epidermal growth factor receptor regulatory sequence (pEGFrCAT) (Johnson et al., 1988) was unaffected by a similar amount of LT (FIG. 16, lanes 3 & 4). In addition, LT had a dose dependent effect on the activity of the regulatory sequences of neu as increasing amounts of LT led to decreased CAT activity of pneuEcoR1CAT (FIG. 17). Thus, LT specifically inhibits the activity of the rat neu promoter.

c. Repression of Neu by LT is Mediated Through the Xho1-Nar1 Region

The region of the 2.2 kb neu regulatory sequence that responds to LT was mapped. To this end, series deletion constructs of the neu regulatory sequence-CAT (FIG. 18-A) (Suen et al., 1990) were cotransfected with plasmid encoding LT into NIH 3T3 cells. FIG. 18-B shows that the CAT activity of each of the neu-deletion constructs and the inhibition of this activity in the presence of LT (pVU-0 or pZ189). There was a 70%–80% inhibition of the CAT activity of most of the neu-deletion constructs except for pneuXba1 CAT and pNeuEcoRV2CAT. In repeated studies, the inventors found less repression by LT of these two constructs. Overall, the activity of all the deletion constructs, including pneuXho1 CAT, were repressed by LT. This indicates that repression of neu by LT is mediated through the 94 base pair Xho1-Nar1 region (−172 to −79, relative to first ATG) of the rat neu promoter.

S1 protection studies have identified four transcription initiation sites in the rat neu promoter. Three of them, including the two major sites (at −158 and −147) are within 30 bp downstream of the Xho1 site (Suen et al., 1990). Further deletions of nucleotides were made downstream of the Xho1 site using Bal 31 digestion (Yanisch-Perron et al., 1985). However, this led to dramatic reduction of activity of the neu promoter (data not shown). Thus the Xho1-Nar1 region of neu encompasses the minimum promoter of the rat neu gene and LT inhibits the activity of the minimum promoter of neu.

Gel-shift assays indicated that the 94 base pair Xho1-Nar1 DNA fragment specifically complexes with proteins in the nuclear extract of NIH 3T3 cells (FIG. 19, lane 1). The complex, A, is detected using gels with large pore size (4.5% gels, acrylamide: bisacrylamide=80:1) which have been previously shown to detect large DNA-protein complex involved in transcription initiation (Dynlacht et al., 1991), but not with gels with smaller pore size (acrylamide: bisacrylamide=29:1) (data not shown). This suggests A is a large DNA-protein complex that may involve factors in the initiation or elongation complex for neu transcription. However, nuclear extracts from cells that express LT, BTn 14 cell line, also gave a similar DNA-protein complex profile in such gel-shift assays (FIG. 19, lane 3). Thus, the presence of LT in the nuclear extract did not affect the mobility of complex A. One explanation of this is that complex A is already so large that the presence of LT (in nuclear extracts from BTn 14 cells) does not create a observable difference in the shift. Indeed, complex A is found very near the top of the gel and is a broad band suggesting the present of multiple types of DNA-protein complexes. Another possibility is that LT has indirect or subtle effects on complex A at the Xho1-Nar1 fragment such as a change in phosphorylation of protein factors or a change in conformation of some factors that can not be detected by gel-shift assays.

d. A Non-Transforming Mutant of LT (K1) is a Suppressor of Neu

LT and Rb are known to form a protein complex (DeCaprio et al., 1988) and Rb also modulates neu expression (Yu et al., 1992), therefore, it might be expected that the LT-Rb complex is involved in repression of neu. To examine this, an available mutant of LT (K1) was utilized. K1 has a single amino acid change within the region required for Rb binding (amino acids 105–114 of LT) (FIG. 20-A) (Kalderon et al, 1984). K1 expresses mutant LT protein which is unable to complex Rb (DeCaprio et al, 1988) and K1 is defective for transformation as assayed by focus forming assay in Rat-1 cells Kalderon et al., 1984; Cherington et al., 1988).

pneuXho1CAT together with plasmids encoding wild type (pVU-0) or mutant LT (K1) were cotransfected into NIH 3T3 cells. Surprisingly, K1 represses neu as effectively as wild type LT (FIG. 20-B). Therefore, complex formation between LT and Rb is not required for LT-mediated neu repression.

K1, unlike wild type LT, is unable to transform Rat-1 cells in focus forming assays (Kalderon et al., 1984). Therefore, the above results raises an interesting question whether K1 may function as a transformation suppressor of activated neu in Rat-1 cells. To test this possibility, focus forming assays were carried out to determine the effect of stably transfecting K1 with activated genomic neu. The plasmid cNeu-104 encodes the activated genomic neu which has a single point mutation in the transmembrane domain and is driven by 2.2 kb of neu upstream regulatory sequences (Hung et al., 1986). Upon introduction of cNeu-104 into normal Rat-1 fibroblasts, those cells that stably express activated neu are transformed and 3–4 weeks later form visible foci on a background of normal monolayer cells. When K1 was cotransfected with cNeu-104 into Rat-1 cells, it led to 50% reduction in the number of foci formed by cNeu-104 (FIG. 20-C). Transfection of K1 only does not induce any foci. Suppression of neu-transforming activity with wild type LT (pVU-0) is complicated by the fact that wild type LT itself forms transformed foci in Rat-1 cells (data not shown) which makes it impossible to analyze the data. Therefore, mutant LTs unable to complex with Rb that act as transformation suppressors of activated neu may be the most clinically useful of the LT gene products.

3. Discussion

The results of these studies show that the function of the rat neu promoter is suppressed by the transforming viral oncoprotein, SV 40 LT antigen. This activity of LT is similar to that observed for the adenovirus 5 E1A and the c-myc oncoproteins, with whom LT shares a few structural and functional similarities but striking differences. The inhibitory activity of LT is apparent in the LT-transfected stable cell lines which showed an inverse correlation of neu p185 to LT protein expression. Thus, expression of LT in cells leads to reduced expression of neu encoded p185 in cells.

LT inhibits neu by repressing the activity of the minimum neu promoter. Series deletion analysis of the upstream regulatory sequences of neu showed that repression by LT is mediated through the 94 bp Xho1-Nar1 region of the neu gene, which contains the minimum promoter 30 bp downstream of the Xho1 site. This result is unlike that of c-myc and E1A, since these repress neu through an upstream region of the regulatory sequences of neu. Thus LT mediates repression of neu through a different pathway compared to c-myc and E1A. Therefore, these structurally related oncogenes repress the activity of the neu promoter by acting through different regions of the regulatory sequences of neu. Although the promoter of the epidermal growth factor receptor and the promoter of neu share some common features (Suen et al., 1990; Johnson et al., 1988), LT did not inhibit the activity of the promoter of epidermal growth factor receptor. Thus, LT specifically affects the promoters of certain growth factor receptors.

Since LT mediates repression of neu through the Xho1-Nar1 region which contains only minimum sequence upstream of the two major transcription initiation sites, it is possible that LT may modulate transcription initiation or elongation from the neu promoter. LT is known to interact with cellular transcription factors such as AP-2 and abrogate its function (Mitchell et al., 1987). However, examination of the 94 bp sequences within Xho1-Nar1 revealed no motif with significant homology to the AP-2 (Suen et al., 1990).

EXAMPLE VI

Suppression of Neu-Mediated Cancer with LT

1. Suppression of Neu-Mediated Cancer by LT in Mice

The inventors are conducting ongoing studies of the abilities of pK1 to suppress the growth and metastasis of neu-overexpressing human ovarian cancer cells (SK-OV-3 cells) in female homozygous nu/nu (nude) mice. SK-OV-3 cells express high levels of neu and are highly metastatic in nude mice (Yu et al. 1993). These studies involve treatment of these mice with a liposomal complex liposomes comprising lipids and pK1. pK1 comprises DNA encoding a non-transforming mutant of LT (Kalderon et al. 1984). Details of this study are given in VII, 2.

2. LT Suppression of Neu-Mediated Cancer in Humans.

The results obtained using the cell lines and animal models described in this application are of the type widely accepted by those of skill in the art as being predictive of success in human treatment regimens. Indeed, clinical trials concerning the use of LT to suppress the expression of neu in humans are contemplated. However, due to precautions which are necessarily attendant to every new pharmaceutical, the compositions and methods of the present invention have not yet been tested in such a clinical setting. Nevertheless, the results presented herein reasonably demonstrate that LT will be useful in combating cancers which exhibit neu-overexpression, such as breast cancers, ovarian cancers, lung cancer, gastric cancer, oral cancers and prostate cancer.

One of the initial clinical trials to be performed involves non-transforming mutants of LT, for example K1. These non-transforming mutants have demonstrated the ability to suppress neu-mediated cancers in both cell cultures studies and in vivo animal model studies. The use of such mutants avoids potential problems with transformation. In these clinical studies, K1 will be introduced into the human cancer cells to suppress the production of neu.

Among those patients who will benefit from this therapy are those whose cancer cells express high levels of neu. The level of neu expression in a given patient can be determined by analysis of biopsy samples of cancer tissue using routine techniques such as immunohistochemistry or western blotting. These diagnostic techniques are routinely practiced and well known to those of skill in the art.

Targeting of cancerous tissues overexpressing neu may be accomplished in any one of a variety of ways. Plasmid vectors and retroviral vectors, adenovirus vectors, and other viral vectors all present means by which to target human cancers. The inventors anticipate particular success for the use of liposomes to target LT genes to cancer cells. In one of the first series of clinical phase to be performed, DNA encoding nontransforming mutants of LT such as K1 will be complexed with liposomes in the manner described in Example VII, and this DNA/liposome complex will be injected into patients with certain forms of cancer, such as breast cancer, intravenous injection can be used to direct the K1 gene to all cells, including those which overexpress neu. Directly injecting the liposome complex into the proximity of a cancer can also provide for targeting of the complex with some forms of cancer. For example, cancers of the ovary can be targeted by injecting the liposome mixture directly into the peritoneal cavity of patients with ovarian cancer. Of course, the potential for liposomes that are selectively taken up by a population of cancerous cells exists, and such liposomes will also be useful for targeting the LT gene.

Those of skill in the art will recognize that the best treatment regimens for using LT to suppress neu-mediated cancers can be straightforwardly determined. This is not a question of experimentation, but rather one of optimization, which is routinely conducted in the medical arts. The in vivo studies in nude mice provide a starting point from which to begin to optimize the dosage and delivery regimes. The frequency of injection will initially be once a week, as was done in the mice studies. However, this frequency might be optimally adjusted from one day to every two weeks to monthly, depending upon the results obtained from the initial clinical trials and the needs of a particular patient. Human dosage amounts can initially be determined by extrapolating from the amount of LT used in mice, approximately 15 $\mu$g of plasmid DNA per 50 g body weight. Based on this, a 50 kg woman would require treatment with 15 mg of DNA per dose. Of course, this dosage amount may be adjusted upward or downward, as is routinely done in such treatment protocols, depending on the results of the initial clinical trials and the needs of a particular patient.

3. Liposomal Transfection with E1A and/or LT to Suppress neu-Mediated Cancers

One particularly useful way to use E1A and/or LT to repress neu-mediated phenotypes is via the use of liposomes for carrying the suppressor's DNA into the oncogenic cells.

EXAMPLE VII

Preparation of Liposome/DNA Complexes and Prevention of Neu-Mediated Tumors with the Complexes 1. Preparation of Liposomes Catatonic liposomes which are efficient transfection reagents for both the E1A and LT genes for animal cells can be prepared using the method of Gao et al. (1991). Gao et al. describes a novel catatonic cholesterol derivative that can be synthesized in a single step. Liposomes made of this lipid are reportedly more efficient in transfection and less toxic to treated cells than those made with the reagent Lipofectin. These lipids are a mixture of DC-Chol ("3$\beta$(N-(N'N'-dimethylaminoethane)-carbamoyl cholesterol") and DOPE ("dioleoylphosphatidylethanolamine"). The steps in producing these liposomes are as follows.

DC-Chol is synthesized by a simple reaction from cholesteryl chloroformate and N,N-Dimethylethylenediamine. A solution of cholesteryl chloroformate (2.25 g, 5 mmol in 5 ml dry chloroform) is added dropwise to a solution of excess N,N-Dimethylethylenediamine (2 ml, 18.2 mmol in 3 ml dry chloroform) at 0° C. Following removal of the solvent by evaporation, the residue is purified by recrystallization in absolute ethanol at 4° C. and dried in vacuo. The yield is a white powder of DC-Chol.

Cationic liposomes are prepared by mixing 1.2 $\mu$mol of DC-Chol and 8.0 $\mu$mol of DOPE in chloroform. This mixture is then dried, vacuum desiccated, and resuspended in 1 ml sterol 20 mM HEPES buffer (pH 7.8) in a tube. After 24 hours of hydration at 4° C., the dispersion is sonicated for 5–10 minutes in a sonicator form liposomes with an average diameter of 150–200 nm.

To prepare a liposome/DNA complex, the inventors use the following steps. The DNA to be transfected is placed in DMEM/F12 medium in a ratio of 15 $\mu$g DNA to 50 $\mu$l DMEM/F12. DMEM/F12 is then used to dilute the DC- Chol/DOPE liposome mixture to a ratio of 50 µl DMEZM/ F12 to 100 µl liposome. The DNA dilution and the liposome dilution are then gently mixed, and incubated at 37° C. for 10 minutes. Following incubation, the DNA/liposome complex is ready for injection.

2. In Vivo Treatment of Neu-Mediated Cancer Via Liposomes

The inventors have shown that liposome-mediated direct gene transfer techniques can be employed to obtain E1A suppression of neu-overexpressing human cancer cells in living host. The protocol for this study was as follows.

Female nude mice (5–6 weeks old) were given intraperitoneal injections of SK-OV-3 cells ($2 \times 10^6$/100 µl). SK-OV-3 cells are human ovarian cancer cells that have been shown to grow within the peritoneal cavity of nude mice. After five days, the mice were given intraperitoneal injections of various compounds. Some mice were injected with E1A DNA alone, some were injected with liposome/E1A DNA complex prepared in the manner described above, and some were injected with liposome/Efs (an E1A frameshift mutant) DNA complex. 200 µl of a given compound was injected into a given mouse. After the initial injections, injections were repeated every seven days throughout the life of the mouse.

FIG. 21 shows the results of this study. Mouse 1, was injected with E1A DNA alone and developed extensive bloody ascites. Mouse 1 died 65 days after the injection of the SK-OV-3 cells. Mouse 2 was injected with liposome/Efs DNA complex. Mouse 2 developed extensive bloody ascites and a large tumor and died 76 days after injection of the SK-OV-3 cells. Mouse 3 was injected with the liposome/ E1A DNA complex. This mouse looked healthy and normal and was still alive 160 days after the injection of the SK-OV-3 cells.

These results indicate that liposome-mediated E1A gene transfer can inhibit neu-overexpressing human ovarian cancer cell growth. Therefore, it is predictable that liposome-mediated E1A or LT gene therapy may serve as a powerful therapeutic agent for HER-2 neu-overexpressing human ovarian cancers by direct targeting of E1A or LT at the HER-2 neu-oncogene.

The inventors are presently testing the effects of the LT mutant pK1 on the growth and metastasis of the human ovarian cancer cells SK-OV-3 in essentially the same manner as used to test the effects of E1A on these cells. In these experiments, nude mice were intraperitoneally injected with $1.8 \times 10^6$ SK-OV-3 cells per ml of phosphate buffered saline. The following week, and every week thereafter, the mice were injected with 15 µg pK1 in suspension with 1 µmol liposome (DC-Chol-containing liposomes prepared as previously described). As controls, 5 mice were injected with SK-OV-3 cells and then injected with the control plasmid pGEM liposomes every week. Based on the fact that previous data has shown that pK1 can suppress neu-induced foci and transcription from the neu gene promoter, it is expected that the injected pK1 will reduce tumor growth of the SK-OV-3 cells in the mice.

3. Liposomal Transfection with E1A and/or LT to Treat Humans

Based on the results of the in vivo animal studies described above, those of skill in the art will understand and predict the enormous potential for human treatment of neu-mediated cancers with E1A and/or LT DNA complexed to liposomes. Clinical studies to demonstrate these affects are contemplated. One set of such studies is described in Example VII, 2. where clinical trials involving the use of LT complexed to liposomes are described. E1A or any other neu-suppressing gene product may be complexed with liposomes and employed in human studies in a manner similar to that described for LT. These clinical trials are anticipated to show utility of LT, E1A, and other neu-suppressing gene products for the treatment of neu-overexpressing cancers in humans. Dosage and frequency regimes will initially be based on the data obtained from in vivo animal studies, as was described in Example VI, 2.

EXAMPLE VIII

Adenoviral E1A Gene Therapy of Human Cancers Expressing High Levels of P185

The present example provides for the introduction of the E1A or LT gene for treatment of human cancers expressing high levels of P185. This may be achieved most preferably by introduction of the desired gene through the use of a viral vector to carry either the E1A or LT sequences to efficiently infect the tumor, or pretumorous tissue. These vectors will preferably be an adenoviral, a retroviral, a vaccinia viral vector or adeno-associated virus (Muro-cacho et al., 1992). These vectors are preferred because they have been successfully used to deliver desired sequences to cells and tend to have a high infection efficiency. The inventors have conducted studies showing that native adenovirus can be employed to transfer the E1A gene in accordance with the invention. However, a particularly preferred type of adenovirus is the group of replication-deficient adenoviruses.

The HER-2/neu oncogene encodes a MW 185,000 epidermal growth factor receptor-related transmembrane protein (p185) with intrinsic tyrosine kinase activity. Overexpression of the normal human HER-2/neu protooncogene, which can also lead to higher overall tyrosine kinase activity, is a frequent event in many types of human cancers, including cancers of the breast, ovarian, lung, uterine cervix, stomach and colon cancer, for example Correlation between the overexpression of HER-2/neu and the number of lymph node metastases in breast cancer patients and decreased survival in both breast and ovarian cancer patients has been reported. The present inventors have shown in the previous examples that adenovirus 5 E1A gene product can repress HER-2/neu oncogene expression and suppress the tumorigenic and metastatic potential of activated rat neu oncogene-transformed mouse 3T3 cells. Introduction of the E1A gene into the human ovarian cancer cell line SK-OV-3(i.p.), which has enhanced expression of HER-2/neu, resulted in reduced malignant phenotypes in vitro and in vivo. Those data indicated that the E1A gene can be considered as a tumor suppressor gene for HER-2/neu overexpressing human cancer cells.

Replication-deficient adenovirus represents a gene delivery system that should be able to efficiently transfer an exogenous gene directly to tumor cells in vivo. Unlike vectors that require target cell replication for gene transfer, such as retrovirus which can only infect proliferating cells, adenovirus can transfer genes into both proliferating and non-proliferating cells. The extrachromosomal location of adenovirus in the cells (non-integration) decreases the chance of activating cellular oncogenes. A high titer of adenovirus is easily produced and purified. Replication-deficient adenovirus containing E1A was constructed by E3 and E1B deletion mutant (E1B and E3 is required for adenovirus replication), control virus was constructed by additional E1A deletion mutant.

The present example provides for the transduction of replication-deficient adenovirus containing E1A gene

[Ad.E1A(+)] into human cells in vitro and in vivo. Tumor suppressor gene E1A was efficiently transduced into human ovarian cancer cell SK-OV-3(i.p.) cells by Ad.E1A(+) in vitro and in vivo (FIG. 22 and FIG. 26). Up to 100% of the cells can be infected at either the virus/tumor ratio >50/1 or at lower ratios with multiple infections. Tumor growth in vitro (FIG. 23) and colony formation ability in soft agarose (FIG. 24) were greatly inhibited by Ad.E1A(+). SK-OV-3 (i.p.) ($10^6$/mouse) was transplanted into the peritoneal cavity of nu/nu mice. Five days later they received an intraperitoneal injection of viral solution (titer: $2 \times 10^9$ PFU/ml) from either Ad.E1A(+), Ad.E1A(−), or Just PBS for 3 days, followed by once/week for 4.5 months. Clinical observation and survival rates showed that Ad.E1A(+) significantly prolonged the survival time of the mice and some mice were kept tumor free (FIG. 25). Histoimmunochemical analysis indicated that Ad.E1A protein was expressed in tumor tissue after gene delivery in vivo and expression of HER-2/neu P185 protein was greatly suppressed (FIGS. 28A–28C).

The ovarian cancer cell line 2774, which has a very low level of expression of HER-2/neu P 185 protein, was also tested for the therapeutic effect of Ad.E1A(+) (FIG. 27). Results showed that Ad.E1A(+) can not significantly prolong the survival rate of the 2774 cell line, indicating that Ad.E1A(+) specifically targets P185 high expression tumor cells.

An orthotopic human lung cancer model in nu/nu mice was used to study the effect of Ad.E1A(+) on tumor growth of human lung cancer cell line NCI-H820 expressing a high level of P185 in vivo. Mouse tumor cells ($5 \times 10^6$), were inoculated intratracheally. Five days later, mice were treated by intratracheal instillation of viral solution (titer: $2 \times 10^9$ PFU/ml) of Ad.E1A(+), Ad.E1A(−), or PBS, followed by once/week i.v. injection treatment for 2.5 months. At autopsy, more than 80% of control mice but only 20% of treated mice had tumors as shown in Table 3 and FIGS. 29A–29C.

TABLE 3

THERAPEUTIC EFFECT OF Ad.E1A ON LUNG CANCER H820 IN NU/NU MICE

|  | Ad.E1A(+) | Ad.E1A(−) | PBS |
|---|---|---|---|
| No. mice with tumor/total (%) | 1/5 (20%) | 4/5 (80%) | 5/5 (100%) |
| Mean volume + SD (cm³) | 0.31 | 0.59 + 0.29 | 0.43 + 0.27 |

Human non-small cell lung cancer line NCI-H820 that has high expression of HER-2/neu was injected intratracheally into nu/nu mice ($5 \times 10^6$/mouse) via a tracheotomy incision. Five days later, the mice were treated once with intratracheal injection (0.1 ml) of either PBS, or Ad.E1A(−), Ad.E1A(+) (Viral titer: $2 \times 10^9$ PFU/ml), followed by weekly i.v. injection treatment for 2.5 months. Then, mediastinal blocks were removed and tumor volume was calculated. The results indicate that Ad.E1A(+) can prevent the growth of human lung cancer cells implanted orthotopically in nu/nu mice.

From the above data, it is clear that the adenoviral gene delivery system is effective and that Ad.E1A(+) has a therapeutic effect on HER-2/neu expressing human ovarian and lung cancer tumors.

EXAMPLE IX

Chemosensitization of neu-Overexpressed Cancer Cells to Taxol by Adenovirus 5 E1A The present Example relates to HER-2neu-targeting genetic therapy by E1A combined with chemotherapy in breast cancer cell lines.

In order to examine the effects of taxol on cell growth rat fibroblasts with various neu and E1A expression were grown in varying concentrations of taxol 0.01–100 μM. The cell lysates were subsequently run through 8% SDS-PAge and blotted with anti-p185 and anti-E1A antibodies (FIG. 30A). The effects on cell growth were measured using the MTT assay as described earlier. The highest inhibition of cell growth was seen in B.E1A1.Hy with neu down-regulated by E1A in a taxol concentration of 0.1–10 μM (FIG. 30B).

Preparation of Adenoviruses Against Breast Cancer Cell Lines

Three replication-defective adenoviral vectors were prepared in this study: Ad.E1A(+), an adenovirus type 5 containing E1A but lacking E1B and E3 (dl324); control vector Ad.E1A(−) lacks E1A (dl312); and Ad.RSVlacZ, an adenovirus type 5 vector lacking E1A, E1B, and E3, and containing the Rous sarcoma virus long terminal repeat as a promoter driving the *E. coli* lacZ gene (coding for the λ-gal protein).

Establishment of Transduction Efficiency of Adenoviruses Against Breast Cancer Cell Lines (In Vitro)

Four different breast cancer cell lines, MDA-MB-435 and MDA-MB-231, which express low level of neu, and MD-MB-453, MDA-MB-361, which express high level of neu, were treated with Ad.RSVlacZ at different virus/tumor cell (V/T) ratios. Two days later, the cells were fixed and stained with X gal, which turned the lacZ gene blue. The efficiency increased with higher V/T ratio. Transduction efficiency of Ad.RSVlacZ was the highest among neu-overexpressing breast cancer cell lines (FIG. 31A). With a V/T ratio of 200:1, almost 100% transduction efficiency was obtained for MDA-MB-361, and MDA-MB-453. Cytopathic toxicity was observed with V/T ratios above 400:1. Low-expressing neu breast cancer cell lines were difficult to transduce due to rapid increase in the cell counts. Transduction efficacy was about 20–30% with V/T ratio of 200:1. In a high infection protocol, which depletes FBS, infection efficiency was higher than 95% can be obtained in MDA-MB435, with a V/T ratio of 400:1 and MDA-MB-453, with a V/T ratio of 200:1 (FIG. 31B).

The HER-2/neu-overexpressing breast cancer cell line MDA-MB-453 was treated with Ad.E1A(+) and Ad.E1A(−) at different V/T ratios (50:1, 100:1, 150:1, and 200:1). Our observations showed that within 2 days, there was an expression of E1A protein with dose-dependent correlation by western blot analysis with anti-E1A antibody. A virus/ tumor cell ratio of 200:1 of Ad.E1A)+) had a maximum effect on down regulating HER-2/neu expression (p185) by western blot analysis with anti-p185 antibody (FIG. 32A). There was no down-regulation among cells that were treated with Ad.E1A(−). Among low expression HER-2/neu breast cancer cell lines, there was no change in the low expression of HER-2/neu (FIG. 32B).

With maximum down-regulation of HER-2/neu expression (p185) 2 days after giving V/T ratio of 200:1 Ad.E1A (+) against MDA-MB-453, we have conducted a cytoxic assay using MTT (3-[4,5-dimethylthiazol-2yl]-2,5-diphenyl tetrazolium bromide) assay. An appropriate control of Ad.E1A(−) (dl312), Ad.E1A(−) with Taxol, Taxol alone, and Ad.E1A(+) alone (dl324) were prepared and compared with Ad.E1A(+) with Taxol. Taxol was given from 0.1 μM to 100 μM. We showed a maximum suppression of survival fraction of MDA-MB-453 cells when both Ad.E1A(+) and Taxol at concentration of 10–50 μM were given (FIGS. 33A and 33C).

A similar assay was conducted after giving V/T ratio of 400:1 Ad.E1A(+) against MDA-MB-435 cells. An appropriate control of Ad.E1A(−). Ad.E1A(−) with Taxol, Taxol alone, and Ad.E1A(+) alone were prepared and compared with Ad.E1A(+) with Taxol. Taxol was given from 0.1 $\mu$M to 100 $\mu$M (FIGS. 33B and 33D). No Synergistic effect was seen.

The suppression differences between Taxol alone and Taxol plus Ad.E1A(−) were almost the same at the Taxol doses of 0.1 $\mu$M to 100 $\mu$M (FIGS. 33A and 33C). Also, when treatment with 10 $\mu$M Taxol was analyzed based on a time scale at high infection (FIG. 34A) and low infection protocols (FIG. 34C), the survival fraction difference started around day 2 in the high infection protocol (FIG. 34A) and day 1 in the low infection protocols (FIG. 34C)with maximum difference at day 4.

Conversely there was no synergistic effect of Ad.E1A(+) with taxol on MDA-MB-435 cells (FIG. 34B and FIG. 34D). However these low neu expressing cells are more sensitive to taxol alone.

Clonogenic assay was done to see if transformation in the above condition would be inhibited (FIG. 35). Once again the synergistic effect between Taxol and E1A was observed in MDA-MB-453 cells. However, breast cancer cell line with low HER-2/neu expression (MDA-MB-435) did not show any synergistic effect in both MTT assay or soft agar clonogenic assay.

When direct cell counts were performed to check for viable cells using trypan blue 0.5% it was again clear that there was a synergistic effect of E1A and taxol (10 $\mu$M) against HER-2/neu-overexpressing breast cancer cell line MDA-MB453 on direct cell counting (FIG. 36A). However, there was no synergistic effect of Ad.E1A(+) V/T ratio of 400:1 and taxol on the viable cell fraction of MDA-MB-435, adenoviral vector was delivered under high infection protocol (FIG. 36B).

The results prove the concept of our hypothesis, namely the E1A-mediated HER-2/neu repression is able to sensitize the response of HER-2/neu-overexpressing cancer cells to chemotherapeutic agents. This phenomenon occurs only to the HER-2/neu-overexpressing cancer cells. When the breast cancer cells in which HER-2/neu is not overexpressed (MDA-MB-435), sensitization can not be observed either in MTT assay (FIG. 33) or clonogenic assay (FIG. 35).

EXAMPLE X

In Vivo Prevention of Breast, Lung and Ovarian Tumor Development in vivo by Inhibiting Tyrosine Kinase Activity of the HER-2/neu Receptor In an initial round of in vivo trials, inventors will use a mouse model of human cancer with the histologic features and metastatic potential resembling tumors seen in humans (Katsumata et al., 1995) and treat these animals with E1A or LT to examine the suppression of tumor development.

These studies are based on the discovery that Ad.E1A has tumor suppressor activity for neu-overexpressing cancer cells. The Examples above further show that Ad.E1A inhibits the growth of neu-mediated cancer cells and furthermore sensitizes neu-mediated cancer cells to chemotherapeutic drugs. The current example uses of either Ad.E1A or LT, in combination with chemotherapeutic drugs, to provide a useful preventive and therapeutic regimen for patients with neu-overexpressing cancers.

Two groups of mice of a suitable cancer model will be treated with doses of E1A or LT in combination with anti cancer drugs starting at 6 weeks of age. Several combinations and concentrations of E1A or LT and anti-cancer drugs will be tested. Control mice will be treated with buffer only.

The effect of E1A or LT, in combination with an anticancer drug, on the development of breast tumors will be compared with the control group by examination of tumor size, p185$^{neu}$ tyrosine kinase activity (using IP-western blot analysis) and histopathologic examination (breast tissue will be cut and stained with hematoxylin and eosin) of breast tissue. With the chemopreventive potential of E1A and LT, it is predicted that, unlike the control group of mice that develop tumors, the testing group of mice will be resistant to tumor development.

Breast Cancer Model

In order to obtain mice having human breast cancer, nu/nu mice may be given intraperitoneal injections of, for example, 2×10$^6$ viable neu overexpressing breast cancer cells from cell line MDA-MB-361 are injected in the mammary fat pad in nude mice. Palpable solid tumors are detected 1.5 months later.

These mice may then be given an appropriate dosage of E1A or LT using methods of delivery described above; in combination with an anti-cancer drug for 3 consecutive days, then once a week for six months.

Ovarian Cancer Model

In order to obtain mice having human ovarian cancer, nu/nu mice may be given intraperitoneal injections of, for example, 2×10$^6$ viable p185-overexpressing SKOV-3 human ovarian cancer cells. Mice sacrificed 5 days post treatment exhibit tumors resulting from such treatment.

Five days after treatment with the p185-overexpressing cells, mice may be separated into control and experimental groups. One group of mice will be left untreated. Other groups will be treated. Active compounds may be supplied to a treated group in phosphate buffer saline. One treated group will be treated with the buffered saline only. Another treated group may receive treatment with an appropriate dosage of E1A or LT. A third treated group may be treated with an appropriate dosage of an anti-cancer drug alone. A final group may be treated with an appropriate dosage of E1A or LT in combination with an anti-cancer drug. Treatments may be given using any of the methods described above.

Mice may be examined for tumor signs and symptoms, and killed when they appear moribund. Mice treated with the E1A or LT plus the anti-cancer drug will be expected to have a longer survival time.

Small Cell Lung Cancer Model

In order to obtain mice with the human lung cell cancer, nu/nu mice may be given as intratracheal injections of, for example, 2×10$^6$ viable neu overexpressing cancer cells from cell line H82. Five days after inoculation, following tumor formation, mice may be separated into groups to begin treatment. One group may be treated with an appropriate dosage of E1A or LT alone, another with an appropriate dosage of an anti-cancer drug alone. A third group may be treated with an appropriate dosage of E1A or LT in combination with an anticancer drug for 3 consecutive days, then once a week for two months.

EXAMPLE XI

Human Treatment with E1A or LT in Combination with Anti-Cancer Drugs or Alone This example describes a protocol to facilitate the treatment of neu-mediated cancer using E1A or LT in combination with anti-cancer drugs.

A patient presenting a neu-mediated cancer may be treated using the following protocol. neu-overexpression may be detected using the immunohistochemistry methods described below. Patients may, but need not, have received previous chemo-radio-or gene therapeutic treatments. Optimally the patient will exhibit adequate bone marrow function (defined as peripheral absolute granulocyte count of >2,000/mm3 and platelet count of 100,000/mm3, adequate liver function (bilirubin 1.5 mg/dl) and adequate renal function (creatinine 1.5 mg/dl).

Monitoring neu Overexpression in Tumors

The over-expression of new is typically monitored before, during, and after the therapy. The following assay may be used to monitor neu-overexpression. Sections of 3- to 4 mm thickness of the primary tumors and of the cell block preparations are cut, deparaffinized in xylene, and rehydrated in descending grades (100–70%) of ethanol. Endogenous peroxidase activity is blocked with 3% hydrogen peroxide in methanol. After several washes in distilled water and phosphate-buffered saline, the sections are incubated with a 1:10 dilution of normal horse serum to minimize background staining. This is followed by incubation for 1 hr at room temperature with the primary antibody (Ab-3 monoclonal antibody, Oncogene Sciences, Uniondale, N.Y.; 1:100). The peroxidase staining procedure utilizes ABC Elite Kits (Vector Laboratories, Burlingame, Calif.). The immunostaing reactions are visualized using 3-amino-9-ethylcarbazole as the chromogen. The sections and/or cytospin preparations are stained with toluidine blue and mounted in permount. Positive and negative control immunostains are also prepared.

The sections are reviewed by the pathologist. Two features of the immunoreaction will be recorded using a semi quantitative scale: the relative number of positive cells (0%, <10%, 10–50%, and >50%) and the intensity of the reaction (0–3). The pattern of immunostaining (membranous, cytoplasmic) is recorded separately. A tumor is considered neu positive if any neoplastic cells show cell membrane reactivity. Cytoplasmic staining is considered non-specific. A breast carcinoma known for its strong positive membrane staining will be used as a positive control.

The quantitative measurement of neu immunostaining will be performed using computerized image analysis with the SAMBA 4000 Cell Image Analysis System (Image Products International, Inc., Chantilly, Va.) integrated with a Windows based software. A strong staining tumor tissue section will be used as positive control. The primary antibody will be replaced by an isotype-matched irrelevant antibody to set the negative control threshold, averaging the results from ten fields.

Protocol for the Treatment of neu-Mediated Cancer

A composition of the present invention is typically administered orally or parenterally in dosage unit formulations containing standard, well known non-toxic physiologically acceptable carriers, adjuvants, and vehicles as desired. The term parenteral as used herein includes subcutaneous injections, intravenous, intramuscular, intra-arterial injection, or infusion techniques. The E1A or LT may be delivered to the patient before, after or concurrently with the other anti-cancer agents.

A typical treatment course may comprise about six doses delivered over a 7 to 21 day period. Upon election by the clinician the regimen may be continued six doses every three weeks or on a less frequent (monthly, bimonthly, quarterly etc.) basis. Of course, these are only exemplary times for treatment, and the skilled practitioner will readily recognize that many other time-courses are possible.

A major challenge in clinical oncology of neu-mediated cancers is that tumor cells over-expressing the neu-protooncogene are resistant to chemotherapeutic treatment. One goal of the inventors' efforts has been to find ways to improve the efficacy of chemotherapy. In the context of the present invention, E1A or LT can be combined with any of a number of conventional chemotherapeutic regimens.

To kill neu-overexpressing cancer cells using the methods and compositions described in the present invention one will generally contact a target cell with E1A or LT and at least one chemotherapeutic agent (second agent), examples of which are described above. These compositions will be provided in a combined amount effective to kill or inhibit the proliferation of the cell. This process may involve contacting the cell with E1A or LT and the second agent at the same time. Alternatively, this process may involve contacting the cell with a single composition or pharmacological formulation that includes both agents or by contacting the cell with two distinct compositions or formulations at the same time, wherein one composition includes the E1A or LT and the other includes the second agent.

Alternatively the E1A or LT administration may precede or follow the delivery of the second agent by intervals ranging from minutes to weeks. In embodiments where the E1A or LT and the second compound are applied separately, one would ensure that a significant period of time did not expire between the time of each delivery, such that the second agent and the E1A or LT would still be able to exert an advantageously combined effect on the cancer. In such instances, it is contemplated that one would contact the cell with both agents within about 6 hours to one week of each other and more preferably, within 24–72 hours of each other. In some situations however, it may be desirable to extend the time period for treatment significantly where several days (2, 3, 4, 5, 6, 7 or more) to several weeks (1, 2, 3, 4, 5, 6, 7 or more) lapse between respective administrations.

Regional delivery of E1A or LT will be an efficient method for delivering a therapeutically effective dose to counteract the clinical disease. Likewise, the chemotherapy may be directed to a particular effected region. Alternatively systemic delivery of either, or both, agent may be appropriate.

The therapeutic composition of the present invention is administered to the patient directly at the site of the tumor. This is in essence a topical treatment of the surface of the cancer. The volume of the composition should usually be sufficient to ensure that the entire surface of the tumor is contacted by the E1A or LT and second agent.

In one embodiment, administration simply entails injection of the therapeutic composition into the tumor. In another embodiment, a catheter is inserted into the site of the tumor and the cavity may be continuously perfused for a desired period of time.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least 1 month with no tumor sites showing enlargement. Similarly, a mixed response may be defined by a reduction of the product of perpendicular diameters of all measurable lesions by 50% or greater with progression in one or more sites.

Of course, the above-described treatment regimes may be altered in accordance with the knowledge gained from clinical trials such as those described in Example 14. Those of skill in the art will be able to take the information disclosed in this specification and optimize treatment regimes based on the clinical trials described in the specification.

EXAMPLE XII

Clinical Trials of the Use of E1A or LT in Combination with Anti-Cancer Drugs in Treating Neu-Mediated Cancer This example is concerned with the development of human treatment protocols using the E1A and LT in combination with anti-cancer drugs. E1A or LT and anti-cancer drug treatment will be of use in the clinical treatment of various neu-overexpressing cancers in which transformed or cancerous cells play a role. Such treatment will be particularly useful tools in anti-tumor therapy, for example, in treating patients with ovarian, breast and lung cancers that are mediated by neu over-expression and resistant to conventional chemotherapeutic regimens.

The various elements of conducting a clinical trial, including patient treatment and monitoring, will be known to those of skill in the art in light of the present disclosure. The following information is being presented as a general guideline for use in establishing E1A or LT in combinations with anti-cancer drugs in clinical trials.

Patients with advanced, metastatic breast and/or epithelial ovarian carcinoma chosen for clinical study will typically have failed to respond to at least one course of conventional therapy. Measurable disease is not required, however the patient must have easily accessible pleural effusion and/or ascites. Further the patients must carry tumors that overexpress neu oncoprotein. Overexpression may be defined as grade 2 or 3 staining by immunohistochemistry as described above. In an exemplary clinical protocol, patients may undergo placement of a Tenckhoff catheter, or other suitable device, in the pleural or peritoneal cavity and undergo serial sampling of pleural/peritoneal effusion. Typically, one will wish to determine the absence of known loculation of the pleural or peritoneal cavity, creatinine levels that are below 2 mg/dl, and bilirubin levels that are below 2 mg/dl. The patient should exhibit a normal coagulation profile.

In regard to the E1A or LT and other anti-cancer drug administration, a Tenckhoff catheter, or alternative device may be placed in the pleural cavity or in the peritoneal cavity, unless such a device is already in place from prior surgery. A sample of pleural or peritoneal fluid can be obtained, so that baseline cellularity, cytology, LDH, and appropriate markers in the fluid (CEA, CA15-3, CA 125, p185) and in the cells (E1A, p185) may be assessed and recorded.

In the same procedure, E1A or LT may be administered alone or in combination with the anti-cancer drug. The administration may be in the pleural/peritoneal cavity, directly into the tumor, or in a systemic manner. The starting dose may be 0.5 mg/kg body weight. Three patients may be treated at each dose level in the absence of grade >3 toxicity. Dose escalation may be done by 100% increments (0.5 mg, 1 mg, 2 mg, 4 mg) until drug related grade 2 toxicity is detected. Thereafter dose escalation may proceed by 25% increments. The administered dose may be fractionated equally into two infusions, separated by six hours if the combined endotoxin levels determined for the lot of E1A or LT and the lot of anti-cancer drug exceed 5EU/kg for any given patient.

The E1A or LT and anti-cancer drug combination may be administered over a short infusion time or at a steady rate of infusion over a 7 to 21 day period. The E1A or LT infusion may be administered alone or in combination with the anti-cancer drug. The infusion given at any dose level will be dependent upon the toxicity achieved after each. Hence, if Grade II toxicity was reached after any single infusion, or at a particular period of time for a steady rate infusion, further doses should be withheld or the steady rate infusion stopped unless toxicity improved. Increasing doses of E1A or LT in combination with an anti-cancer drug will be administered to groups of patients until approximately 60% of patients show unacceptable Grade III or IV toxicity in any category. Doses that are ⅔ of this value could be defined as the safe dose.

Physical examination, tumor measurements, and laboratory tests should, of course, be performed before treatment and at intervals of about 3–4 weeks later. Laboratory studies should include CBC, differential and platelet count, urinalysis, SMA-12-100 (liver and renal function tests), coagulation profile, and any other appropriate chemistry studies to determine the extent of disease, or determine the cause of existing symptoms. Also appropriate biological markers in serum should be monitored e.g. CEA, CA 15-3, p185 for breast cancer, and CA 125, p185 for ovarian cancer.

To monitor disease course and evaluate the anti-tumor responses, it is contemplated that the patients should be examined for appropriate tumor markers every 4 weeks, if initially abnormal. with twice weekly CBC, differential and platelet count for the 4 weeks; then, if no myelosuppression has been observed, weekly. If any patient has prolonged myelosuppression, a bone marrow examination is advised to rule out the possibility of tumor invasion of the marrow as the cause of pancytopenia. Coagulation profile shall be obtained every 4 weeks. An SMA-12-100 shall be performed weekly. Pleural/peritoneal effusion may be sampled 72 hours after the first dose, weekly thereafter for the first two courses, then every 4 weeks until progression or off study. Cellularity, cytology, LDH, and appropriate markers in the fluid (CEA, CA15-3, CA 125, p185) and in the cells (p185) may be assessed. For an example of an evaluation profile, see Table 4. When measurable disease is present, tumor measurements are to be recorded every 4 weeks. Appropriate radiological studies should be repeated every 8 weeks to evaluate tumor response. Spirometry and DLCO may be repeated 4 and 8 weeks after initiation of therapy and at the time study participation ends. An urinalysis may be performed every 4 weeks.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least 1 month with no tumor sites showing enlargement. Similarly, a mixed response may be defined by a reduction of the product of perpendicular diameters of all measurable lesions by 50% or greater with progression in one or more sites.

TABLE 4

EVALUATIONS BEFORE AND DURING THERAPY

| EVALUATIONS | PRE-STUDY | TWICE WEEKLY | WEEKLY | EVERY 4 WEEKS | EVERY 8 WEEKS |
|---|---|---|---|---|---|
| History | X | | | X | |
| Physical | X | | | X | |
| Tumor Measurements | X | | | X | |
| CBC | X | X[1] | X | | |
| Differential | X | X[1] | X | | |
| Platelet Count | X | X[1] | X | | |
| SMA12-100 (SGPT, Alkaline Phosphatase, Bilirubin, Alb/Total Protein) | X | | X | | |
| Coagulation Profile | X | | | X | |
| Serum Tumor markers (CEA, CA15-3, CA-125, Her-2/neu) | X | | | X[3] | |
| Urinalysis | X | | | X | |
| X-rays: | | | | | |
| chest | X | | X[4] | | |
| others | X | | | | X |
| Pleural/Peritoneal Fluids: (cellularity, cytology, LDH, tumor markers, E1A, HER-2/neu) | X | | X[5] | X | |
| Spirometry and DLCO | X | | | X[6] | X[6] |

[1]For the first 4 weeks, then weekly, if no myelosuppression is observed.
[2]As indicated by the patient's condition.
[3]Repeated every 4 weeks if initially abnormal.
[4]For patients with pleural effusion, chest X-rays may be performed at 72 hours after first dose, then prior to each treatment administration.
[5]Fluids may be assessed 72 hours after the first dose, weekly for the first two courses and then every 4 weeks thereafter.
[6]Four and eight weeks after initiation of therapy.

While the compositions and methods of this invention have been described in terms of preferred embodiments, it will be apparent to those of skill in the art that variations may be applied to the compositions, methods and in the steps or in the sequence of steps of the methods described herein without departing from the concept, spirit and scope of the invention. More specifically, it will be apparent that certain agents which are both chemically and physically related may be substituted for the agents described herein while the same or similar results would be achieved. All such similar substitutes and modifications apparent to those skilled in the art are deemed to be within the spirit, scope and concept of the invention as defined by the appended claims.

REFERENCE

The following references, to the extent that they provide exemplary procedural or other details supplementary to those set forth herein, are specifically incorporated herein by reference.

Adelman et al. (1983) *DNA* 2:183.
Alberts et al., *Clin. Pharmacol. Ther.*, 86:737–745, 1979.
Alley et al. (1988) *Cancer Res.*, 48:589.
Ayash, et al., *J Clin Oncol*, 12:37–44, 1994.
Baichwal and Sugden, In: Kucherlapati R, ed. Gene transfer. New York: Plenum Press, pp. 117–148, 1986.
Bargmann et al. (1986), *Nature*, 319:226–230.
Campisi et al. (1983), *Cell*, 33:357.
Chang et al. (1989), *J. Virol.*, 63:3479.
Chen et al. (1988), *BioTechniques*, 6:632.
Chen and Okayama, *Mol. Cell Biol.*, 7:2745–2752, 1987.
Cherington et al. (1988), *Mol. Cell. Biol.*, 8:1380–1384.
Coffin, In: *Virology*, Fields et al. (eds.), New York: Raven Press, pp. 1437–1500, 1990.
Couch et al., *Am. Rev. Resp. Dis.*, 88:394–403, 1963.
Coupar et al., *Gene*, 68:1–10, 1988.
Crea et al. (1978), *Proc. Natl. Acad. Sci. U.S.A* 75:5765.
DeCaprio et al. (1988), 54:275–283.
Downward et al. (1984), *Nature (London)*, 307:521.
Dubensky et al., *Proc. Nat'l Acad. Sci. USA*, 81:7529–7533, 1984.
Dynlacht et al. (1991), *Cell*, 66:563–576.
Eichenlaub, R. (1979), *J. Bacteriol* 138:559–566.
Evan et al. (1992), *Cell*, 69:119–128.
Fechheimer et al., *Proc. Nat'l Acad. Sci. USA*, 84:8463–8467, 1987.
Ferkol et al, *FASEB J.*, 7:1081–1091, 1993.
Figge et al. (1988), *J. Virol.*, 62:1814–1818.
Fraley et al., *Proc. Nat'l Acad. Sci. USA*, 76:3348–3352, 1979.
Friedmann, "Progress toward human gene therapy," *Science*, 244:1275–1281, 1989.
Frisch, S. M. (1991), *Proc. Natl. Acad. Sci. USA*, 88:9077–9081.
Gao et al., (1991), *Biochemical and Biophysical Research Communications*, 179(1):280–285.
Ghalie, et al., *J Clin Oncol*, 12:342–6, 1994.
Ghosh and Bachhawat, In: Wu G. and C. Wu ed. Liver diseases, targeted diagnosis and therapy using specific receptors and ligands. New York: Marcel Dekker, pp. 87–104, 1991.
Gomez-Foix et al., *J. Biol. Chem.*, 267:25129–25134, 1992.
Gopal, *Mol. Cell Biol.*, 5:1188–1190, 1985.
Gorman et al. (1982), *Mol. Cell. Biol.*, 2:1044–1051.
Graham and Prevec, *Biotechnology*, 20:363–390, 1992.
Graham and van der Eb, *Virology*, 52:456–467, 1973.
Gribskov et al. (1986), *Nucl. Acids Res.*, 14:6745.
Grunhaus and Horwitz, *Seminar in Virology*, 3:237–252, 1992.
Gusterson, et al., *J Clin Oncol*, 10:1049–56, 1992.
Haley et al. (1984), *Proc. Natl. Acad. Sci. USA*, 81:5734.
Harland and Weintraub, *J. Cell Biol.*, 101:1094–1099, 1985.
Harlow et al. (1985), *J. Virol.*, 55:533).
Hearing et al. (1985), *Mol. Cell. Biol.*, 5:3214.
Hen et al. (1985), *Science*, 230:1391.
Hermonat and Muzycska, *Proc. Nat'l Acad. Sci. USA*, 81:6466–6470, 1984.
Hersdorffer et al., *DNA Cell Biol.*, 9:713–723, 1990.
Herz and Gerard, *Proc. Nat'l Acad. Sci. USA* 90:2812–2816, 1993.
Horwich et al., *J. Virol.*, 64:642–650, 1990.
Houweling et al. (1980), *Virology*, 105:537.
Hung et al., *Proc. Natl. Acad. Sci. USA*, 86:2545–2548, 1989.
Johnson et al. (1988), *J. Biol. Chem.*, 263:5693–5699.
Kalderon et al. (1984), *Virology*, 139:109–137.
Kaneda et al., "Increased expression of DNA cointroduced with nuclear protein in adult rat liver," *Science*, 243: 375–378, 1989.
Karlsson et al., *EMBO J.*, 5:2377–2385, 1986.
Kato et al., "Expression of hepatitis B virus surface antigen in adult rat liver," *J. Biol. Chem.*, 266:3361–3364, 1991.
Klein et al., *Nature*, 327:70–73, 1987.
Kraus et al. (1987), *EMBO J.*, 6:605.

Kyte & Doolittle, *J. Mol. Biol.*, 157:105–132, 1982.
Land et al. (1983), *Science*, 222:771.
Le Gal La Salle et al., *Science*, 259:988–990, 1993.
Levrero et al., *Gene*, 101: 195–202, 1991.
Livingston et al. (1987), *Mol. Biol. Med.*, 4:63–80.
Mann et al., *Cell*, 33:153–159, 1983.
Markowitz et al., *J. Virol.*, 62:1120–1124, 1988.
Matin et al. (1989), *Oncogene*, 5:111.
McCann, et al., *Cancer Res*, 51:3296–303, 1991.
Messing et al. (1981) Third Cleveland Symposium on Macromolecules and Recombinant DNA, Editor A. Walton, Elsevier, Amsterdam.
Mitchell et al. (1989), *Science*, 245:371.
Moran et al. (1987), *Cell*, 48:177.
Muller et al. (1982), *Nature (London)*, 299:640.
Muller et al., *Cell*, 54:105–115, 1988.
Muro-cacho, C. A. (1992), *J. of Immunotherapy*, 11:231–237.
Muss, et al., *N. Engl J Med*, 330:1260–6, 1994.
Nabel et al. (1990), *Science*, 249:1285–1288.
Needleman et al. (1970), *J. Mol. Biol.*, 48:443.
Nelson et al. (1990), *Proc. Natl. Acad. Sci. USA*, 87:8041–8045.
Nicolas & Rubenstein, In: *Vectors: A survey of molecular cloning vectors and their uses*, Rodriguez & Denhardt (eds.), Stoneham: Butterworth, pp. 493–513, 1988.
Nicolau et al. (1987), *Methods in Enzymology*, 149:157–176.
Nicolau and Sene, *Biochem. Biophys. Acta*, 721:185–190, 1982.
Padhy et al. (1982), *Cell*, 28: 865–871.
Paskind et al., *Virology*, 67:242–248, 1975.
Perales et al., *Proc. Natl. Acad. Sci. USA*, 91:4086–4090, 1994.
Peters, et al., *J Clin Oncol*, 11:1132–43, 1993.
Potter et al., "*Proc. Nat'l Acad. Sci. USA*, 81:7161–7165, 1984.
Pozzatti et al. (1988), *Mol. Cell. Biol.*, 8:2984.
Ragot et al., *Nature*, 361:647–650, 1993.
Rao et al. (1992), *Proc. Natl. Acad. Sci. USA*, 89:7742–7746.
Rich et al., *Hum. Gene Ther.*, 4:461–476, 1993.
Ridgeway, In: Rodriguez R L, Denhardt D T, ed. Vectors: A survey of molecular cloning vectors and their uses. Stoneham: Butterworth, pp. 467–492, 1988.
Rippe et al., *Mol. Cell Biol.*, 10:689–695, 1990.
Rosenfeld et al., *Cell*, 68:143–155, 1992.
Rosenfeld et al., *Science*, 252:431–434, 1991.
Roux et al., *Proc. Natl. Acad. Sci. USA*, 86:9079–9083, 1989.
Ruley, H. E. (1985), *Nature(London)*, 304:602.
Rustgi et al. (1991), *Nature*, 352:541–544.
Schechter et al., *Nature*, 312:513–516, 1984.
Schwartz et al., eds. (1979), *Atlas of Protein Sequence and Structure*, National Biomedical Research Foundation, pgs. 353–358.
Senba et al. (1985), *Proc. Natl. Acad. Sci. USA*, 82:6497.
Shih et al. (1981), *Nature (London)*, 290:261–264.
Slamon et al., (1989), 244:707–712.
Slamon, et al., *Science*, 240:177–182, 1987.
Smith et al. (1981), *Adv. Appl. Math.*, 2:482.
Smith and Rutledge, "Chemotherapy in advanced ovarian cancer," *Natl. Cancer Inst. Monogr.*, 42:141–143, 1975.
Southern et al. (1982), *J. Mol. Appl. Genet.*, 1:327.
Steeg et al. (1988), *Cancer Res.*, 48:6550–6554.
Stein et al. (1987), *Mol. Cell. Biol.*, 7:1164.
Stratford-Penicaudet and Perricaudetp. 51–61, In: *Human Gene Transfer*, Eds, O. Cohen-Haguenauer and M. Boiron, Editions John Libbey Eurotext, France, 1991.
Stratford-Penicaudet et al., *Hum. Gene Ther.*, 1:241–256, 1990.
Suen et al. (1990), *Mol. Cell. Biol.*, 10:6306–6315.
Tal et al. (1987), *Mol. Cell. Biol.*, 7:2597.
Temin, In: *Gene Transfer*, Kucherlapati (ed.), New York: Plenum Press, pp. 149–188, 1986.
Toikkanen, et al., *J Clin Onc*, 10:1044–48, 1992.
Top et al., *J. Infect. Dis.*, 124:155–160, 1971.
Towbin et al. (1979), *Proc. Natl. Acad. Sci., USA*, 76:4350.
Tur-Kaspa et al., *Mol. Cell Biol.*, 6:716–718, 1986.
Tsai, et al., *J Natl Cancer Inst*, 87:682–4, 1995.
Van Dam et al. (1989), *Oncogene*, 4:1207.
Varmus et al., *Cell*, 25:23–36, 1981.
Velcich et al. (1986), *Mol. Cell. Biol.*, 6:4019.
Vijver, et al., *Mol. Cell. Biol.*, 7:2019–23, 1987.
Wagner et al., *Science*, 260:1510–1513, 1990.
Wallich et al. (1985), *Nature (London)*, 315:301.
Wang et al. (1991), *Mol. Cell. Biol.*, 11:4253–4265.
Whyte et al. (1988), *Nature (London)*, 334:124–129.
Yan, et al., *Oncogene*, 6:343–345, 1991.
Wu and Wu, *J. Biol. Chem.*, 262:4429–4432, 1987.
Wu and Wu, *Biochemistry*, 27:887–892, 1988.
Yanisch-Perron et al. (1985), *Gene*, 33:103–109.
Young et al., *N. Engl. J. Med.*, 299:1261–1266, 1978.
Yu, et al., *Proc Natl Acad Sci USA*, 87:4499–503, 1990.
Weinberg, R. A. (1985), *Science*, 230:770–776.
Zelenin et al., *FEBS Lett.*, 280:94–96, 1991.
Zhang et al. (1989), *Oncogene*, 4:985–989.

What is claimed is:

1. A method for suppressing growth of a tumor comprising a neu oncogene cell, comprising contacting the cell in the tumor with an E1A gene product and a chemotherapeutic drug in amounts effective to suppress growth of the tumor, wherein the E1A gene product is introduced into the cell by introduction of a nucleic acid encoding the E1A gene product linked to a promoter and obtaining expression of the E1A gene product.

2. The method of claim 1, wherein growth of the tumor is neu oncogene-mediated.

3. The method of claim 1, wherein the chemotherapeutic drug is an alkylating agent, a plant alkaloid, an antibiotic or an antineoplastic agent.

4. The method of claim 3, wherein the chemotherapeutic drug is an alkylating agent.

5. The method of claim 4, wherein the alkylating agent is mechlorethamine, cyclophosphamide, ifosfamide chlorambucil, melphalan, busulfan, thiotepa, carmustine, lomustine, or streptozocin.

6. The method of claim 3, wherein the chemotherapeutic drug comprises a plant alkaloid.

7. The method of claim 6, wherein the plant alkaloid is vincristine, vinblastine or paclitaxel.

8. The method of claim 7, wherein the plant alkaloid is vincristine.

9. The method of claim 7, wherein the plant alkaloid is vinblastine.

10. The method of claim 7, wherein the plant alkaloid is paclitaxel.

11. The method of claim 3, wherein the chemotherapeutic drug is an antibiotic.

12. The method of claim 11, wherein the antibiotic is dactinomycin, daunorubicin, idarubicin, bleomycin, mitomycin, or doxorubicin.

13. The method of claim 12, wherein the antibiotic is dactinomycin.

14. The method of claim 12, wherein the antibiotic is daunorubicin.

15. The method of claim 12, wherein the antibiotic is idarubicin.

16. The method of claim 12, wherein the antibiotic is bleomycin.

17. The method of claim 12, wherein the antibiotic is mitomycin.

18. The method of claim 12, wherein the antibiotic is doxorubicin.

19. The method of claim 3, wherein the chemotherapeutic drug is an antineoplastic agent.

20. The method of claim 19, wherein the antineoplastic agent is selected from the group consisting of cisplatin, VP16, and TNF.

21. The method of claim 20, wherein the antineoplastic agent is cisplatin.

22. The method of claim 20, wherein the antineoplastic agent is VP16.

23. The method of claim 20, wherein the antineoplastic agent is TNF.

24. The method of claim 1, wherein the E1A gene product is introduced to the cell prior to the administration of the chemotherapeutic drug.

25. The method of claim 1, wherein the chemotherapeutic drug is administered to the cell prior to introduction of the E1A gene product.

26. The method of claim 1, wherein the E1A gene product is introduced to the cell and the chemotherapeutic drug is administered to the cell substantially simultaneously.

27. The method of claim 1, wherein the cell is located within an animal and effective amounts of the E1A gene product and the chemotherapeutic drug are administered to the animal.

28. The method of claim 1, wherein the chemotherapeutic drug is suitably dispersed in a pharmacologically acceptable formulation.

29. The method of claim 1, wherein the cell is contacted with a single composition for introducing the E1A gene product and administering the chemotherapeutic drug.

30. The method of claim 29, wherein the composition is suitably dispersed in a pharmacologically acceptable formulation.

31. The method of claim 1, wherein the E1A gene product is the E1A 12S or 13S gene product.

32. The method of claim 1, wherein the E1A gene product is either the E1A 12S or 13S gene product.

33. The method of claim 1, wherein the nucleic acid encodes both the E1A 12S and 13S gene products.

34. The method of claim 1, wherein the nucleic acid encoding the E1A gene product encodes a mini-E1A gene product.

35. The method of claim 1, wherein the nucleic acid encoding the E1A gene product is introduced into the cell using an E1A nucleic acid/lipid complex.

36. The method of claim 35, wherein the lipid comprises DOTMA, DOPE, or DC-Chol.

37. The method of claim 35, wherein the lipid comprises DC-Chol.

38. The method of claim 35, wherein the lipid comprises DC-Chol and DOPE.

39. The method of claim 35, wherein the DNA/lipid complex is administered by injection.

40. The method of claim 1, wherein the E1A gene product is introduced into the cell by introduction of a vector containing a gene encoding the E1A gene product.

41. The method of claim 40, wherein the vector is a viral vector.

42. The method of claim 41, wherein the vector is an adenoviral vector.

43. The method of claim 40, wherein the cell is a human cell.

44. The method of claim 43, wherein the cell is a lung cancer cell.

45. A method for suppressing growth of a neu-mediated cancer in an animal having or suspected of having the cancer comprising administering to the animal an effective combination of E1A gene product and chemotherapeutic drug in an effective amount to suppress growth of the cancers wherein the E1A gene product is administered by introducing to the animal a nucleic acid encoding the E1A gene product linked to a promoter and obtaining expression of the E1A gene product.

46. The method of claim 45, wherein growth of the cancer is neu oncogene-mediated.

47. The method of claim 45, wherein the animal is a mammal.

48. The method of claim 47, wherein the mammal is a human.

49. The method of claim 48, wherein the cancer is lung cancer.

50. The method of claim 45, wherein the chemotherapeutic drug is an alkylating agent, a plant alkaloid, an antibiotic or an antineoplastic agent.

51. The method of claim 50, wherein the chemotherapeutic drug is an alkylating agent.

52. The method of claim 51, wherein the alkylating agent is mechlorethamine, cyclophosphamide, ifosfamide chlorambucil, melphalan, busulfan, thiotepa, carmustine, lomustine, or streptozocin.

53. The method of claim 50, wherein the chemotherapeutic drug comprises a plant alkaloid.

54. The method of claim 53, wherein the plant alkaloid is vincristine, vinblastine or paclitaxel.

55. The method of claim 54, wherein the plant alkaloid is vincristine.

56. The method of claim 54, wherein the plant alkaloid is vinblastine.

57. The method of claim 54, wherein the plant alkaloid is paclitaxel.

58. The method of claim 50, wherein the chemotherapeutic drug is an antibiotic.

59. The method of claim 58, wherein the antibiotic is dactinomycin, daunorubicin, idarubicin, bleomycin, mitomycin, or doxorubicin.

60. The method of claim 59, wherein the antibiotic is dactinomycin.

61. The method of claim 59, wherein the antibiotic is daunorubicin.

62. The method of claim 59, wherein the antibiotic is idarubicin.

63. The method of claim 59, wherein the antibiotic is bleomycin.

64. The method of claim 59, wherein the antibiotic is mitomycin.

65. The method of claim 59, wherein the antibiotic is doxorubicin.

66. The method of claim 50, wherein the chemotherapeutic drug is an antineoplastic agent.

67. The method of claim 66, wherein the antineoplastic agent is selected from the group consisting of cisplatin, VP16, and TNF.

68. The method of claim 67, wherein the antineoplastic agent is cisplatin.

69. The method of claim 67, wherein the antineoplastic agent is VP16.

70. The method of claim 67, wherein the antineoplastic agent is TNF.

71. The method of claim 45, comprising introducing into the animal a therapeutically effective amount of an E1A gene product and contacting the animal with a chemotherapeutic drug.

72. The method of claim 45, wherein a cancer site is contacted with a chemotherapeutic drug by administering to the animal a therapeutically effective amount of a pharmaceutical composition comprising a chemotherapeutic drug.

73. The method of claim 45, wherein the E1A gene product is the E1A 12S or 13S gene product.

74. The method of claim 45, wherein the E1A gene product is either the E1A 12S or 13S gene product.

75. The method of claim 45, wherein the E1A gene encodes both the E1A 12S and 13S gene products.

76. The method of claim 45, wherein the gene encoding the E1A gene product is introduced to the animal by introduction of an adenovirus.

77. The method of claim 45, wherein the gene encoding the E1A gene product encodes a mini-E1A gene product.

78. The method of claim 45, wherein the gene encoding the E1A gene product is introduced to the animal using an E1A nucleic acid/lipid complex.

79. The method of claim 45, wherein the lipid comprises DOTMA, DOPE, or DC-Chol.

80. The method of claim 78, wherein the lipid comprises DC-Chol.

81. The method of claim 78, wherein the lipid comprises DC-Chol and DOPE.

82. The method of claim 78, wherein the DNA/lipid complex is administered by injection.

83. The method of claim 45, wherein the E1A gene product is administered by introducing to the animal a vector containing a gene encoding the E1A gene product.

84. The method of claim 83, wherein the vector is a viral vector.

85. The method of claim 84, wherein the vector is an adenoviral vector.

86. A pharmaceutical composition comprising nucleic acid encoding an E1A gene product linked to a promoter and a chemotherapeutic drug in a pharmaceutically acceptable carrier.

87. The composition of claim 86, wherein the chemotherapeutic drug is an alkylating agent, a plant alkaloid, an antibiotic or an antineoplastic agent.

88. The composition of claim 87, wherein the chemotherapeutic drug is an alkylating agent.

89. The composition of claim 88, wherein the alkylating agent is mechlorethamine, cyclophosphamide, ifosfamide chlorambucil, melphalan, busulfan, thiotepa, carmustine, lomustine, or streptozocin.

90. The composition of claim 87, wherein the chemotherapeutic drug comprises a plant alkaloid.

91. The composition of claim 90, wherein the plant alkaloid is vincristine or vinblastine.

92. The composition of claim 91, wherein the plant alkaloid is vincristine.

93. The composition of claim 91, wherein the plant alkaloid is vinblastine.

94. The composition of claim 87, wherein the chemotherapeutic drug is an antibiotic.

95. The composition of claim 94, wherein the antibiotic is dactinomycin, daunorubicin, idarubicin, bleomycin, mitomycin, or doxorubicin.

96. The composition of claim 95, wherein the antibiotic is dactinomycin.

97. The composition of claim 95, wherein the antibiotic is daunorubicin.

98. The composition of claim 95, wherein the antibiotic is idarubicin.

99. The composition of claim 95, wherein the antibiotic is bleomycin.

100. The composition of claim 95, wherein the antibiotic is mitomycin.

101. The composition of claim 95, wherein the antibiotic is doxorubicin.

102. The composition of claim 87, wherein the chemotherapeutic drug is an antineoplastic agent.

103. The composition of claim 102, wherein the antineoplastic agent is VP16 or TNF.

104. The composition of claim 103, wherein the antineoplastic agent is VP16.

105. The composition of claim 103, wherein the antineoplastic agent is TNF.

106. The pharmaceutical composition of claim 86, wherein the nucleic acid encoding the E1A gene product and the chemotherapeutic drug are comprised in the same pharmaceutical composition.

107. A therapeutic kit comprising a pharmaceutical formulation of a nucleic acid encoding an E1A gene product and a pharmaceutical formulation of a chemotherapeutic drug.

108. The kit of claim 107, wherein the pharmaceutical formulation of a nucleic acid encoding an E1A gene product and the pharmaceutical formulation of a chemotherapeutic drug are present within distinct containers.

* * * * *

UNITED STATES PATENT AND TRADEMARK OFFICE
CERTIFICATE OF CORRECTION

PATENT NO.      : 7,005,424
APPLICATION NO. : 09/943984
DATED           : February 28, 2006
INVENTOR(S)     : Hung et al.

Page 1 of 1

It is certified that error appears in the above-identified patent and that said Letters Patent is hereby corrected as shown below:

Column 84,
Line 1, replace "claim 45" with -- claim 78 --.

Signed and Sealed this

Twenty-seventh Day of June, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,005,424 B2 | Page 1 of 1 |
| APPLICATION NO. | : 09/943984 | |
| DATED | : February 28, 2006 | |
| INVENTOR(S) | : Mien-Chie Hung et al. | |

It is certified that error appears in the above-identified patent and that said Letters Patent is hereby corrected as shown below:

In column 1, line 10, insert --This invention was made with government support under CA076450 awarded by The National Institutes of Health. The government has certain rights in the invention.--.

Signed and Sealed this

Eighth Day of July, 2008

JON W. DUDAS
*Director of the United States Patent and Trademark Office*